(12) United States Patent
Che et al.

(10) Patent No.: US 9,777,305 B2
(45) Date of Patent: *Oct. 3, 2017

(54) METHOD FOR THE ASSEMBLY OF A POLYNUCLEIC ACID SEQUENCE

(75) Inventors: Austin Che, Boston, MA (US); Tom Knight, Boston, MA (US); Barry Canton, Boston, MA (US); Jason Kelly, Boston, MA (US); Reshma Shetty, Boston, MA (US); Maiwenn Kersaudy Kerhoas, Edinburgh (GB); Farid Amalou, Edinburgh (GB); Will Shu, Edinburgh (GB)

(73) Assignee: Iti Scotland Limited, Glasgow (GB)

( * ) Notice: Subject to any disclaimer, the term of this patent is extended or adjusted under 35 U.S.C. 154(b) by 308 days.

This patent is subject to a terminal disclaimer.

(21) Appl. No.: 13/806,358

(22) PCT Filed: Jun. 23, 2011

(86) PCT No.: PCT/GB2011/000944
§ 371 (c)(1),
(2), (4) Date: Jun. 13, 2013

(87) PCT Pub. No.: WO2011/161413
PCT Pub. Date: Dec. 29, 2011

(65) Prior Publication Data
US 2014/0030766 A1 Jan. 30, 2014

(30) Foreign Application Priority Data
Jun. 23, 2010 (GB) .................................. 1010589.8

(51) Int. Cl.
| | | |
|---|---|---|
| C12P 19/34 | (2006.01) |
| B01F 11/00 | (2006.01) |
| B01F 11/02 | (2006.01) |
| B01F 13/00 | (2006.01) |
| B01F 13/08 | (2006.01) |
| C12N 15/10 | (2006.01) |
| C12Q 1/68 | (2006.01) |
| C12N 15/66 | (2006.01) |
| B01L 3/00 | (2006.01) |
| B01L 7/00 | (2006.01) |

(52) U.S. Cl.
CPC ............ *C12P 19/34* (2013.01); *B01F 11/0051* (2013.01); *B01F 11/0071* (2013.01); *B01F 11/0241* (2013.01); *B01F 13/0059* (2013.01); *B01F 13/0818* (2013.01); *B01L 3/502761* (2013.01); *C12N 15/10* (2013.01); *C12N 15/1031* (2013.01); *C12N 15/1093* (2013.01); *C12N 15/66* (2013.01); *C12Q 1/6806* (2013.01); *B01F 2215/0454* (2013.01); *B01L 3/502707* (2013.01); *B01L 3/502715* (2013.01); *B01L 3/502753* (2013.01); *B01L 7/52* (2013.01); *B01L 2200/025* (2013.01); *B01L 2200/04* (2013.01); *B01L 2300/044* (2013.01); *B01L 2300/0867* (2013.01); *B01L 2300/0887* (2013.01); *B01L 2400/043* (2013.01); *B01L 2400/0655* (2013.01)

(58) Field of Classification Search
None
See application file for complete search history.

(56) References Cited

U.S. PATENT DOCUMENTS

| | | |
|---|---|---|
| 2,677,390 A | 5/1954 | Davis et al. |
| 3,603,346 A | 9/1971 | Hirt |
| 4,119,120 A | 10/1978 | Mehaffy et al. |
| 4,848,722 A | 7/1989 | Webster |
| 4,852,851 A | 8/1989 | Webster |
| 4,858,883 A | 8/1989 | Webster |
| 5,176,359 A | 1/1993 | Leveson et al. |
| 5,258,292 A | 11/1993 | Yeh et al. |
| 5,344,117 A | 9/1994 | Trah et al. |
| 5,362,489 A | 11/1994 | Kishimoto et al. |
| 5,593,290 A | 1/1997 | Greisch et al. |
| 5,932,799 A | 8/1999 | Moles |
| 6,056,269 A | 5/2000 | Johnson et al. |
| 6,073,482 A | 6/2000 | Moles |
| 6,440,669 B1 | 8/2002 | Bass et al. |
| 6,521,427 B1 | 2/2003 | Evans |

(Continued)

FOREIGN PATENT DOCUMENTS

| | | |
|---|---|---|
| DE | 10238600 | 3/2004 |
| DE | 102006059459 | 7/2008 |

(Continued)

OTHER PUBLICATIONS

Colgee et al., "Seamless gene engineering using RNA- and DNA-overhang cloning" 18 Nature Biotechnology 789-791 (2000).*

(Continued)

*Primary Examiner* — Nancy J Leith
(74) *Attorney, Agent, or Firm* — Stradley Ronon Stevens & Young, LLP

(57) ABSTRACT

Provided herein are methods for the assembly of a polynucleic acid sequence that is at least partially carried out on a microfluidic device; methods for the preparation of a library of polynucleic acid sequences; microfluidic devices; methods for designing nucleic acid sequences; methods for planning the assembly of a polynucleic acid sequence from a plurality of nucleic acid sequences; systems comprising components for carrying out these methods; computer programs which, when run on a computer, implements these methods; and computer readable medium or carrier signals encoding such a computer program.

9 Claims, 41 Drawing Sheets

(56) References Cited

U.S. PATENT DOCUMENTS

| | | |
|---|---|---|
| 6,524,456 B1 | 2/2003 | Ramsey et al. |
| 6,843,263 B2 | 1/2005 | Kuo et al. |
| 6,935,617 B2 | 8/2005 | Mead et al. |
| 7,238,268 B2 | 7/2007 | Ramsey et al. |
| 7,258,774 B2 | 8/2007 | Chou et al. |
| 7,284,966 B2 | 10/2007 | Xu et al. |
| 7,291,512 B2 | 11/2007 | Unger |
| 7,378,280 B2 | 5/2008 | Quake et al. |
| 7,407,799 B2 | 8/2008 | Balagadde et al. |
| 7,413,712 B2 | 8/2008 | Liu et al. |
| 7,476,363 B2 | 1/2009 | Unger et al. |
| 7,479,186 B2 | 1/2009 | Quake et al. |
| 7,494,555 B2 | 2/2009 | Unger et al. |
| 7,608,160 B2 | 10/2009 | Zhou et al. |
| 7,766,033 B2 | 8/2010 | Mathies et al. |
| 7,832,429 B2 | 11/2010 | Young et al. |
| 7,837,821 B2 | 11/2010 | Zhou et al. |
| 7,959,875 B2 | 6/2011 | Zhou et al. |
| 7,976,795 B2 | 7/2011 | Zhou et al. |
| 8,646,482 B2 | 2/2014 | Zhou et al. |
| 8,999,679 B2 * | 4/2015 | Che et al. ............ 435/91.41 |
| 2002/0025561 A1 | 2/2002 | Hodgson |
| 2002/0037221 A1 | 3/2002 | Mastrangelo |
| 2002/0106680 A1 | 8/2002 | Shinmyo et al. |
| 2004/0209354 A1 | 10/2004 | Mathies et al. |
| 2005/0284817 A1 | 12/2005 | Fernandez et al. |
| 2006/0281113 A1 * | 12/2006 | Church et al. ............ 435/6 |
| 2007/0036026 A1 | 2/2007 | Laibinis et al. |
| 2007/0166199 A1 | 7/2007 | Zhou et al. |
| 2007/0209572 A1 | 9/2007 | Hansen et al. |
| 2007/0237686 A1 | 10/2007 | Mathies et al. |
| 2007/0243110 A1 | 10/2007 | Chiou et al. |
| 2007/0267294 A1 | 11/2007 | Shenderov |
| 2007/0269870 A1 | 11/2007 | Church et al. |
| 2008/0124245 A1 | 5/2008 | Ito et al. |
| 2008/0160622 A1 | 7/2008 | Su et al. |
| 2008/0160634 A1 | 7/2008 | Su et al. |
| 2008/0160639 A1 | 7/2008 | Su et al. |
| 2009/0057599 A1 | 3/2009 | Namkoong |
| 2009/0060797 A1 | 3/2009 | Mathies et al. |
| 2009/0087840 A1 | 4/2009 | Baynes et al. |
| 2009/0185955 A1 | 7/2009 | Nellissen |
| 2009/0294055 A1 | 12/2009 | Zhou et al. |
| 2010/0035768 A1 * | 2/2010 | Gibson ............ C12N 15/10 506/17 |
| 2011/0041935 A1 | 2/2011 | Zhou et al. |
| 2011/0162785 A1 | 7/2011 | Zhou et al. |

FOREIGN PATENT DOCUMENTS

| | | |
|---|---|---|
| DE | 102008003823 | 7/2008 |
| EP | 1065378 | 6/2000 |
| EP | 1159285 | 12/2001 |
| EP | 1215399 | 6/2002 |
| EP | 1202802 | 9/2004 |
| EP | 1539350 | 6/2005 |
| EP | 1940549 | 7/2008 |
| EP | 1979097 | 10/2008 |
| EP | 2071189 | 6/2009 |
| EP | 2105202 | 9/2009 |
| EP | 2265375 | 12/2010 |
| EP | 2292710 | 3/2011 |
| EP | 1706467 | 8/2011 |
| WO | 9102077 | 2/1991 |
| WO | 9914318 | 3/1999 |
| WO | 9947536 | 9/1999 |
| WO | 0049142 | 8/2000 |
| WO | 0077181 | 12/2000 |
| WO | 0112327 | 2/2001 |
| WO | 0188173 | 11/2001 |
| WO | 0194366 | 12/2001 |
| WO | 0228533 | 4/2002 |
| WO | 0229106 | 4/2002 |
| WO | 02068849 | 9/2002 |
| WO | 02087754 | 11/2002 |
| WO | 03044193 | 3/2003 |
| WO | 03054232 | 7/2003 |
| WO | 03085094 | 10/2003 |
| WO | WO2004040001 | 10/2003 |
| WO | 2004028955 | 4/2004 |
| WO | 2004035781 | 4/2004 |
| WO | 2004061085 | 7/2004 |
| WO | 2005051970 | 6/2005 |
| WO | 2005060393 | 7/2005 |
| WO | 2005071077 | 8/2005 |
| WO | 2005071111 | 8/2005 |
| WO | 2005080606 | 9/2005 |
| WO | 2006043922 | 4/2006 |
| WO | 2006044956 | 4/2006 |
| WO | WO2006127423 | 11/2006 |
| WO | 2007032859 | 3/2007 |
| WO | 2007040592 | 4/2007 |
| WO | 2007064404 | 6/2007 |
| WO | 2007084425 | 7/2007 |
| WO | 2007123742 | 11/2007 |
| WO | 2007136736 | 11/2007 |
| WO | 2007136834 | 11/2007 |
| WO | 2007137242 | 11/2007 |
| WO | 2008024129 | 2/2008 |
| WO | 2008024176 | 2/2008 |
| WO | WO2008024319 | 2/2008 |
| WO | 2008027558 | 3/2008 |
| WO | 2008075368 | 6/2008 |
| WO | 2008103824 | 8/2008 |
| WO | 2008115626 | 9/2008 |
| WO | 2008118098 | 10/2008 |
| WO | 2008127283 | 10/2008 |
| WO | 2008130623 | 10/2008 |
| WO | 2008144192 | 11/2008 |
| WO | WO2009020435 | 2/2009 |
| WO | 2009049268 | 4/2009 |
| WO | 2009061168 | 5/2009 |
| WO | 2009149218 | 12/2009 |
| WO | 2010025310 | 3/2010 |
| WO | WO2010070295 | 6/2010 |
| WO | 2010073020 | 7/2010 |

OTHER PUBLICATIONS

Zhang, H. et al., "On-chip oligonucleotide ligation assay using one-dimensional microfluidic beads array for the detection of low-abundant DNA point mutations", Biosensors and Bioelectronics, 2008, 23:945-951.

Liu, Y. et al., "DNA ligation of ultramicro volume using an EWOD microfluidic system with coplanar electrodes", J. Micromech. Microeng., 2008, 18(4):45017.

Lu, C. et al., "Comparison of Multiple Gene Assembly Methods for Metabolic Engineering", Applied Biochemistry and Biotechnology, 2007, 137:703-710.

Tsuge, K. et al., "One step assembly of multiple DNA fragments with a designed order and orientation in Bacillus subtilis plasmid", Nucleic Acids Research, 2003, 31(21):e133.

Xiong, A. et al., "Non-polymerase-cycling-assembly-based chemical gene synthesis: Strategies, methods and progress", Biotechnology Advances, 2008, 26:121-134.

Kong, D.S. et al., "Parallel gene synthesis in a microfluidic device", Nucleic Acids Research, 2007, 35(8):e61.

Zhou, X. et al., "Microfluidic PicoArray synthesis of oligodeoxynucleotides and simultaneous assembling of multiple DNA sequences", 2004, 32(18):5409-5417.

BioBrick assembly manual from http://ginkgobioworks.com/ support/BioBrick_Assembly_Manual.pdf, May 14, 2015.

Blake et al., Pairwise selection assembly for sequence-independent construction of long-longth DNA, Nucl Acids Res 2010 38(8):2594-2602.

Ellis et al., Diversity-based, model-guided construction of synthetic gene networks with predicted functions, Nat Biotechnol 2009 27(5):465-71.

Gibson et al., Enzymatic assembly of DNA molecules up to several hundred kilobases, Nat Methods 2009 6(5):343-5.

(56) References Cited

OTHER PUBLICATIONS

International Preliminary Report on Patentability dated Jun. 29, 2011 in Application No. PCT/GB2009/002968.
International Search Report dated May 18, 2010 in Application No. PCT/GB2009/002968.
Knight, Idempotent Vector Design for Standard Assembly of Biobricks (2003) MIT Articial Intelligence Laboratory, 11 pages.
Lee et al., A microfluidic oligonucleotide synthesizer, Nucl Acids Res 2010 39(8):2514-2521.
Lewin, Genes IV. Oxford University Press; 4th edition 1990 pp. 453-456.
Sambrook, Molecular Cloning, A Laboratory Manual, Cold Spring Harbor Laboratory Press; 3rd edition, 2001, pp. 8.22-8.26.
Unger et al, Monolithic microfabricated valves and pumps by multilayer soft lithography, Science 2000 288 (5463):113-116.
Written Opinion dated May 18, 2010 in Application No. PCT/GB2009/002968.
Zeevi et al., Increasing cloning possibilities using artificial zinc finger nucleases, PNAS 2008 105(35):12785-90.
Ivanov et al., Shotgun concatenation of synthetic genes: construction of concatemeric human calcitonin genes, Anal Biochem 1990 189(2):213-6.
So et al., Increasing the efficiency of SAGE adaptor ligation by directed ligation chemistry, Nucleic Acids Res 2004 32(12):e96 PMC484191.
Brenner et al., Gene expressio nanalysis by massively parallel signature sequencing (MPSS) on nicrobead arrays, Nat Biotehcnol 2000 18(6):630-4.

\* cited by examiner

Phase 1: Part Preparation

Phase 2: Part / Linker Pairing

Phase 3: Pathway Assembly

▮ = 3 base pair scar

◗ = part specific linker

SEQUENCE LISTING

```
<160> NUMBER OF SEQ ID NOS: 4

<210> SEQ ID NO 1
<211> LENGTH: 11
<212> TYPE: DNA
<213> ORGANISM: artificial sequence
<220> FEATURE:
<223> OTHER INFORMATION: Description of Artificial Sequence: SapI/EarI

<400> SEQUENCE: 1
gctcttcgcc g                                                         11

<210> SEQ ID NO 2
<211> LENGTH: 11
<212> TYPE: DNA
<213> ORGANISM: artificial sequence
<220> FEATURE:
<223> OTHER INFORMATION: Description of Artificial Sequence: SapI/EarI

<400> SEQUENCE: 2
```

```
cggcgaagag c                                                            11

<210> SEQ ID NO 3
<211> LENGTH: 11
<212> TYPE: DNA
<213> ORGANISM: artificial sequence
<220> FEATURE:
<223> OTHER INFORMATION: Description of Artificial Sequence: Sapl/Earl

<400> SEQUENCE: 3
gcccgaagag c                                                            11

<210> SEQ ID NO 4
<211> LENGTH: 11
<212> TYPE: DNA
<213> ORGANISM: artificial sequence
<220> FEATURE:
<223> OTHER INFORMATION: Description of Artificial Sequence: Sapl/Earl

<400> SEQUENCE: 4
gctcttcggg c                                                            11
```

METHOD FOR THE ASSEMBLY OF A POLYNUCLEIC ACID SEQUENCE

FIELD OF THE INVENTION

The present invention relates to a method for the assembly of a polynucleic acid sequence that is at least partially carried out on a microfluidic device. The present invention also relates to a method for the preparation of a library of polynucleic acid sequences, a microfluidic device, a method for designing nucleic acid sequences suitable for use in a method of the invention, a method for planning the assembly of a polynucleic acid sequence from a plurality of nucleic acid sequences to be carried out by a method of the invention, a system comprising means for carrying out either of said methods, a computer program which, when run on a computer, implements either of said methods and a computer readable medium or carrier signal encoding such a computer program.

BACKGROUND TO THE INVENTION

Synthetic biology brings together the disciplines of engineering, biology and bioinformatics. Its focus is to make the engineering of biology easier and more predictable. Synthetic biology could improve production methods in a wide variety of markets such as biofuels and energy, environmentally friendly chemicals, drug development and new material fabrication. It is estimated that the synthetic biology research market could be worth over $1.5 billion by 2013.

Microengineering capabilities can help to address some of the most significant challenges faced in the field. For example, the use of integrated microfluidic systems provides biologists with a powerful platform for advancing synthetic biology.

Microfluidics deals with the manipulation of minute amounts of fluid (usually micro or nanoliters) within microchannels. Biological targets can be transported in these channels for diverse manipulation. The advantages of microfluidic systems over conventional systems include reagent consumption reduction, waste reduction, cost-effectiveness and portability. Additionally, microfluidic technologies have the potential to achieve high-throughput, highly parallel biological operations. Many challenges are encountered in the fabrication of highly integrated microfluidic systems, such as the assembly of different materials and the integration of active components.

Kong et al, Nucleic Acids Res. 2007; 35(8): e61; Epub 2007 Apr. 2 and WO2007/137242 describes parallel gene synthesis in a microfluidic device. Kong et al report the fabrication of a multi-chamber microfluidic device and its use in carrying out the synthesis and amplification of several DNA constructs of up to 1 kb in length. The synthesis reactions were carried out using polymerase construction and amplification (PCA) and the products amplified by PCR. The microfluidic device was fabricated from PDMS and it was necessary to use a non-ionic surfactant, n-Dodecyl-β-D-maltoside (DDM) as a passivating agent.

Lee et al., Nucleic Acids Res. 2010; 38(8): 2514-21; Epub 2010 Feb. 21 describes a microfluidic oligonucleotide synthesizer. A PDMS-based microfluidic device was used as a miniaturized synthesizer for solid-phase parallel synthesis of oligonucleotides.

SUMMARY OF THE INVENTION

The present inventors have devised a method for the combinatorial assembly of nucleic acid sequences which overcomes the disadvantages of the prior art and have now demonstrated that ligation of nucleic acid sequences to form a polynucleic acid sequence can be carried out on a microfluidic device.

The method is a "one pot" method and is thus much quicker and more convenient to use than the hierarchical assembly approaches described in the prior art which require the nucleic acid sequences to be assembled in a pre-defined order. In addition, the method does not require the custom synthesis of nucleic acid sequences. The method makes use of oligonucleotide linkers that can be attached to any standardized nucleic acid sequence, allowing for the quick and simple assembly of polynucleic acid sequences from multiple shorter nucleic acid sequences. In contrast to methods described in the prior art, the method of the present invention does not require a polymerase and does not involve the techniques of PCR (polymerase chain reaction) or PCA (polymerase construction and amplification or polymerase cycling assembly).

In the methods described in the prior art, the nucleic acid sequences are typically prepared by PCR of a template with custom primers unique to each junction between parts, which requires the preparation of numerous primers. Moreover, PCR inherently is an error-prone operation, even with today's low error rate polymerases. Difficulties in handling repetitive sequences with fragments, or repeated copies of the same fragment also arise.

A very important feature of this technique is the ability to perform this pairing with no PCR reactions or novel oligo primers, using only pre-designed and available DNA fragments, regardless of the pairing to be performed. Thus, careful preparation of the required oligos and left-right portions of each part allows unique combinations of parts to be built with little delay, no additional oligo synthesis, and lower error rates.

In a first aspect, the present invention provides a method for the assembly of a polynucleic acid sequence from a plurality of nucleic acid sequences in which the polynucleic acid sequence is of a formula $N_{n+1}$, in which N represents a nucleic acid sequence and where n is 1 or greater than 1 and each N may be the same or a different nucleic acid sequence, in which the method comprises:
 (i) providing a first nucleic acid sequence N1 which has an oligonucleotide linker sequence $L1^{3'}$ at the 3'-end of the nucleic acid sequence;
 (ii) providing a second nucleic acid sequence N2 which optionally has an oligonucleotide linker sequence $L2^{3'}$ at the 3'-end of the nucleic acid sequence and which has an oligonucleotide linker sequence $L2^{5'}$ at the 5'-end of the nucleic acid sequence,
  wherein the 5'-end linker sequence $L2^{5'}$ of nucleic acid sequence N2 is complementary to the 3'-end linker sequence $L1^{3'}$ of nucleic acid sequence N1,
 (iii) optionally providing one or more additional nucleic acid sequences N, wherein nucleic acid sequence N2 has an oligonucleotide linker sequence $L2^{3'}$ at the 3'-end of the nucleic acid sequence, and wherein said one or more additional nucleic acid sequences N comprises a terminal additional nucleic acid sequence NZ, and wherein each additional nucleic acid sequence N has an oligonucleotide linker sequence at its 3'-end, wherein said terminal additional nucleic acid sequence NZ optionally lacks an oligonucleotide linker sequence at its 3'-end and wherein each additional nucleic acid sequence N has an oligonucleotide linker sequence at its 5'-end, wherein for the first additional nucleic acid sequence N3 the 5'-end linker sequence L3$^{5'}$ is complementary to the 3'-end linker sequence L2$^{3'}$ of nucleic acid sequence N2 and for each second and subsequent additional nucleic acid sequence N the 5'-end linker sequence is complementary to the 3'-end linker sequence of the respective preceding additional nucleic acid sequence; and (iv) ligating said nucleic acid sequences to form said polynucleic acid sequence;

wherein at least step (iv) is carried out on a microfluidic device.

DEFINITIONS

As used herein, "microfluidic device" means a device for manipulating minute amounts of fluid, usually microliters (μL or μl) or nanoliters (nL or nl). Such devices are known in the art. They are typically substantially planar and frequently contain features such as chambers, channels and/or valves. Their dimensions are typically in the region of a few cm by a few cm. Typically, when a microfluidic device contains a plurality of chambers, they are linked to each other via fluid channels which can contain valves. Microfluidic devices can be fabricated from a variety of materials, such as glass and polydimethylsiloxane (PDMS). The terms "microfluidic device", "microfluidic chip" and "microfluidic platform" are used interchangeably.

As used herein, when a method or a step of a method is described as being carried out "on chip" or "on-chip", this means that the method or a step of a method is carried out on a microfluidic device. Conversely, when a method or step of a method is described as being carried out "off chip" or "off-chip", this means that the method or step of a method is not carried out on a microfluidic device, in other words the method or step of a method is carried out away from or separately from a microfluidic device. For example, aspects of the method claimed herein can be carried out off-chip, typically using tubes and pipettes.

As used herein, the term "polynucleic acid sequence" means a polymer of nucleic acids.

As used herein, the term "nucleic acid" means a polymer of nucleotides. Nucleotides are sometimes referred to as bases (in single stranded nucleic acid molecules) or as base pairs (bp, in double stranded nucleic acid molecules). The term "nucleic acid" is used interchangeably herein with the term "part" and with the term "polynucleotide". A "nucleic acid" or "polynucleotide" as defined herein includes a plurality of oligonucleotides as defined herein.

Nucleic acids for use in the present invention are typically the naturally-occurring nucleic acids DNA or RNA, but can also be artificial nucleic acids such as PNA (peptide nucleic acid), LNA (locked nucleic acid), UNA (unlocked nucleic acid), GNA (glycol nucleic acid) and TNA (threose nucleic acid). Nucleic acids such as DNA for use in the invention can be synthetic or natural.

Nucleic acids for use in the present invention typically consist of the nucleotides adenine (A), cytosine (C), guanine (G), thymine (T) and uracil (U). Modified nucleotides that can also be used in the present invention include 4-acetylcytidine, 5-(carboxyhydroxylmethyl)uridine, 2-O-methylcytidine, 5-carboxymethylaminomethyl-2-thiouridine, 5-carboxymethylamino-methyluridine, dihydrouridine, 2-O-methylpseudouridine, 2-O-methylguanosine, inosine, N6-isopentyladenosine, 1-methyladenosine, 1-methylpseudouridine, 1-methylguanosine, 1-methylinosine, 2,2-dimethylguanosine, 2-methyladenosine, 2-methylguanosine, 3-methylcytidine, 5-methylcytidine, N6-methyladenosine, 7-methylguanosine, 5-methylaminomethyluridine, 5-methoxyaminomethyl-2-thiouridine, 5-methoxyuridine, 5-methoxycarbonylmethyl-2-thiouridine, 5-methoxycarbonylmethyluridine, 2-methylthio-N6-isopentenyladenosine, uridine-5-oxyacetic acid-methylester, uridine-5-oxyacetic acid, wybutoxosine, wybutosine, pseudouridine, queuosine, 2-thiocytidine, 5-methyl-2-thiouridine, 2-thiouridine, 4-thiouridine, 5-methyluridine, 2-O-methyl-5-methyluridine and 2-O-methyluridine.

The length of a nucleic acid sequence or polynucleotide can be measured in terms of the number of nucleotides it contains. The term "kilobase" (kb) means 1000 nucleotides.

As used herein, the term "oligonucleotide" means a polymer of nucleotides (i.e. at least 2 nucleotides) that is shorter in length than a "nucleic acid" as defined herein. The term "oligonucleotide" is sometimes abbreviated herein to "oligo". Typically, an oligonucleotide consists of up to 40 nucleotides or bases, more typically up to 60 nucleotides or bases. Typically, an oligonucleotide is sufficiently short that it has no secondary or tertiary structure.

As used herein, the terms "3'" ("3 prime") and "5'" ("5 prime") take their usual meanings in the art, i.e. to distinguish the ends of a nucleic acid molecules. As used herein, the terms 3' and 5' are also referred to using the nomenclature 5' and 3'. Nucleic molecules each have a 5' and a 3' end. Nucleic acids are synthesised in vivo in a 5' to 3' direction, and nucleic acid sequences are conventionally written in a 5' to 3' direction.

As used herein, the term "digestion" means cutting out. Typically, digestion is carried out using a restriction enzyme. For example, a restriction enzyme can be used to cut out or digest a nucleic acid sequence from a vector.

As used herein, the term "ligating" means joining together.

As used herein, the term "overhang" means a stretch of unpaired nucleotides at the end of a nucleic acid, polynucleotide or oligonucleotide.

As used herein, the term "synthetic genome" means a polynucleic acid sequence that contains the information for a functioning organism or organelle to survive and, optionally, replicate itself. The genome can be completely or partially constructed from components that have been chemically synthesized (e.g. synthetic DNA) or from copies of chemically synthesized nucleic acid components. The synthetic genome can be a completely synthetic genome, i.e. constructed entirely from nucleic acid that has been chemically synthesized, or from copies of chemically synthesized nucleic acid components. The synthetic genome can alternatively be a partially synthetic genome, i.e. constructed partially from nucleic acid that has been chemically synthesized and partially from naturally occurring nucleic acid. A partially synthetic genome as defined herein can include nucleic acid derived from any species of prokaryote or eukaryote, and/or elements from different species.

In all definitions, the singular and plural are used interchangeably.

DETAILED DESCRIPTION OF THE INVENTION

The present invention provides a method for the assembly of a polynucleic acid sequence from a plurality of nucleic acid sequences that is at least partially carried out on a microfluidic device. The method of the invention thus involves the production of a long nucleic acid sequence from a number of shorter nucleic acid sequences.

The method of the present invention is described in detail in International Patent Application No. PCT/GB2009/002917 (WO 2010/070295).

In the method of the invention, the nucleic acid sequences are assembled such that the polynucleic acid includes a plurality of nucleic acid sequences in a predetermined order. For example, the method of the invention can be used to assemble a gene or series of genes together with their associated regulatory and control elements, thus producing a complete operon. The method of the invention is thus useful in the combinatorial assembly of genetic pathways, for example metabolic pathways and synthetic pathways. In one embodiment, the method of the invention is useful in the production of a synthetic genome. For example, the method of the invention is useful for the production of a synthetic genome in a host cell such as a bacterial cell.

In the method of the present invention, the polynucleic acid sequence is of a formula $N_{n+1}$, in which N represents a nucleic acid sequence and where n is 1 or greater than 1. The method of the present invention is therefore used to produce a polynucleic acid sequence containing 2 or more nucleic acid sequences. The polynucleic acid sequence produced by the method of the present invention is not limited to a polynucleic acid sequence having a particular number of nucleic acid sequences or parts. However, the polynucleic acid sequence typically contains from 2 to 60, typically from 2 to 50, typically from 2 to 40, typically from 2 to 35, typically from 2 to 30, typically from 2 to 20, typically from 3 to 15, from 4 to 10, from 5 to 9, from 6 to 8 nucleic acid sequences. Typically, the polynucleic acid sequence contains 2, 3, 4, 5, 6, 7, 8, 9, 10, 11, 12, 13, 14, 15, 16, 17, 18, 19, 20, 25, 30, 35, 40, 45, 48, 50, 52, 54, 56, 58 or 60 nucleic acid sequences. Thus, n is typically 2, 3, 4, 5, 6, 7, 8, 9, 10, 11, 12, 13, 14, 15, 16, 17, 18, 19, 20, 25, 30, 35, 40, 45, 48, 50, 52, 54, 56, 58 or 60 and the polynucleic acid sequence produced is typically of the formula $N_2$ to $N_{10}$, i.e. the polynucleic acid sequence produced is of the formula $N_2$, $N_3$, $N_4$, $N_5$, $N_6$, $N_7$, $N_8$, $N_9$ or $N_{10}$, or alternatively the polynucleic acid sequence produced is of the formula $N_{11}$, $N_{12}$, $N_{13}$, $N_{14}$, $N_{15}$, $N_{16}$, $N_{17}$, $N_{18}$, $N_{19}$, $N_{20}$, $N_{25}$, $N_{30}$, $N_{35}$, $N_{40}$, $N_{45}$, $N_{48}$, $N_{50}$, $N_{52}$, $N_{54}$, $N_{56}$, $N_{58}$ or $N_{60}$.

The polynucleic acid produced by the method of the present invention typically comprises at least 1000 nucleotides. Typically, the polynucleic acid produced by the method of the present invention comprises between 1000 and 50000 nucleotides, typically between 2000 and 40000 nucleotides, typically between 3000 and 30000 nucleotides, typically between 4000 and 25000 nucleotides, typically between 5000 and 20000 nucleotides, typically between 6000 and 15000 nucleotides, typically between 7000 and 13000 nucleotides, typically between 8000 and 12000 nucleotides, typically between 9000 and 11000 nucleotides, typically around 10000 nucleotides. Typically, the polynucleic acid sequence is from 10 kb to 30 kb. However, the polynucleic acid can be from 10 kb to 30 kb, 40 kb, 50 kb, 75 kb, 100 kb, 120 kb, 140 kb or 150 kb. In some embodiments, the polynucleic acid is at least 150 kb, at least 200 kb, at least 250 kb, at least 300 kb, at least 350 kb, at least 400 kb, at least 450 kb or at least 500 kb in length.

The method of the invention can be used to obtain a plurality of polynucleic acid sequences. For example, the method of the invention can be carried out multiple times in parallel, with the result being a plurality of polynucleic acid sequences. The polynucleic acid sequences obtained by carrying out the method of the invention multiple times can then be joined together into a longer polynucleic acid sequence, for example using the method of the present invention but where N represents a polynucleic acid sequence rather than a nucleic acid sequence. This method can therefore be used to produce longer polynucleic acid sequences.

In the method of the invention, each N may be the same or a different nucleic acid sequence. The method of the invention can therefore be used for the combinatorial assembly of the same or different nucleic acid sequences. Typically, each N is a different nucleic acid sequence. However, the method of the invention can also be used to produce a polynucleic acid sequence comprising a number of nucleic acids which are the same, for example to increase the copy number of a protein-coding sequence. This embodiment of the invention is useful in the preparation of a combinatorial library of nucleic acid sequences as described herein.

The nucleic acid sequences used in the present invention can be coding or non-coding sequences. Typically, each nucleic acid sequence used in the present invention is a protein coding sequence or a regulatory or control element.

The nucleic acid sequences used in the present invention can be obtained from any suitable source. For example, the nucleic acid sequences can be synthesised for use in the invention or can be obtained from a natural source. Conveniently, the nucleic acid sequences used in the present invention can be sourced from the BioBricks™ registry of standard parts (Cambridge, Mass.; partsregistry.org). BioBricks™ parts are nucleic acids of defined structure and function. The method of the present invention can therefore be used to assemble existing BioBricks™ parts available from the BioBricks™ registry of standard parts.

Protein coding sequences for use in the present invention include sequences that encode proteins that are part of metabolic or other genetic pathways. Protein coding sequences for use in the present invention also include sequences that encode experimentally useful proteins, such as reporter proteins. Suitable reporter proteins for use in the present invention include coloured proteins such as lacZa, fluorescent proteins such as RFP or GFP, and proteins that confer antibiotic resistance. Reporter genes are linked to a test promoter, enabling activity of the promoter gene to be determined by detecting the presence of the reporter gene product.

For example, the method of the invention can be used to produce a DNA assembly in which a ribosome binding site (RBS) is inserted between a transcriptional promoter and a reporter protein, for example lacZa or mRFP1. Proper insertion of this RBS results in a complete operon for expression of the reporter protein, resulting in a phenotypic change.

Regulatory or control elements for use in the present invention include promoters, operators, repressors, ribosome-binding sites, internal ribosome entry sites (IRESs) origins of replication, enhancers, polyadenylation regions, splice donor and acceptor sites, transcriptional termination sequences, 3' UTRs and 5' UTRs.

Promoters are regions of DNA that facilitate the transcription of a particular gene by including a binding site for RNA polymerase. Promoters typically lie upstream of the gene whose transcription they control. Promoters for use in the invention include constitutive and inducible promoters.

In a first step (i), the method of the present invention comprises providing a first nucleic acid sequence N1 which has an oligonucleotide linker sequence $L1^{3'}$ at the 3'-end of the nucleic acid sequence.

In one embodiment of the invention, the first nucleic acid sequence N1 also has an oligonucleotide linker sequence $L1^{5'}$ at the 5'-end of the nucleic acid sequence.

In a second step (ii), the method of the present invention comprises providing a second nucleic acid sequence N2 which optionally has an oligonucleotide linker sequence $L2^{3'}$ at the 3'-end of the nucleic acid sequence and which has an oligonucleotide linker sequence $L2^{5'}$ at the 5'-end of the nucleic acid sequence, wherein the 5'-end linker sequence $L2^{5'}$ of nucleic acid sequence N2 is complementary to the 3'-end linker sequence $L1^{3'}$ of nucleic acid sequence N1. The second nucleic acid sequence N2 therefore has an oligonucleotide linker sequence $L2^{5'}$ at its 5'-end, and optionally also has an oligonucleotide linker sequence $L2^{3'}$ at the 3'-end of the nucleic acid sequence.

In one embodiment of the invention, the second nucleic acid sequence N2 also has an oligonucleotide linker sequence $L2^{3'}$ at the 3'-end of the nucleic acid sequence. For example, the second nucleic acid sequence N2 has an oligonucleotide linker sequence $L2^{3'}$ at the 3'-end of the nucleic acid sequence in the embodiment where the polynucleic acid sequence is of the formula $N_{\geq 3}$, i.e. wherein the polynucleic acid sequence is comprised of 3 or more nucleic acid sequences N.

The third step (iii) of the method of the present invention is optional. The third step (iii) of the method of the invention is present in the embodiment where the polynucleic acid sequence is of the formula $N_{\geq 3}$, i.e. wherein the polynucleic acid sequence is comprised of 3 or more nucleic acid sequences N.

Thus in one embodiment of the invention, in which step (iii) of the method of the invention is not present, the method of the present invention comprises:

(a) providing a first nucleic acid sequence N1 which has an oligonucleotide linker sequence $L1^{3'}$ at the 3'-end of the nucleic acid sequence;

(b) providing a second nucleic acid sequence N2 which has an oligonucleotide linker sequence $L2^{5'}$ at the 5'-end of the nucleic acid sequence, wherein the 5'-end linker sequence $L2^{5'}$ of nucleic acid sequence N2 is complementary to the 3'-end linker sequence $L1^{3'}$ of nucleic acid sequence N1; and (c) ligating said nucleic acid sequences to form said polynucleic acid sequence;

wherein at least step (c) is carried out on a microfluidic device.

In this embodiment of the invention, the polynucleic acid sequence is of the formula $N_2$, i.e. the polynucleic acid sequence is comprised of 2 nucleic acid sequences, N1 and N2.

In some embodiments, the first nucleic acid sequence N1 also has an oligonucleotide linker sequence $L1^{5'}$ at the 5'-end of the nucleic acid sequence. In some embodiments, the second nucleic acid sequence N2 also has an oligonucleotide linker sequence $L2^{3'}$ at the 3'-end of the nucleic acid sequence. In some embodiments, the 5'-end linker sequence $L1^{5'}$ of nucleic acid sequence N1 is complementary to the 3'-end linker sequence $L2^{3'}$ of nucleic acid sequence N2. In this embodiment of the invention, the nucleic acid is circular, and is typically circular DNA.

In the optional third step (iii), the method of the present invention comprises providing one or more additional nucleic acid sequences N, wherein nucleic acid sequence N2 has an oligonucleotide linker sequence $L2^{3'}$ at the 3'-end of the nucleic acid sequence, and wherein said one or more additional nucleic acid sequences N comprises a terminal additional nucleic acid sequence NZ, and wherein each additional nucleic acid sequence N has an oligonucleotide linker sequence at its 3'-end, wherein said terminal additional nucleic acid sequence NZ optionally lacks an oligonucleotide linker sequence at its 3'-end and wherein each additional nucleic acid sequence N has an oligonucleotide linker sequence at its 5'-end, wherein for the first additional nucleic acid sequence N3 the 5'-end linker sequence $L3^{5'}$ is complementary to the 3'-end linker sequence $L2^{3'}$ of nucleic acid sequence N2 and for each second and subsequent additional nucleic acid sequence N the 5'-end linker sequence is complementary to the 3'-end linker sequence of the respective preceding additional nucleic acid sequence.

In step (iii), the 5'-end linker sequence of each second and subsequent additional nucleic acid sequence N is complementary to the 3'-end linker sequence of the respective preceding additional nucleic acid sequence. In other words, $Li^{5'}$ is complementary to $L(i-1)^{3'}$.

In some embodiments, the first nucleic acid sequence N1 also has an oligonucleotide linker sequence $L1^{5'}$ at the 5'-end of the nucleic acid sequence. In some embodiments, the terminal additional nucleic acid sequence NZ also has an oligonucleotide linker sequence $LZ^{3'}$ at the 3'-end of the nucleic acid sequence. In some embodiments, the 5'-end linker sequence $L1^{5'}$ of nucleic acid sequence N1 is complementary to the 3'-end linker sequence $LZ^{3'}$ of nucleic acid sequence NZ. In this embodiment of the invention, the nucleic acid is circular, and is typically circular DNA.

In one embodiment of the invention, the method of the present invention comprises:

(i) providing a first nucleic acid sequence N1 which has an oligonucleotide linker sequence $L1^{3'}$ at the 3'-end of the nucleic acid sequence;

(ii) providing a second nucleic acid sequence N2 which has an oligonucleotide linker sequence $L2^{3'}$ at the 3'-end of the nucleic acid sequence and which has an oligonucleotide linker sequence $L2^{5'}$ at the 5'-end of the nucleic acid sequence, wherein the 5'-end linker sequence $L2^{5'}$ of nucleic acid sequence N2 is complementary to the 3'-end linker sequence $L1^{3'}$ of nucleic acid sequence N1;

(iii) providing a third nucleic acid sequence N3 which has an oligonucleotide linker sequence $L3^{5'}$ at the 5'-end of the nucleic acid sequence, wherein the 5'-end linker sequence $L3^{5'}$ of nucleic acid sequence N3 is complementary to the 3'-end linker sequence $L2^{3'}$ of nucleic acid sequence N2; and (iv) ligating said nucleic acid sequences to form said polynucleic acid sequence;

wherein at least step (iv) is carried out on a microfluidic device.

In this embodiment of the invention, the polynucleic acid sequence is of the formula $N_3$, i.e. the polynucleic acid sequence is comprised of 3 nucleic acid sequences, N1, N2 and N3.

In some embodiments, the first nucleic acid sequence N1 also has an oligonucleotide linker sequence $L1^{5'}$ at the 5'-end of the nucleic acid sequence. In some embodiments, the third nucleic acid sequence N3 also has an oligonucleotide linker sequence $L3^{3'}$ at the 3'-end of the nucleic acid sequence. In some embodiments, the 5'-end linker sequence $L1^{5'}$ of nucleic acid sequence N1 is complementary to the 3'-end linker sequence $L3^{3'}$ of nucleic acid sequence N3. In this embodiment of the invention, the nucleic acid is circular, and is typically circular DNA.

In a fourth step (iv), the method of the present invention comprises ligating said nucleic acid sequences to form said polynucleic acid sequence. At least step (iv) of the method of the invention is carried out on a microfluidic device.

Typically, step (iv) of the method of the invention is carried out using DNA ligase. DNA ligase is an enzyme that links together two DNA strands that have a double-stranded break. Any type of commercially available DNA ligase can be used in the present invention, for example T4 DNA ligase available from New England Biolabs, MA. Any of the mammalian DNA ligases (DNA ligase I, DNA ligase II, DNA ligase III, DNA ligase IV) can be used in the present invention. Step (iv) of the method of the invention can alternatively be carried out using RNA ligase.

In some embodiments, step (iv) of the method of the invention is carried out without using a ligase. For example, in one embodiment, step (iv) of the method of the invention is carried out using chemical ligation. Any suitable method for carrying out chemical ligation can be used, for example using cyanogen bromide as a condensing agent or using hydrogen peroxide.

In one embodiment of the invention, the nucleic acid sequences N together with their oligonucleotide linker sequences are purified immediately prior to step (iv). Any suitable method can be used to purify the nucleic acid sequences. By "purifying the nucleic acid sequences" is meant removing any unbound oligonucleotide linker sequences (also referred to herein as part/linker oligos).

Purification can be carried out in a number of separate steps, for example two separate steps as illustrated in FIGS. 9 and 10. In one embodiment, a first purification step is carried out to remove unbound oligonucleotide linker sequences that bind to the 3'-end of a nucleic acid sequence and a second step is carried out to remove unbound oligonucleotide linker sequences that bind to the 5'-end of a nucleic acid sequence. In some embodiments, a number of different purification steps will be needed, typically one per oligonucleotide linker sequence attached to the nucleic acid sequences to be assembled using the method of the invention.

As set out above, at least step (iv) of the method of the invention is carried out on a microfluidic device. The step of purifying the nucleic acid sequences immediately prior to step (iv) can either be carried out on-chip or off-chip (as defined herein).

Thus, in one embodiment, the nucleic acid sequences are purified on the microfluidic device. In this embodiment, the nucleic acid sequences are typically purified by biotin-based methods such as biotin-streptavidin purification, for example biotin-streptavidin purification using streptavidin-coated beads, typically streptavidin-coated magnetic beads. Such beads are of a size suitable for use in a microfluidic device as described herein, and so the diameter of such beads will be in the nm or µm range, for example from 500 nm to 5 µm, from 700 nm to 4 µm, from 800 nm to 3 µm, from 900 nm to 2 µm or around 1 µm.

The nucleic acid sequences can be purified on the same microfluidic device on which step (iv) is carried out or alternatively the purification step and the ligation step (iv) can be carried out on separate microfluidic devices. In one embodiment, purification is carried out using one or more microfluidic devices prior to ligation step (iv) being carried out on a different microfluidic device. Purification of multiple nucleic acid sequences can be carried out simultaneously either on one microfluidic device or on a plurality of microfluidic devices, which may or may not be linked to the microfluidic device on which the ligation step is carried out.

In one embodiment, the nucleic acid sequences are purified by biotin-streptavidin purification, for example as shown in FIG. 11. This purification approach targets a specific DNA sequence by annealing DNA to a biotinylated oligo. This purification approach utilizes a biotinylated oligo that is complementary to an overhang on the part-linker pair or the pathway assembly. The oligo anneals to the DNA fragment and then the pair is washed over streptavidin-coated beads. These beads can be magnetic or otherwise easily purified from solution. This purification approach was used in Example 1 herein.

In an alternative embodiment, the nucleic acid sequences are purified off-chip, as defined herein. In other words, purification does not take place on the microfluidic device. In this embodiment, the nucleic acid sequences are typically purified using DNA purification spin columns or gel extraction. For example, the part-linker pairs can be purified using the QiaQuick™ PCR purification kit (Qiagen™) or via gel electrophoresis and extraction via the QiaQuick™ gel extraction kit (Qiagen™). Gel-based purification was used in Example 4 herein. Many other suitable methods of purifying nucleic acid sequences will be known to the skilled person and can be used in the present invention, for example high performance liquid chromatography (HPLC) and nuclease treatment that selectively destroys unbound oligonucleotides.

Once the method of the invention has been carried out to produce the polynucleic acid sequence, the polynucleic acid sequence can be transformed into suitable cells to verify that the assembly has been successful. Suitable cells include chemically competent *E. coli* (available from Invitrogen, CA or New England Biolabs, MA). The successful assembly can then be verified, e.g. by plating out the cells and counting coloured/colourless colonies, for example by counting red or green colonies as described in Example 1 herein.

In one embodiment of the invention, each of the nucleic acid sequences N is provided with an overhang at one or both ends. In some embodiments, the nucleic acid sequences N have an overhang only at one end, either the 3'-end or the 5'-end. Typically, each nucleic acid sequence N has an overhang at both the 3'-end and the 5'-end. This embodiment of the invention is illustrated in FIGS. 6 and 7.

Typically, the overhang at one or both ends of each nucleic acid sequence is produced by digestion with one or more restriction enzymes. For example, in some embodiments of the invention one or more of the nucleic acid sequences is stored in a vector prior to use in the method of the invention, as shown in FIGS. 6 and 7. Typically, BioBricks™ parts, i.e. nucleic acids from the BioBricks™ registry (Cambridge, Mass.), are stored in this fashion. In this embodiment, a restriction enzyme is used to cut the nucleic acid sequence out from the vector in which it is stored before use in the method of the invention.

The overhang at one or both ends of the nucleic acid sequence can be palindromic or non-palindromic.

Any restriction enzyme can be used in the present invention. Suitable restriction enzymes for use in the invention include restriction enzymes that produce single-stranded overhangs. Typical restriction enzymes for use in the present invention are Type IIS restriction enzymes, which cleave at sites away from their recognition site.

Suitable restriction enzymes for use in the invention include EcoRI, SpeI, SapI, EarI and PstI. The restriction enzyme is typically EarI.

In one embodiment, in which the nucleic acid sequence has an overhang at both ends, the overhang at the 5'-end of the nucleic acid sequence can be produced by digestion with EcoRI and the overhang at the 3'-end of the nucleic acid sequence can be produced by digestion with SpeI. The overhangs produced by EcoRI and SpeI are palindromic. EcoRI and SpeI are typically used in this fashion to prepare BioBricks™ parts, i.e. nucleic acids from the BioBricks™ registry, and leave standard overhangs at the 5'-end and the 3'-end of the nucleic acid sequence.

In another embodiment, the overhang at the 5'-end of the nucleic acid sequence or at the 3'-end of the nucleic acid sequence can be produced by digestion with SapI or EarI. The overhangs produced by SapI and EarI are non-palindromic.

The overhangs produced by EcoRI/SpeI and SapI/EarI are shown diagrammatically in FIG. 8.

The overhangs on each nucleic acid sequence N are typically produced by digestion with the same restriction enzyme or combination of restriction enzymes. Alternatively, the overhangs on different nucleic acid sequences N can be produced using different restriction enzymes or combinations of restriction enzymes. For example, one nucleic acid sequence N can be designed to be cut by EcoRI/SpeI and another nucleic acid sequence N can be designed to be cut by EcoRI/PstI. However, in either of these embodiments, there will typically be one standard overhang on each of the nucleic acid sequences.

In one embodiment, the overhang is 3 or 4 nucleotides in length. However, the overhang can be of a different length, for example 2 nucleotides or 5, 6, 7, 8, 9 or 10 nucleotides in length.

In one embodiment, the overhang at the 3'-end of the nucleic acid sequence is the same for each nucleic acid sequence. In another embodiment, the overhang at the 5'-end of the nucleic acid sequence is the same for each nucleic acid sequence. In another embodiment, the overhang at the 3'-end of the nucleic acid sequence and the overhang at the 5'-end of the nucleic acid sequence is the same for each nucleic acid sequence. The overhang can therefore be the same or different at each end of the nucleic acid sequence.

In the embodiment in which the overhang at the 3'-end of the nucleic acid sequence or at the 5'-end of the nucleic acid sequence is the same for each nucleic acid sequence, the nucleic acid sequences can be designed such that the same overhang is produced after restriction digest, i.e. after digestion with a restriction enzyme.

In one embodiment, the present invention encompasses a library of nucleic acid sequences with appropriate overhangs ready for use in the invention.

Each nucleic acid sequence used in the method of the present invention has an oligonucleotide linker sequence at the 3'-end, at the 5'-end or at both the 3'-end and the 5'-end of the nucleic acid sequence, as described herein.

In one embodiment, the present invention encompasses a library of nucleic acid sequences together with appropriate oligonucleotide linker sequences ready for use in the invention.

The oligonucleotide linker sequences used in the present invention are typically double stranded. Typically, the oligonucleotide linker sequences are partially double stranded. That is to say, each of the 3'-end linker sequences and each of the 5'-end linker sequences used in the method of the present invention is typically partially double stranded. By "partially double stranded" is meant that either the 3'-end or the 5'-end of the linker sequence or both has an overhang. In this embodiment, each of the two strands of the 3'-end linker sequences and the 5'-end linker sequences have different numbers of nucleotides. The result of this is that each of the linker sequences has an overhang. The linker sequences can therefore be considered as being comprised of two separate single stranded oligonucleotide sequences of different lengths, with the result being that the linker sequences are partially double stranded and have one or more overhangs. This embodiment of the invention is illustrated in FIGS. 6 and 7.

In some embodiments of the invention, the overhang at one end of the nucleic acid sequence is complementary to the overhang on the 3'-end linker sequence and/or to the overhang on the 5'-end linker sequence. This embodiment of the invention is also illustrated in FIGS. 6 and 7. In these embodiments of the invention, each of the nucleic acid sequences used in the method of the invention is attached to its said 3'-end linker sequence and to its said 5'-end linker sequence by oligonucleotide annealing and ligation. In some embodiments, where the nucleic acid is DNA, ligation is carried out using DNA ligase.

Typically, one or more of the nucleic acid sequences is attached to its 3'-end linker sequence and/or to its 5'-end linker sequence by ligation. More typically, each of the nucleic acid sequences is attached to its 3'-end linker sequence and to its 5'-end linker sequence by ligation. Typically, ligation is carried out using a ligase, typically DNA ligase.

In some embodiments, the oligonucleotide linker sequences used in the present invention are single stranded.

In some embodiments, the nucleic acid sequences are provided in a vector and are cut out or digested from the vector using a restriction enzyme.

Accordingly, in one embodiment, the present invention provides a method for the assembly of a polynucleic acid sequence from a plurality of nucleic acid sequences in which the polynucleic acid sequence is of a formula $N_{n+1}$, in which N represents a nucleic acid sequence and where n is 1 or greater than 1 and each N may be the same or a different nucleic acid sequence, in which the method comprises:

(i) providing a first nucleic acid sequence N1 in a vector, using a restriction enzyme to cut the nucleic acid sequence out from the vector and ligating an oligonucleotide linker sequence $L1^{3'}$ to the 3'-end of the nucleic acid sequence;

(ii) providing a second nucleic acid sequence N2 in a vector, using a restriction enzyme to cut the nucleic acid sequence out from the vector, optionally ligating an oligonucleotide linker sequence $L2^{3'}$ to the 3'-end of the nucleic acid sequence and ligating an oligonucleotide linker sequence $L2^{5'}$ to the 5'-end of the nucleic acid sequence, wherein the 5'-end linker sequence $L2^{5'}$ of nucleic acid sequence N2 is complementary to the 3'-end linker sequence $L1^{3'}$ of nucleic acid sequence N1;

(iii) optionally providing one or more additional nucleic acid sequence(s) N in one or more vector(s), using a restriction enzyme to cut the nucleic acid sequence(s) out from the vector(s), wherein nucleic acid sequence N2 has an oligonucleotide linker sequence $L2^{3'}$ at the 3'-end of the nucleic acid sequence, and wherein said one or more additional nucleic acid sequences N comprises a terminal additional nucleic acid sequence NZ, and ligating an oligonucleotide linker sequence to the 3'-end of each additional nucleic acid sequence N, wherein said terminal additional nucleic acid sequence NZ optionally lacks an oligonucleotide linker sequence at its 3'-end, and ligating an oligonucleotide linker sequence to the 5'-end of each additional nucleic acid sequence N, wherein for the first additional nucleic acid sequence N3 the 5'-end linker sequence L3$^{5'}$ is complementary to the 3'-end linker sequence L2$^{3'}$ of nucleic acid sequence N2 and for each second and subsequent additional nucleic acid sequence N the 5'-end linker sequence is complementary to the 3'-end linker sequence of the respective preceding additional nucleic acid sequence; and (iv) ligating said nucleic acid sequences to form said polynucleic acid sequence;

wherein at least step (iv) is carried out on a microfluidic device.

In one embodiment, the digestion and ligation steps are carried out in two separate reactions. Alternatively, the digestion and ligation steps can be combined in a single reaction.

Typically, when the digestion and ligation steps are combined, the reaction is carried out by alternating between the digestion and the ligation step. This is typically done by alternating between temperatures suitable for digestion and ligation, typically multiple times. For example, the reaction can be carried out by alternating at least 1, 2, 3, 4, 5 or 6 times between a temperature suitable for digestion and a temperature suitable for ligation. For example, the reaction can be carried out under conditions in which the temperature is alternated 2, 3, 4, 5 or 6 times between a temperature expected to be optimal for digest activity (for example from 30° C. to 40° C., typically from 33° C. to 39° C., more typically from 37° C. to 38° C., more typically 37° C.) and a temperature expected to be near optimal for ligation activity (for example from 12° C. to 19° C., typically from 13° C. to 18° C., more typically from 15° C. to 17° C., more typically 16° C.). This embodiment of the invention is typically carried out using a thermocycle. This embodiment is illustrated in Example 4 herein and in FIG. 44.

This embodiment of the invention has a number of advantages, including making downstream purification easier, saving on oligo costs, and shortening the assembly process. Combining the digestion and ligation reactions means that much less of the ligation oligos needs to be used, as any incorrect re-ligations will be re-digested by the restriction enzyme in the next cycle. This makes the downstream purification easier as there are fewer contaminating oligos. Running a single reaction simplifies the entire process by reducing a step and also increases the purification efficiency.

One embodiment of the present invention is as follows.

The approach described here enables the assembly of many different pathways from a small collection of standard parts by assembling multiple parts in a single reaction step. Unlike similar "one pot" assembly approaches conducted previously, this approach requires neither synthesis of custom oligos for assembly nor that parts be assembled in a pre-defined order. By standardizing parts, it is possible to expend effort once to prepare components and then reuse them to generate many pathways in a rapid, highly parallelizable reaction.

This assembly process involves three phases: part preparation, part-linker fusion, and pathway assembly (see FIG. 1).

The part preparation is outside of the assembly cycle. Extra work is put into the design and preparation of parts in order to reduce the time required for assembly (see FIG. 2).

All parts can be stored in plasmids such that they can be cut out in a standard form. The offset cutter SapI is used as an example through this description, but this approach is by no means limited by the particular enzyme. SapI recognizes a 7 bp sequence and leaves a 3 bp overhang that can be anything. Parts are designed to be cut out by digestion with SapI, leaving 3 bp overhangs on both ends. The 3 bp overhang on the 3'-end of the part is defined to be a standard 3 bp sequence common for all parts in this format. The 3 bp overhang on the 5'-end of the part is defined to be something other than this standard 3 bp sequence. The part sequences are all defined to not contain any extra recognition sites for SapI.

Parts are split into two regions: a short beginning region and the rest of the part. The beginning region (approximately 10 bp) is defined by oligos. The remainder of the part is stored in a plasmid as described above. When the plasmid is cut, the truncated part is released. Upon ligation with the oligos, the part is reconstituted except for an overhang on the front (e.g. 10 bp).

The process for preparing part A with defined overhangs involves:
1. Cutting the plasmid prep with SapI
2. Ligate oligos $1_A$ and $2_A$ (both 5'-phosphorylated) to the cut part
3. Also, add biotinylated oligo $5_A$ which binds to the ligation product via non-covalent base pairing (e.g. 10 bp)
4. The complex is purified via the biotin (e.g. using magnetic streptavidin beads)
5. The purified, ligated product is released by heating to break the pairing with the biotin oligo
6. Oligos $3_A$ and $4_A$ are synthesized during the construction of part A and stored in annealed form for use during the assembly Note that there may be other ways of obtaining the same final DNA structure, such as de novo DNA synthesis or PCR methods (e.g. the New England Biolabs USER™ (Uracil-Specific Excision Reagent) system). The prepared parts that are output and stored from this phase include the complete part except for a long overhang (e.g. 10 bp) on one side and a 3 bp overhang on the other side. The short 3 bp overhang is a standard sequence and the long overhang sequence is from the part.

Designing parts in this format needs to be done once. After standardization, parts can then be reused in as many different assemblies as desired. Prepared parts are stored, along with the helper oligos, and serve as input to the assembly phases. The same part oligos can be used for all assemblies using the part. Purification and quality control during part preparation and storage ensures that the inputs to the assembly process are of the highest quality.

Note that the above description assumes that the 3 bp overhang at the end of the part is standardized. A substantially identical process is possible by standardizing the 3 bp overhang at the beginning of a part and defining oligos to complete the end of a part. The assembly process in either case is similar.

The long overhang after part preparation can be designed to form either a 5'- or 3'-overhang, unlike many other assembly methods. In addition, it is possible to mix and match both types of overhangs in an assembly without needing to know beforehand which parts will be assembled. A smart part design process would use different types of overhangs to maximize the number of parts that can be assembled in one pot.

Also described herein is the computer aided design (CAD) tools used to design the parts. The design of a part starts with the initial DNA sequence for a part, call it part A. This sequence is required to not include the recognition sequence for SapI (or any other enzyme used), in either orientation. If required, the CAD system designs oligos and a mutation strategy, such as the Quikchange mutagenesis (Stratagene) to remove these sites. This process takes into account the properties and use of the sequence, preferring silent mutations in coding regions, for example.

A (potentially modified) sequence for the complete part A is then available. In a second step, this sequence is analyzed to locate an appropriate place to truncate part A into two parts: (1) the left most part, which will be created by the reverse complement of oligo $2_A$, (2) a truncated portion of part A, which consists of the remainder of part A. There are several considerations used by the program to locate the position of this split. (a) The three base overhang created at the left end of the truncated part A must satisfy several requirements. It must not be identical to the standard overhang forming the three base scar at the right end of every part. It must have an appropriate melting temperature, such that the ligation of annealed oligos $1_A$ and $2_A$ can be carried out efficiently. Typically, this would require a minimal GC content in the overhang. The length and melting temperature of oligo $1_A$ must be sufficient to stabilize the $1_A$ and $2_A$ annealed double strand together at the ligation temperature. The overlap of oligo $5_A$ with oligo $2_A$ must be sufficiently long and have a high enough melting temperature to stabilize the double stranded structure formed at the ligation temperature. This overlap must be sufficiently short and have low enough melting temperature to be disassociable during biotin purification of part A. The output of the algorithm is then the location of the split between the truncated part A and oligo $2_A$. This split location also determines the three base overhang at the left end of part A and the length of oligo $2_A$. The second output of the algorithm is the length of oligo $1_A$, which also determines the length of oligo $5_A$. Oligos $3_A$ and $4_A$ are then easily defined using the sequences of oligos $5_A$ and $2_A$.

The lengths of oligos $1_A$, $2_A$, and $5_A$ are determined using standard search techniques within the sequence A. It is possible that this search will fail to yield good sequences, and may require redesign of the part to satisfy the assembly process, but this is a rare event.

Another output of the algorithm is the pair of PCR primers necessary to amplify the truncated part A, including the SapI cut sites at both ends, and the three by unique left overhang, and the standard three by overhang on the right end.

In the part-linker fusion phase, parts are processed into assembly-ready parts (FIG. 3). Although assembly-ready parts depend on the desired assembly, assembly-ready parts can likely be reused in many pathway assemblies. The reactions in this phase are highly parallel and can be done in constant time (e.g. the time to assemble the pathway is independent of the number of parts contained in the pathway).

One reaction is done for every part junction that is desired. Biotin-based purification is described here, but other means of purification are of course also possible. For example, if part A and part B need to be assembled in some pathway, then the following process is performed:

1. Ligate to the prepared part A the annealed oligos $3_B$ and $4_B$ that were constructed during the part preparation phase of part B
2. The oligos for B form the standard 3 bp overhang and thus can ligate with A easily
3. $4_B$ is designed to not ligate with part A. For example, $4_B$ may have a 3'-dideoxy nucleotide or may be "missing" a base at the 3'-end
4. For purifying the correctly ligated product, $4_B$ is biotinylated
5. The complex is purified via the biotin (e.g. using magnetic streptavidin beads)
6. The purified, ligated product is released by heating to break the pairing with the biotin oligo The above process will create a molecule that contains the entirety of part A, followed by a 3 nt standard "scar" sequence, and then followed by the initial sequence of part B. We will refer to this fusion molecule as $A_B$. Both ends of this molecule will contain long overhangs matching the beginning of part A and the beginning of part B. One can imagine a scarless version of this fusion process. For example, if the 3 nt overhang were chewed back (e.g. via a nuclease) and a blunt ligation done, then the scar would disappear. We will assume for simplicity in this description that a 3 nt scar will appear between assembled parts.

The final phase is the assembly of the complete desired pathways using in vitro ligation. The process for this phase is extremely simple (FIGS. 4 and 5). As the overhangs should all match perfectly, only ligase is required in this reaction. Assume that parts A, B, Y, and Z are being assembled to form a linear DNA. Suppose parts A and Z are standard parts added at the beginning and end of all assemblies, and thus not necessarily a part of the desired pathway.

1. All of the part-linker fusions of $A_B$, $B_C$, . . . , $Y_Z$ generated from the previous step are mixed together
2. DNA ligase is added
3. Add the biotinylated oligo $5_A$ that base pairs to the front overhang of A
4. Pull out the biotin using magnetic streptavidin beads effectively purifying away anything that does not begin with part A
5. Purify away the biotinylated oligo $5_A$ by heating to break the base pairing
6. Add the biotinylated oligo $4_Z$ which base pairs to the overhang of Y
7. Pull out the biotin using magnetic streptavidin beads effectively purifying away anything that does not end with part Y
8. Purify away the biotinylated oligo $4_A$ by heating to break the base pairing
9. The biotinylated oligo is purified away by heating to break the base pairing The resulting purified fragment will contain the assembly of parts A . . . $Y_Z$. Complete dsDNA is present for the desired assembly of parts B . . . Y. Extra overhangs are present on the ends which can be blunted with a nuclease if so desired. If a circular DNA is desired, one can add a final ligation step with $Z_A$ which will complete the circle. For example, this circular DNA can then be cloned into bacteria for propagation.

The time required for the pathway assembly phase depends on the nature of the pathways to be assembled. For a subset of the parts (i.e. parts that don't have matching overhang sequences), this phase can be done in constant time, independent of the size of the pathways to be assembled. However, if some parts have matching overhangs (e.g. if a part is used multiple times in the assembly), this assembly process needs to be broken into multiple cycles such that the offending parts are assembled in different reactions before being combined.

The output of the assembly process is the purified, assembled pathway. Ultimately, sequencing will not be necessary due to the stringent quality control used during part preparation and the purification during the process. The purifications are described using biotin/streptavidin purification steps. However, other methods such as length-based (e.g. gel electrophoresis) can also be substituted.

It is possible for an assembled pathway to be used as a new part via idempotent assembly. If one wishes to use the assembly process to produce a plasmid that can itself be used as a part (i.e. contains the correct placement of SapI sites), a couple of small changes need to be made. During the part preparation phase for the first part (A), a different set of oligos that add back a SapI site instead of reconstituting part A should be used. The last part during the assembly (Z) should also contain a SapI site in the proper location. All other aspects of the assembly can remain the same.

In one embodiment, the present invention provides a method for the assembly of a polynucleic acid sequence as shown in FIG. 6.

In the part cloning phase, a part (in this case Part A) is prepared by carrying out PCR using a forward primer ($A_F$) and a reverse primer ($A_R$). The part is designed to be in a standard form, with a standard overhang at the 3'-end ($S_L$) and a standard overhang at the 5'-end ($S_P$), each of which is designed to be recognised by a particular restriction enzyme. Conveniently, the part can be cloned into a plasmid for storage before carrying out the part preparation phase.

In the part preparation phase, the plasmid containing the part is digested with one or more restriction enzymes that recognises and cuts the part at a predefined sequence, leaving standard overhangs at the 3'-end ($S_L$) and at the 5'-end ($S_P$) of the part.

In the part/linker assembly phase, the part (in this case Part A) is ligated and purified using one set of standard part oligos. These oligos bind at the 5'-end of the part. The standard part oligos include a partially double stranded linker oligonucleotide that consists of a shorter oligonucleotide ($X^1_{P2}$) that binds to the overhang $S_P$ at the 5'-end of the part and a longer oligonucleotide ($X^1_{P1}$) that binds directly to the 5'-end of the part on the strand which does not have the overhang. $X^1_{P2}$ is complementary to $X^1_{P1}$ and since $X^1_{P1}$ is longer than $X^1_{P2}$ a new overhang is created at the 5'-end of the part.

The standard part oligos also include a part purification oligo ($X^1_{PP}$) that binds to $X^1_{P2}$ and is partially complementary to $X^1_{P1}$ in the new region of overhang created when $X^1_{P2}$ binds to $X^1_{P1}$. The part purification oligo ($X^1_{PP}$) is used to purify Part A. The part purification oligo ($X^1_{PP}$) is then removed by melting, leaving the part (Part A) with the linker oligonucleotide consisting of $X^1_{P2}$ and $X^1_{P1}$ attached.

Meanwhile, Part Z, which will bind to the 5'-end of Part A, is prepared in a similar manner to Part A. Part Z also has standard overhangs at the 3'-end ($S_L$) and at the 5'-end ($S_P$) of the part.

In the part/linker assembly phase, the part (in this case Part Z) is ligated and purified using one set of standard linker oligos. These oligos bind at the 3'-end of the part. The standard linker oligos include a partially double stranded linker oligonucleotide that consists of a shorter oligonucleotide ($X^1_{L2}$) that binds to the overhang $S_L$ at the 3'-end of the part and a longer oligonucleotide ($X^1_{L1}$) that binds directly to the 3'-end of the part on the strand which does not have the overhang. $X^1_{L2}$ is complementary to $X^1_{L1}$ and since $X^1_{L1}$ is longer than $X^1_{L2}$ a new overhang is created at the 3'-end of the part. This overhang is complementary to the overhang at the 5'-end of Part A that is formed from $X^1_{P1}$ The standard linker oligos also include a linker purification oligo ($X^1_{LP}$) that binds to $X^1_{L2}$ and is partially complementary to $X^1_{L1}$ in the new region of overhang created when $X^1_{L2}$ binds to $X^1_{L1}$. The linker purification oligo ($X^1_{LP}$) is used to purify Part Z. The linker purification oligo ($X^1_{LP}$) is then removed by melting, leaving the part (Part Z) with the linker oligonucleotide consisting of $X^1_{L2}$ and $X^1_{PL1}$ attached.

Part Z also has a set of standard part oligos, which bind at the 5'-end of the part. The standard part oligos include a partially double stranded linker oligonucleotide that consists of a shorter oligonucleotide ($X^2_{P2}$) that binds to the overhang $S_P$ at the 5'-end of the part and a longer oligonucleotide ($X^2_{P1}$) that binds directly to the 5'-end of the part on the strand which does not have the overhang. $X^2_{P2}$ is complementary to $X^2_{P1}$ and since $X^2_{P1}$ is longer than $X^2_{P2}$ a new overhang is created at the 5'-end of the part.

In the part assembly phase, the parts A and Z are ligated together. The ligation occurs by means of the complementarity of the overhangs at the 3'-end of Part Z and at the 5'-end of Part A. These overhangs are created by oligos $X^1_{L1}$ and $X^1_{P1}$ respectively. It can be seen from FIG. 6 that the linker oligos of Part Z, $X^1_{L1}$ and $X^1_{L2}$, and the part oligos of Part A, $X^1_{P2}$ and $X^1_{P1}$, together form a standard linker $X^1$. The standard linker $X^1$ is sometimes referred to herein as X1.

FIG. 6 demonstrates only the assembly of two parts, Part A and Part Z, but the method demonstrated in FIG. 6 can be used to produce an assembly with a greater number of parts using the same process. In these embodiments of the invention, standard linkers $X^2$, $X^3$, $X^4$, $X^5$, $X^6$ and so on will be formed (sometimes referred to herein as $X^2$, $X^3$, $X^4$, $X^5$, $X^6$ and so on).

An alternative method for the assembly of a polynucleic acid sequence according to the present invention is shown in FIG. 7.

In the part cloning phase, a truncated part (in this case truncated Part A) is prepared by carrying out PCR using a forward primer ($A_F$) and a reverse primer ($A_R$). The primers are designed to produce a truncated version of Part A, lacking some of the sequence for the part, in this case the 5'-end sequence. As with the embodiment of the invention shown in FIG. 6, the truncated part is designed to be in a standard form, with a standard overhang at the 3'-end ($S_L$) and a standard overhang at the 5'-end ($A_O$), each of which is designed to be recognised by a particular restriction enzyme. Conveniently, the truncated part can be cloned into a plasmid for storage before carrying out the part preparation phase.

In the part preparation phase, the plasmid containing the truncated part is digested with one or more restriction enzymes that recognises and cuts the truncated part at a predefined sequence, leaving standard overhangs at the 3'-end ($S_L$) and at the 5'-end ($A_O$) of the truncated part.

In the part/linker assembly phase, the truncated part (in this case truncated Part A) is ligated and purified using one set of standard part oligos. These oligos bind at the 5'-end of the truncated part. The standard part oligos include a partially double stranded linker oligonucleotide that consists of a shorter oligonucleotide ($A_{P2}$) that binds to the overhang $A_O$ at the 5'-end of the truncated part and a longer oligonucleotide ($A_{P1}$) that binds directly to the 5'-end of the truncated part on the strand which does not have the overhang. $A_{P2}$ is complementary to $A_{P1}$ and since $A_{P1}$ is longer than $A_{P2}$ a new overhang is created at the 5'-end of the part.

The standard part oligos also include a part purification oligo ($A_{PP}$) that binds to $A_{P2}$ and is partially complementary to $A_{P1}$ in the new region of overhang created when $A_{P2}$ binds to $A_{P1}$. The part purification oligo ($A_{PP}$) is used to purify the truncated Part A. The part purification oligo ($A_{PP}$) is then removed by melting, leaving the truncated part (Part A) with the linker oligonucleotide consisting of $A_{P2}$ and $A_{P1}$ attached.

Meanwhile, truncated Part Z, which will bind to the 5'-end of truncated Part A, is prepared in a similar manner to truncated Part A. Truncated Part Z also has a standard overhang at the 3'-end ($S_L$). Truncated Part Z also has an overhang at the 5'-end, which may be a standard overhang ($A_O$) or some other overhang (e.g. $Z_O$).

In the part/linker assembly phase, the truncated part (in this case Part Z) is ligated and purified using one set of standard linker oligos. These oligos bind at the 3'-end of the truncated part. The standard linker oligos include a partially double stranded linker oligonucleotide that consists of a shorter oligonucleotide ($A_{L2}$) that binds to the overhang $S_L$ at the 3'-end of the truncated part and a longer oligonucleotide ($A_{L1}$) that binds directly to the 3'-end of the truncated part on the strand which does not have the overhang. $A_{L2}$ is complementary to $A_{L1}$ and since $A_{L1}$ is longer than $A_{L2}$ a new overhang is created at the 3'-end of the truncated part. This overhang is complementary to the overhang at the 5'-end of truncated Part A that is formed from $A_{P1}$.

The standard linker oligos also include a linker purification oligo ($A_{LP}$) that binds to $A_{L2}$ and is partially complementary to $A_{L1}$ in the new region of overhang created when $A_{L2}$ binds to $A_{L1}$. The linker purification oligo ($A_{LP}$) is used to purify Part Z. The linker purification oligo ($A_{LP}$) is then removed by melting, leaving the truncated part (Part Z) with the linker oligonucleotide consisting of $A_{L2}$ and $A_{pL1}$ attached.

Truncated Part Z also has a set of standard part oligos, which bind at the 5'-end of the part. The standard part oligos include a partially double stranded linker oligonucleotide that consists of a shorter oligonucleotide ($Z_{P2}$) that binds to the overhang at the 5'-end of the truncated part, which may be a standard overhang ($A_O$) or some other overhang (e.g. $Z_O$), and a longer oligonucleotide ($Z_{P1}$) that binds directly to the 5'-end of the truncated part on the strand which does not have the overhang. $Z_{P2}$ is complementary to $Z_{P1}$ and since $Z_{P1}$ is longer than $Z_{P2}$ a new overhang is created at the 5'-end of the truncated part.

In the part assembly phase, the truncated parts A and Z are ligated together. The ligation occurs by means of the complementarity of the overhangs at the 3'-end of truncated Part Z and at the 5'-end of truncated Part A. These overhangs are created by oligos $A_{L1}$ and $A_{P1}$ respectively. It can be seen from FIG. 7 that in this embodiment of the invention the linker oligos of truncated Part Z, $A_{L1}$ and $A_{L2}$, and the part oligos of truncated Part A, $A_{P2}$ and $A_{P1}$, together with truncated Part A form the complete Part A sequence.

FIG. 7 demonstrates only the assembly of two truncated parts, truncated Part A and truncated Part Z, but the method demonstrated in FIG. 7 can be used to produce an assembly with a greater number of truncated parts using the same process.

In the embodiment of the invention demonstrated in FIG. 6, the part is the nucleic acid sequence with the standard overhangs at the 3'-end and at the 5'-end. This assembly process leads to a longer scar between the parts, the scar consisting of the standard linker $X^1$.

In the embodiment of the invention demonstrated in FIG. 7, the part includes the truncated part and the accompanying linker and part oligos. This assembly process produces the non-truncated parts with a short standard scar (consisting of the overhangs at the 3'-end of each part, in this case $S_L$).

In one embodiment of the invention, the method involves preparing parts with short overhangs (typically of 3 or 4 bp) using one or more restriction enzymes. One of the short overhangs must be the same in all the parts; the other can be the same or can be different. Matching oligos are then chosen that convert the short overhangs into longer unique overhangs. Pathway assembly is then carried out using the long unique overhangs.

If the sequence present in the oligos is viewed as a component of the part (as in the embodiment demonstrated in FIG. 7), then the part is essentially truncated and then un-truncated during the assembly process. However, the part sequence can alternatively be viewed as not including the oligos (as in the embodiment demonstrated in FIG. 6). In this case, the assembly process involved adding an additional sequence (the linker and part oligos) between the parts.

In one embodiment, the present invention provides a method for the assembly of a polynucleic acid sequence as shown in FIG. 10. This illustrates in more detail a method for the assembly of a polynucleic acid sequence that is shown schematically in FIG. 9.

FIG. 10 also includes a step prior to step (i) of the method of the invention which involves ligating an oligonucleotide linker sequence $L1^{3'}$ to the 3'-end of a first nucleic acid sequence N1, ligating an oligonucleotide linker sequence $L1^{5'}$ to the 5'-end of the first nucleic acid sequence N1, ligating an oligonucleotide linker sequence $L2^{3'}$ to the 3'-end of the second nucleic acid sequence N2 and ligating an oligonucleotide linker sequence $L2^{5'}$ to the 5'-end of a second nucleic acid sequence N2.

This step is referred to in FIG. 10 as "part ligation". In this step, nucleic acid sequences are mixed with the relevant oligonucleotide linker sequences and a ligase and incubated to allow ligation to occur.

In the embodiment illustrated in Example 1 herein, the first nucleic acid sequence N1 is the plasmid pSB1C3 and the second nucleic acid sequence N2 is DNA encoding either GFP or RFP. The pSB1C3 DNA, the GFP DNA and the RFP DNA is all pre-digested with the restriction enzyme EarI.

As shown in FIG. 9, for these reactions the oligonucleotide linker sequence $L1^{3'}$ is called L2, the oligonucleotide linker sequence $L1^{5'}$ is called P1, the oligonucleotide linker sequence $L2^{3'}$ is called L1 and the oligonucleotide linker sequence $L2^{5'}$ is called P2. The oligonucleotide linker sequences P1, L1, P2 and L2 are collectively known as part/linker oligos.

FIG. 10 includes two purification steps; these are referred to as "part purification step 1" and "part purification step 2" in FIG. 10 and "part purification 1" and "part purification 2" in FIG. 9. In the part purification steps, biotinylated purification oligos PP1, PL2, PP2 and PL2 are used to remove any unbound oligonucleotide linker sequences. The purification oligos bind to the part/linker oligos described above. PP1 binds to P1, PL2 binds to L2, PP2 binds to P2 and PL2 binds to L2. In part purification step 1, part purification oligos PP1 and PP2 are used to remove any unbound oligonucleotide linker sequences P1 and P2. In part purification step 2, part purification oligos PL1 and PL2 are used to remove any unbound oligonucleotide linker sequences L1 and L2.

Streptavidin coated magnetic beads are used in the purification steps. As mentioned above, the purification oligos are biotinylated, and therefore bind to the streptavidin coated magnetic beads. Any unbound oligonucleotide linker sequences therefore bind to the purification oligos, which in turn bind to the streptavidin coated magnetic beads, which can be separated from the reaction mixture by magnetic means.

A two-step purification method is also illustrated in FIG. 11.

The step referred to as "pathway assembly" in FIG. 10 corresponds to step (iv) of the method of the invention. Thus, in this step the nucleic acid sequences are ligated to form a polynucleic acid sequence. As shown in FIG. 9, the assemblies that are formed are either pSB1C3.GFP or pSB1C3.RFP.

The final step shown in FIG. 10 is referred to as "transformation" (or "part transformation in FIG. 9). In this step, the polynucleic acid sequences formed in the pathway assembly step are transformed into suitable cells, grown for a suitable amount of time and then plated out and results determined. A successful assembly of pSB1C3.GFP produces green cells and a successful assembly of pSB1C3.RFP produces red cells. The number of colonies (yield) and percent of colonies with correct phenotype (efficiency) can be determined for each of the assemblies.

FIG. 10 demonstrates only the assembly of two parts, but the method shown in FIG. 10 can also be used to produce an assembly with a greater number of parts using the same process.

The method of the present invention has the following advantages:
All parts to be assembled are in a standard form.
A library of such standard parts can be created and any set of those parts can be assembled in any order.
By using an offset cutter that leaves non-palidromic overhangs, many incorrect side products arising from palindromic overhangs (e.g. formed from most restriction enzymes) are eliminated.
No new oligos need to be synthesized during the assembly process.
The process is extremely parallel and in the best case, requires constant time independent of the number of parts being assembled.
The entire time for assembly can be extremely fast. An optimal assembly would only require two ligations and three biotin-based purifications.
The entire process involves a small number of simple operations amenable to automation.
The process does not require in vivo steps (e.g. yeast recombination), enabling the construction of DNA that might be unstable or toxic to cells.
The process is compatible with further in vivo processing (e.g. bacterial transformation of assembled circular plasmid and parts).
The only enzyme required in the assembly process is DNA ligase. It does not require polymerases, nucleases, recombinases, or other enzymes.
No amplification is required, reducing the chances of errors.
The resulting product is pure from incorrectly assembled products, eliminating the costly need for sequencing, assuming high quality input parts and oligos.
Ligation has been shown to scale to at least 150 kb.
Parts with similar overhangs can be assembled by splitting the last pathway assembly step into multiple cycles (unlike, for example, PCR based approaches).
Similar parts can be assembled in one pot if they are designed appropriately. For example, there is flexibility when designing how to break a part into the oligo portion and the rest. The actual sequence of the overhang that will be ligated during the one pot assembly step is entirely determined by the oligos used. By changing the overhang (e.g. changing its length or whether it's a 5'- or 3'-overhang), similar parts can be assembled in one pot (e.g. assembling two GFP variants together).
A small number of parts can form a large number for pathways. For example, suppose one has 5 possible promoters that one wants to test in front of each of the genes in a 5 gene pathway. There are 10 total parts (5 promoters+5 genes). The number of possible promoter-gene and gene-promoter junctions is 50, i.e. at most 50 different part-linker fusions need to be done. These 50 part-linker fusions can then be assembled into $5^5=3125$ different pathways in one pot reactions.

At least step (iv) of the method of the present invention is carried out on a microfluidic device.

As defined herein, a microfluidic device is a device for manipulating minute amounts of fluid, usually microliters (μL or μl) or nanoliters (nL or nl). Such devices are known in the art. They are typically substantially planar and frequently contain features such as chambers, channels and/or valves. Typically, when a microfluidic device contains a plurality of chambers, they are linked to each other via fluid channels which can contain valves. Such valves can be opened and closed in series to effect pumping of fluid through the fluid channels. Typically, the dimensions of such a microfluidic device are on the cm scale, for example from around 5 cm to 8 cm by 6 cm to 11 cm, typically 5 cm by 11 cm, 6 cm by 10 cm or 7 cm by 9 cm.

In one embodiment, the microfluidic device comprises at least one input chamber, at least one storage chamber, at least one reaction chamber and at least one output chamber and wherein each of said at least one input chamber, at least one storage chamber and at least one output chamber is linked by a separate fluid channel to said at least one reaction chamber.

An input chamber is a chamber for holding fluid which is open to the atmosphere such that fluid can be introduced into said chamber, for example by injection. The input chamber can therefore also be described as an injection chamber. The input chamber may optionally have a removable cover, which is suitably transparent. An input chamber is also described herein as an "input reservoir".

An output chamber is a chamber for holding fluid which is open to the atmosphere such that fluid can be removed from said chamber. The output chamber can therefore also be described as a collection chamber. The output chamber may optionally have a removable cover, which is suitably transparent. An output chamber is also described herein as an "output reservoir".

A storage chamber is a chamber for holding fluid which is optionally open to the atmosphere such that fluid can be introduced into or removed from said chamber. The storage chamber may optionally have a removable cover, which is suitably transparent. A storage chamber is also described herein as a "temporary chamber" or an "intermediate product chamber".

A reaction chamber is a chamber in which reactions, typically biological reactions, take place. The reaction chamber is typically closed to the atmosphere, typically in order to prevent contamination.

Each of the at least one input chamber, at least one storage chamber and at least one output chamber is linked by a separate fluid channel to the at least one reaction chamber. In other words, a fluid channel links each input chamber to each reaction chamber, a separate fluid channel links each storage chamber to each reaction chamber and a separate fluid channel links each output chamber to each reaction chamber. Thus, each of the at least one input chamber, at least one storage chamber and at least one output chamber is in fluid communication with the at least one reaction chamber.

A fluid channel is a vessel through which fluid can flow. Typically, the volumes of fluid that flow through the fluid channel are on the microliter or nanoliter scale.

In one embodiment, the microfluidic device comprises two input chambers, one storage chamber, one reaction chamber and two output chambers. In this embodiment, a fluid channel links the first input chamber to the reaction chamber, a second fluid channel links the second input chamber to the reaction chamber, a third fluid channel links the storage chamber to the reaction chamber, a fourth fluid channel links the first output chamber to the reaction chamber and a fifth fluid channel links the second output chamber to the reaction chamber. An example of this layout is illustrated in FIG. 12.

The input chambers, storage chamber and/or output chambers are typically substantially circular. This embodiment is illustrated in FIG. 12.

In one embodiment, the reaction chamber is substantially elliptical. This embodiment is illustrated in FIG. 12.

In one embodiment, one or more of the fluid channels has one or more valves. These valves are operable to control the flow of fluid through the fluid channels. As such, the valves can prevent or allow the flow of fluid through the fluid channels. Typically, one or more of the fluid channels has two or more valves, such as three, four or five valves. As set out above, such valves can be opened and closed in series to effect pumping of fluid through the fluid channels.

In one embodiment, one or more of the fluid channels has two valves and a pump chamber is located between these two valves. A pump chamber is a chamber for holding fluid and is typically closed to the atmosphere. The pump chamber is typically substantially circular. In one embodiment, more than one of the fluid channels has this arrangement of valves and a pump chamber. For example, two, three, four or more of the fluid channels has this arrangement of valves and a pump chamber. As shown in FIG. 13, the arrangement of two valves and a pump chamber is described herein as a pump.

As shown in FIG. 13, the arrangement of one input chamber, together with its respective fluid channel containing two valves with a pump chamber inbetween is described herein as an "inlet channel" or "input channel". Similarly, as shown in FIG. 13, the arrangement of the storage chamber, together with its respective fluid channel containing two valves with a pump chamber inbetween is described herein as an "intermediate product channel" or "storage channel". As shown in FIG. 13, the arrangement of an output chamber together with its respective fluid channel containing a valve is described herein as a "waste and/or product chamber".

Typically, the depth of the chambers and fluid channels in the microfluidic device is in the range from 100 µm to 500 µm, typically from 200 µm to 400 µm, more typically from 250 µm to 300 µm. Typically, the depth of the chambers and fluid channels in the microfluidic device is 250 µm.

Typically, the diameter of the input chamber, storage chamber and/or output chamber is in the range from 1 mm to 10 mm, typically from 2 mm to 9 mm, from 3 mm to 8 mm, from 4 mm to 7 mm, from 4.5 mm to 6 mm, typically from 4.5 mm to 5.5 mm, from 4.6 mm to 5.4 mm, from 4.7 mm to 5.3 mm or from 4.8 mm to 5.2 mm, typically 5.2 mm.

Typically, the dimensions of the reaction chamber are from 3 mm to 9 mm by 5 mm to 15 mm, for example 3 mm by 15 mm, 4 mm by 14 mm, 5 mm by 13 mm, 6 mm by 12 mm, 7 mm by 11 mm. Typically, the dimensions of the reaction chamber are around 6 mm by 10.5 mm, typically 5.9 mm by 10.4 mm.

Typically, the width of the fluid channel is in the range from 0.1 mm to 0.8 mm, typically from 0.2 mm to 0.7 mm, from 0.3 mm to 0.6 mm, from 0.4 mm to 0.5 mm, typically 0.4 mm.

Typically, the diameter of the pump chamber is in the range from 1 mm to 5 mm, typically from 2 mm to 4 mm, from 2.5 mm to 3.5 mm, from 2.75 mm to 3.25 mm, typically around 3.16 mm.

Typically, the dimensions of the valves are from 0.5 mm to 1.5 mm by 2 mm to 4 mm, for example 0.5 mm by 4 mm, 1 mm by 3 mm, 1.5 mm by 2 mm, typically 1 mm by 2.2 mm.

In one embodiment of the invention, the microfluidic device comprises two input chambers, one storage chamber, one reaction chamber and two output chambers, and each of the fluid channels linking the input chambers to the reaction chamber and the fluid channel linking the storage chamber to the reaction chamber have two valves and a pump chamber is located between these two valves. In addition, each of the fluid channels linking the output chambers to the reaction chamber has one valve. This embodiment of the invention is illustrated in FIG. 12.

Such a microfluidic device is suitable for carrying out the method described in Example 1 herein. Nucleic acid sequences are typically introduced into the input chambers together with the necessary reagents. The nucleic acid sequences and reagents are pumped into the central reaction chamber where ligation takes place and the products, i.e. polynucleic acid sequences having the desired assemblies, are pumped to the output chamber and then removed.

As set out above, at least step (iv) of the method of the present invention is carried out on a microfluidic device. However, other steps of the method of the present invention can also be carried out on a microfluidic device. For example, the step of purifying the nucleic acid sequences immediately prior to step (iv) can also be carried out on a microfluidic device. In this embodiment of the invention, step (iv) and the step of purifying the nucleic acid sequences immediately prior to step (iv) can be carried out on the same microfluidic device or different microfluidic devices. When these steps are carried out on different microfluidic devices, the microfluidic devices are optionally connected, or if not connected, means are provided for transferring fluid from one device to another.

The microfluidic device shown in FIG. 12 is suitable for carrying out both step (iv) and the step of purifying the nucleic acid sequences immediately prior to step (iv). Thus, in this embodiment of the invention, step (iv) and the step of purifying the nucleic acid sequences immediately prior to step (iv) are carried out on the same microfluidic device.

In the embodiment of the invention where step (iv) and the step of purifying the nucleic acid sequences immediately prior to step (iv) are carried out on different microfluidic devices, the layout of the microfluidic devices used for each step can be tailored to the requirements of each of such steps.

Therefore, in one embodiment, the microfluidic device is suitable for carrying out step (iv). This corresponds to the step labelled "pathway assembly" in FIG. 10. Such a microfluidic device is also referred to as an "assembly chip" herein. Such a microfluidic device allows the high throughput assembly of polynucleic acid sequences such as DNA sequences to be carried out using the method of the invention. A microfluidic device suitable for carrying out step (iv) of the method of the invention can also be suitable for carrying out the step referred to in FIG. 10 as "part ligation". This is a step prior to step (i) of the method of the invention which involves ligating an oligonucleotide linker sequence L1$^{3'}$ to the 3'-end of a first nucleic acid sequence N1 and/or ligating an oligonucleotide linker sequence L1$^{5'}$ to the 5'-end of the first nucleic acid sequence N1 and/or ligating an oligonucleotide linker sequence L2$^{3'}$ to the 3'-end of the second nucleic acid sequence N2 and/or ligating an oligonucleotide linker sequence L2$^{5'}$ to the 5'-end of a second nucleic acid sequence N2.

In this embodiment of the invention, the microfluidic device comprises at least two input chambers, at least one auxiliary chamber and at least one output chamber and each of said at least two input chambers and said at least one auxiliary chamber is linked by a central fluid channel to said at least one output chamber. A microfluidic device having a layout in accordance with this embodiment of the invention is shown in FIG. 14A.

An auxiliary chamber is a chamber for holding fluid which is open to the atmosphere such that fluid can be introduced into said chamber, for example by injection. The auxiliary chamber may optionally have a removable cover, which is suitably transparent. An auxiliary chamber is also described herein as an "auxiliary reservoir".

In this embodiment of the invention, each of the nucleic acid sequences to be assembled into a polynucleic acid sequence by the method of the invention is typically introduced into a separate input chamber. There is therefore typically one input chamber per nucleic acid sequence that is assembled into a polynucleic acid sequence by the method of the invention. The number of input chambers is typically 2, 3, 4, 5, 6, 7, 8, 9, 10, 11, 12, 13, 14, 15, 16, 17, 18, 19 or 20 but can be more than 20, for example 25, 30, 35, 40, 45, 48, 50, 52, 54, 56, 58 or 60.

In one embodiment, half of the input chambers lie on one side of the central fluid channel and half of the input chambers lie on the other side of the central fluid channel. Alternatively, there may be an asymmetric arrangement of input chambers, i.e. more input chambers lie on one side of the central fluid channel than the other.

In this embodiment of the invention, there are typically 1, 2, 3, 4, 5 or 6 auxiliary chambers. Typically, there are 2 auxiliary chambers.

In this embodiment of the invention, there are typically 1, 2, 3, 4, 5 or 6 output chambers. Typically, there are 2 output chambers.

All of the input chambers feed into the central fluid channel which links each of the input chambers to the output chamber. In operation, a fluid such as oil or water can be introduced into the auxiliary chamber and then pumped into the central fluid channel, which typically has the effect of pushing the nucleic acid sequences along the central fluid channel where they mix and ligate, and eventually arrive in the output chambers, from which the finished polynucleic acid product can be removed. Suitably, a fluid such as oil can be used to push the nucleic acid sequences along the channels in order to avoid dilution. Water may also be used for washing or other purposes.

The central fluid channel is typically straight, as shown in FIG. 14A. However, the central fluid channel may take another suitable configuration and thus may be, for example, curved or in the form of a zig zag.

In one embodiment of the invention, one or more of the input chambers is linked to the central fluid channel by a further fluid channel. Typically, each of the input chambers is linked to the central fluid channel by a further fluid channel. In one embodiment, one or more of the further fluid channels has one or more valves. In one embodiment, one or more of such further fluid channels has two valves and a pump chamber is located between these two valves. In one embodiment, each of the further fluid channels has two valves and a pump chamber is located between these two valves. An example of this embodiment of the invention is illustrated in FIG. 14A.

In one embodiment, the further fluid channels linking input chambers on either side of the central fluid channel to the central fluid channel are lined up symmetrically, as shown in FIG. 14A. In other words, the fluid channels linking input chambers on either side of the central fluid channel to the central fluid channel enter the central fluid channel at a position directly opposite to each other. In another embodiment, the further fluid channels linking input chambers on either side of the central fluid channel to the central fluid channel are lined up asymmetrically, as shown in FIG. 14B. In other words, the connections of the further fluid channels to either side of the central fluid channel are offset. This layout can be used, for example, to reduce cross-contamination.

In one embodiment, the tips of the further fluid channels linking the input chambers to the central fluid channel are nozzled, as shown in FIG. 14C. In this embodiment, the microfluidic device is typically manufactured by laser cutting.

In one embodiment of the invention, one or more of the auxiliary chambers is linked to the central fluid channel by a further fluid channel. Typically, each of the auxiliary chambers is linked to the central fluid channel by a further fluid channel. In one embodiment, one or more of the further fluid channels has one or more valves. In one embodiment, one or more of such further fluid channels has two valves and a pump chamber is located between these two valves. In one embodiment, each of the further fluid channels has two valves and a pump chamber is located between these two valves. An example of this embodiment of the invention is illustrated in FIG. 14A.

In one embodiment of the invention, one or more of the output chambers is linked to the central fluid channel by a further fluid channel. Typically, each of the output chambers is linked to the central fluid channel by a further fluid channel. In one embodiment, one or more of the further fluid channels has one or more valves. An example of this embodiment of the invention is illustrated in FIG. 14A.

In one embodiment, the microfluidic device further comprises a reaction chamber.

In one embodiment, the microfluidic device comprises 16 input chambers, 2 auxiliary chambers and 2 output chambers. An example of this layout is illustrated in FIG. 14A. This layout is also referred to herein as "Chip 3A". Using this microfluidic device, nucleic acid sequences to be assembled can be placed in the input chambers in order to be pumped in a combinatorial fashion, and pushed via fluid pumping to the output chamber, ready to be collected in the form of assembled polynucleic acid sequences. As set out above, this microfluidic device can also be used to carry out a ligation step prior to step (i) of the method of the invention such as that referred to in FIG. 10 as "part ligation". This microfluidic device can therefore be used to carry out high throughput ligation or assembly of up to 16 inputs, typically nucleic acid sequences, in a single device.

In another embodiment, the microfluidic device is suitable for carrying out the step of purifying the nucleic acid sequences immediately prior to step (iv). In one embodiment, multiple purification steps are carried out immediately prior to step (iv). Typically, two purification steps are carried out immediately prior to step (iv).

In this embodiment of the invention, the microfluidic device comprises at least one input chamber, at least one auxiliary chamber, at least one reaction chamber, at least one waste chamber and at least one output chamber, wherein said at least one input chamber is linked by a fluid channel to said at least one reaction chamber, said at least one reaction chamber is linked by a fluid channel to said at least one output chamber, said at least one auxiliary chamber is linked by a fluid channel to said at least one waste chamber, and wherein the fluid channel linking said at least one auxiliary chamber to said at least one waste chamber intersects the fluid channel linking said at least one input chamber to said at least one reaction chamber.

A waste chamber is a chamber for holding fluid which is open to the atmosphere such that fluid can be removed from said chamber. The waste chamber may optionally have a removable cover, which is suitably transparent. A waste chamber is also described herein as a "waste reservoir".

In this embodiment of the invention, there is typically one input chamber per nucleic acid sequence that is assembled into a polynucleic acid sequence by the method of the invention.

The number of input chambers is typically 2, 3, 4, 5, 6, 7, 8, 9, 10, 11, 12, 13, 14, 15, 16, 17, 18, 19 or 20 but can be more than 20, for example 25, 30, 35, 40, 45, 48, 50, 52, 54, 56, 58 or 60.

The number of input chambers is typically the same as the number of reaction chambers. The number of input chambers is also typically the same as the number of output chambers. The number of reaction chambers is also typically the same as the number of output chambers. The number of output chambers and the number of reaction chambers is therefore also typically 2, 3, 4, 5, 6, 7, 8, 9, 10, 11, 12, 13, 14, 15, 16, 17, 18, 19 or 20 but can be more than 20, for example 25, 30, 35, 40, 45, 48, 50, 52, 54, 56, 58 or 60.

In this embodiment, the fluid channel linking the at least one auxiliary chamber to the at least one waste chamber intersects the fluid channel linking said at least one input chamber to said at least one reaction chamber. In other words, the fluid channel linking the at least one auxiliary chamber to the at least one waste chamber crosses over or joins the fluid channel linking said at least one input chamber to said at least one reaction chamber. Typically, there is one auxiliary chamber and one waste chamber. In one embodiment, where there are a plurality of input chambers, the fluid channel linking the auxiliary chamber to the waste chamber intersects each of the fluid channels linking the input chambers to the reaction chambers. Typically, the fluid channel linking the auxiliary chamber to the waste chamber intersects each of the fluid channels linking the input chambers to the reaction chambers at an angle of 90°. This embodiment is illustrated in FIG. 15.

In one embodiment, one or more of the fluid channels linking the input chambers to the reaction chambers has two valves and a pump chamber is located between these two valves. In one embodiment, the fluid channel linking the at least one auxiliary chamber to the at least one waste chamber intersects one or more of the fluid channels linking the at least one input chamber to the at least one reaction chamber between one of the valves and the pump chamber. In other embodiments, the fluid channel linking the at least one auxiliary chamber to the at least one waste chamber intersects one or more of the fluid channels linking the at least one input chamber to the at least one reaction chamber between the input chamber and one of the valves, or between one of the valves and the reaction chamber.

In one embodiment, there is an additional fluid channel that branches from the fluid channel that links the input chamber to the reaction chamber and joins the fluid channel that links the reaction chamber to the output chamber. This fluid channel allows fluid flowing from the input chamber to the output chamber to bypass the reaction chamber. This fluid channel can therefore be described as a bypass fluid channel. This fluid channel typically includes two valves and a pump chamber located between these two valves. This fluid channel can therefore act as a side pump, which can be used, for example, for mixing fluid. In one embodiment, such an additional fluid channel bypasses each of the reaction chambers.

In one embodiment, the microfluidic device comprises 4 input chambers, 1 auxiliary chamber, 4 reaction chambers, 1 waste chamber and 4 output chambers and the fluid channel linking the auxiliary chamber to the waste chamber intersects each of the fluid channels linking the input chambers to the reaction chambers. An example of this embodiment of the invention, is illustrated in FIG. 15. Heating and/or magnetic actuation (separation and/or mixing) can be carried out on this microfluidic device as described herein. For example, heating can be carried out using a Peltier device.

In one embodiment, the layout of the microfluidic device described in relation to this embodiment of the invention can be reproduced twice or more on the same microfluidic device. An example of a microfluidic device wherein the above-described layout is reproduced twice is illustrated in FIG. 15. This layout is also referred to herein as "Chip 3P". The same layout can therefore be reproduced for example 2, 3, 4, 5, 6 or more times on the same microfluidic device. This allows for purification of various nucleic acid sequences in parallel and is useful in a high throughput method. Alternatively or in addition, different layouts can be included in the same microfluidic device such that ligation and purification can be carried out on the same microfluidic device, but in different areas of the device.

FIG. 27 demonstrates in detail an example of how to operate a pump to flow liquid from a chamber through a fluid channel using the microfluidic device of the invention. For example, the operation of the pump demonstrated in FIG. 27 can be used to pump liquid from one of the input chambers into the reaction chamber or from the storage chamber to the reaction chamber in the microfluidic device shown in FIG. 12. Alternatively, the operation of the pump demonstrated in FIG. 27 can be used to pump liquid from one of the input chambers into the central fluid channel or from one of the auxiliary chambers into the central fluid channel in the microfluidic device shown in FIG. 14A. Alternatively, the operation of the pump demonstrated in FIG. 27 can be used to pump liquid from one of the input chambers into the one of the reaction chambers, from one of the reaction chambers to one of the output chambers, from one of the auxiliary chambers to one of the waste chambers or through the side pump in the microfluidic device shown in FIG. 15.

Each "pump" unit features two valves and 1 pump chamber. The pump chamber is surrounded by two valves in all pump unit arrangements. Different pump sequences can be used to activate the flow in the channel. FIG. 27 shows the order in which the valves and the pump chamber should be closed in order to effect flow of fluid in the fluid channel in the direction shown in the Figure. In FIG. 27 the sequence used corresponds to: 100, 110, 010, 011, 001, 101, where "1" corresponds to a structure closed (valve or pump chamber)

and "0" corresponds to an open structure. Note that this sequence is not the only one that could be used.

By this operation a flow is actuated. This is not dissimilar to the actuation of a peristaltic pump. However, the dimensions are much smaller and a decoupling concept is added. These six sequences correspond to a single pumping cycle. Pumping can also be effected in the opposite direction to that shown in FIG. 27.

For the microfluidic device shown in FIG. 12, in some embodiments, the pumps between both of the input chambers and the reaction chamber are activated at the same time and in other embodiments only one of the pumps between the input chambers and the reaction chamber is used at a time. In other words, in the latter embodiment, while one pump is activated, the other pump remains closed at all times. This latter embodiment was carried out in Example 1 herein.

FIG. 28 presents some of the different fluidic cycles that can be performed on the microfluidic device. These cycles do not necessarily represent a chronological order. However, they represent some of the "movements" which can be performed on-chip. FIG. 10, which describes the protocol used in Example 1 herein, also refers in the last column to the chip cycles referred to in FIG. 28, using the same lettering. FIG. 28 demonstrates the fluidic cycles on the microfluidic device shown in FIGS. 12 and 13, but is equally applicable to the other microfluidic devices of the invention described herein.

The numbers in FIG. 28 represent valves. As can be seen from FIG. 28, the microfluidic device shown in that Figure has 12 valves. In this embodiment, the reaction chamber has a valve. This is valve number 10 in FIG. 28.

Each pump "actuation" corresponds to a number n of pumping cycles as presented elsewhere.

The fluidic steps shown in FIG. 28 are as follows:
- a—Fluid from inlet channel 1 is pumped into the Reaction chamber. Valve 11 is left open to allow the fluid out into Waste/product chamber 1. Inlet Channel 2 and Intermediate product channel are closed. Biological example: Load magnetic beads and binding buffer into the reaction chamber in part purification step 1 shown in FIG. 10.
- b—Inlet channel 1 and Intermediate product channel are closed. Fluid from the inlet channel 2 is loaded into the reaction chamber. Biological example: Oligos and binding buffer are loaded into the reaction chamber to bind on the magnetic beads in part purification step 1 shown in FIG. 10.
- c—All the valves are closed. The reaction chamber is therefore isolated. A manual mixing protocol (see elsewhere) is applied on the chamber. Biological example: Oligos and beads are mixed together for better binding in part purification step 1 and part purification step 2 shown in FIG. 10.
- d—Inlet channel 2 is closed, valves 11 and 12 are closed. Intermediate product channel and inlet channel 1 are open. Inlet channel 1 is pumped forward (ie from input chamber to reaction chamber) and Intermediate product channel is pumped backward (ie from reaction chamber to storage chamber) in order to push the fluid inside the reaction chamber with a fresh fluid from Inlet channel 1. Biological example: Elution from part purification step 1 is stored in the intermediate product channel.
- e—All channels closed but Inlet channel 2. A reagent is introduced in the reaction chamber from inlet channel 2. Valve 11 is opened for evacuation of the previous fluid from the reaction chamber. Biological example: Oligos and binding buffer are loaded into the reaction chamber in part purification step 2 shown in FIG. 10.
- f—All channels closed but Intermediate product channel. The product stored in the Intermediate product channel is pumped back into the reaction chamber. Biological example: Elution from part purification step 1 is introduced in part purification step 2.
- g—All the valves are closed. The reaction chamber is therefore isolated. A heating protocol (see elsewhere) is applied on the chamber. Biological example: Heating to elute oligos from magnetic beads (unbinding) in part purification step 1 and part purification step 2 shown in FIG. 10.
- h—The reaction chamber is emptied into the waste and/or product chamber number 1 via the actuation of a buffer flow in inlet channel number 1. Biological example: Unloading of the elution product.

Two exemplary techniques to manufacture microfluidic structures (width<1 mm) in PMMA substrates with stretched silicone rubber membrane to close the structure are as follows. The first technique involves one layer of double-sided adhesive transfer tape, and the second technique involves two layers of double-sided adhesive transfer tape.

In the first technique (FIG. 16) the microchannels are engraved directly on to the PMMA block coated with a layer of double-sided transfer tape protected on one side. After engraving of the microchannels the protective layer is removed and the stretched silicone rubber membrane can be directly applied to seal the channel.

In the second technique (FIG. 17), the channels are cut through a thin layer of PMMA sheet coated with 2 layers of double-sided adhesive transfer tape using laser cutting. The microfluidic access are laser-cut in the PMMA substrate. One protective sheet is removed from the cut through piece and applied to the PMMA substrate. The bond can be enhanced by simply manually exerting pressure on the assembly. This can also be done by using a roller. The second protective cover is then removed and the stretched silicone membrane is bonded onto the assembly.

In one embodiment, the chambers and the fluid channels are located between a rigid layer and an elastic layer and the microfluidic device is configured so that deformation of the elastic layer manipulates fluid if present in said chambers or said fluid channels.

This embodiment of the present invention is described in detail in International Patent Application No. PCT/GB2009/002968 (WO 2010/073020).

The microfluidic device can be detachably coupleable to a control platform that is operable to deform the elastic layer.

The elastic layer can form at least part of an external surface of the microfluidic device. At least one part of the elastic layer can be deformable to cause operation of a microfluidic control component of the microfluidic device. The microfluidic control component can comprise a valve, mixer, or pump.

In one embodiment, the microfluidic device is part of a microfluidic system comprising a microfluidic device as defined herein; and a control platform comprising means for deforming the elastic layer thereby to manipulate fluid in the at least one fluid chamber or channel.

By providing a control platform and a detachable microfluidic device, a system that is particularly simple to manufacture can be provided. The elastic layer can provide an interface that enables the manipulation of fluid in the at least one fluid chamber or channel using devices external of the microfluidic device, provided for example on the control platform.

This embodiment of the present invention is also described in detail in International Patent Application No. PCT/GB2009/002968 (WO 2010/073020).

Electronic, electromechanical, optical or other complex control or measurement components can be provided on the control platform rather than on the microfluidic device, reducing the complexity of manufacture of the microfluidic device. The microfluidic device can be manufactured using low cost materials and fabrication processes, and can be treated as disposable.

The manipulation of fluid in the at least one fluid chamber of channel can include, for example, controlling fluid flow or other fluid dynamics. Fluid flow can be flow along a chamber or channel or fluid flow within a chamber or channel.

A microfluidic system or device can be for example a system or device for manipulation of fluids on the millimeter or sub-millimeter scale, for example a system or device that includes at least one fluid chamber or channel at least part of which has at least one dimension that is less than or equal to around 1 mm.

The rigid layer is usually sufficiently rigid that if the rigid layer is held stationary, a force applied to the elastic layer causes a deformation of the elastic layer relative to the rigid layer. The rigid layer can be substantially rigid in whole or part. The rigid layer can comprise a plurality of sub-layers or components. The rigid layer can for example comprise a substantially rigid portion (for example a substantially rigid frame) and a flexible portion fixed to the substantially rigid portion.

The microfluidic device and the detachable control platform can be coupleable in at least one alignment position, in which the means for deforming the elastic layer is operable to selectively deform at least one selected part of the elastic layer. Thus, fluid can be manipulated at selected parts of the microfluidic device.

The at least one selected part of the elastic layer can comprise at least one part of the elastic layer at which deformation of the elastic layer causes operation of a microfluidic control component of the microfluidic device. The microfluidic control component can comprise a valve, mixer, or pump.

The microfluidic device and the control platform can be coupleable in a plurality of different alignment positions, and in each alignment position deformation of the elastic layer can cause operation of a respective at least one microfluidic control component of the microfluidic device. Thus, the same control platform can be used to perform a plurality of different operations on fluid in the microfluidic device. The microfluidic device can be placed in the plurality of different alignment positions in turn, with a different operation being performed on fluid in the microfluidic device at each alignment position.

The means for deforming the elastic layer can comprise means for applying force. The control platform can comprise an external face that is coupleable to the elastic layer of the microfluidic device, and the means for applying force can be operable to apply force at at least one part of the external face. The external face can be in contact with, or spaced apart from, the elastic layer of the microfluidic device. The means for applying force can be operable to apply a force that has a component in a direction substantially perpendicular to the external face.

The means for applying force can be operable to apply force over an area, that area being larger than the area of the at least one part of the elastic layer at which deformation of the elastic layer causes operation of a microfluidic control component of the microfluidic device. Thus, it can be particularly straightforward to align the control platform and the microfluidic device, as it can be sufficient that the larger area over which force is applied covers the smaller area of the at least one part of the elastic layer at which deformation of the elastic layer causes operation of a microfluidic control component of the microfluidic device. That feature is particularly useful when the means for applying force is able to cause different amounts of deformation of the elastic layer across the area over which force is applied, for example when the means for applying force applies force using fluid pressure.

The means for deforming the elastic layer can comprise means for applying fluid pressure to the elastic layer. The means for applying fluid pressure can be operable to apply pressure to one side of the elastic layer that is greater than or less than the pressure acting on the other side of the elastic layer. The applied pressure can be an over-pressure or an under-pressure, and can comprise an at least partial vacuum. The means for applying fluid pressure can be arranged to provide pressurised fluid in direct contact with the elastic layer.

The means for deforming the elastic layer can comprise a microactuator mechanism.

The elastic layer can form at least part of an external surface of the microfluidic device.

The system can further comprise alignment means for aligning the control platform and the microfluidic device. The alignment means can be configured to align the or a face of the control platform with the elastic layer. The alignment means can be operable to align the control platform and the microfluidic device in the or an at least one alignment position. The alignment means can be operable to align the means for deforming the elastic layer with the or an at least one selected part of the elastic layer.

The alignment means can be arranged to align the control platform and the microfluidic device so that the area over which the means for applying force is operable to apply force at least partially overlaps the at least one part of the elastic layer at which deformation of the elastic layer causes operation of a microfluidic control component of the microfluidic device. The alignment means can be operable to align the face and elastic layer to be substantially parallel.

The alignment means can comprise at least one male element and at least one female element configured to receive the at least one male element. The male element or at least one of the male elements can be provided on one of the microfluidic device and the control platform and the corresponding female element or a corresponding at least one of the female elements can be provided on the other of the microfluidic device and the control platform. The alignment means can comprise at least one alignment mark on each of the microfluidic device and the control platform.

The system can further comprise means for detachably coupling the control platform to the microfluidic device. The coupling means can comprise means for forming a seal between at least part of the control platform and at least part of the elastic layer.

The means for deforming the elastic layer can comprise means for applying fluid pressure to the elastic layer, and the means for forming a seal can be arranged to form a seal around an area of the elastic layer so that fluid pressure is applied to the elastic layer over the sealed area. The sealed area can comprise the or an at least one part of the elastic layer at which deformation of the elastic layer causes operation of a microfluidic control component of the microfluidic device. The sealed area can be greater than the area of the or an at least one part of the elastic layer at which deformation of the elastic layer causes operation of a microfluidic control component of the microfluidic device.

The control platform can comprise the or a face that is coupleable to the elastic layer of the microfluidic layer, and the means for forming a seal can comprise at least one element that protrudes above the face of the control platform for engagement with the elastic layer.

The means for forming a seal can comprise an O-ring. The coupling means can comprise fixing means for detachably fixing the microfluidic device to the control platform, for example at least one of a clamp, a screw, a bolt and an adhesive, typically a releasable adhesive.

The control platform can comprise at least one device for performing an operation on fluid in the microfluidic device. The at least one device for performing an operation can comprise at least one sensor for sensing a property of fluid in the microfluidic device, or can comprise a device for altering a property of the fluid, for example a heater. Typically, the heater is a Peltier device.

The system can further comprise biasing means for biasing away from the control platform the at least one device for performing an operation. The biasing means can be arranged so that when the microfluidic device and the control platform are coupled such that the deforming means is operable to deform the elastic layer, the device for performing an operation on the fluid is biased towards the microfluidic device. The biasing means can be arranged so that when the microfluidic device and the control platform are coupled such that the deforming means is operable to deform the elastic layer, the device for performing an operation on the fluid is biased to be in contact with the elastic layer. The biasing means can comprise at least one spring.

The system can further comprise a plurality of microfluidic devices each of which is coupleable to the control platform. The system can comprise a plurality of control platforms, each of which is coupleable to the microfluidic device or to each of the microfluidic devices.

The system can further comprise means for controlling operation of the deforming means.

The elastic layer can form a wall of the fluid chamber or channel, and the fluid chamber or channel can comprise a further, opposing wall, and the control means can be operable to control the deforming means to deform the elastic layer towards the opposing wall. The control means can be operable to control the deforming means to deform the elastic layer to be in contact with the opposing wall.

The control means can be operable to successively deform different parts of the elastic layer in a sequence to perform a desired fluid operation. The desired fluid operation can comprise at least one of pumping, mixing and allowing or preventing flow of the fluid. The control means can be operable to repeatedly deform the or an at least part of the elastic layer thereby to perform a fluid operation.

In one embodiment, the microfluidic system comprises a microfluidic device comprising at least one fluid chamber or channel, wherein an elastic layer forms at least one wall of the at least one fluid chamber or channel; means for deforming the elastic layer; control means operable to control the deforming means to repeatedly deform the elastic layer thereby to perform an operation on fluid in the fluid chamber or channel. The operation can comprise a mixing operation or a pumping operation. The control means can be operable to control the rate of repetition of deformation of the elastic layer. The control means can thereby control the amplitude of deformation of the elastic layer and/or the rate of pumping or mixing. The control means can be operable to control the rate of repetition of deformation of the elastic layer to be greater than a resonant frequency of vibration of the elastic layer.

In one embodiment, there is provided a method of manipulating fluid in a microfluidic system comprising coupling to a control platform a detachable microfluidic device comprising a rigid layer, an elastic layer and at least one fluid chamber or channel between the rigid layer and the elastic layer, and deforming the elastic layer thereby to manipulate fluid in the at least one fluid chamber or channel.

In one embodiment, there is provided a method of performing an operation on a fluid in at least one fluid chamber or channel of a microfluidic device, wherein an elastic layer forms at least one wall of the at least one fluid chamber or channel, the method comprising repeatedly deforming the elastic layer. The method can comprise repeatedly deforming the elastic layer and controlling the rate of repetition of deformation of the elastic layer to be greater than a resonant frequency of vibration of the elastic layer.

The invention can provide for the manipulation of fluids within microfluidic devices by means of micromechanical movements of a two-layer hybrid material, driven by a decoupled microscopic servomechanism. By a decoupled microscopic servomechanism is meant a microscopic servomechanism that is not integrated into the two-layer hybrid material. The decoupled microscopic servomechanism may be coupleable to the two-layer material.

An integrated microfluidic system including a disposable microfluidic device and a microfluidic control plate can be provided. A decoupled control unit can be provided. A system and manufacturing method for decoupled micromechanical manipulation and control of fluid flow and fluid dynamics in a microfluidic device can be provided.

The following features can be provided: 1.) two-layer hybrid microfluidic device combining a rigid polymer or other rigid layer and a deformable elastic membrane, therein to be used as a microvalve, and/or a micropump, and/or a micromixer, and 2.) decoupling of the microfluidic device from the microactuator mechanism. The microactuator mechanism can be detached from the microfluidic chip, and the microactuator mechanism can instead be housed in a separate but aligned underlying control platform. Such a design can combine the use of low-cost, disposable microfluidic devices with a re-useable microactuator-based fluid control platform, giving the potential for use in a wide range of lab-on-a-chip applications.

Microfluidic flow control may be achieved through combined use of a two-layer hybrid microfluidic device and an array of microactuators on a control platform.

FIGS. 33a and 33b show a microfluidic device 2 according to one embodiment. The microfluidic device 2 has a two layer structure comprising a first, rigid layer 4, and second deformable, elastic layer 6. In the embodiment of FIGS. 33a and 33b, the rigid layer 4 is formed of lithographically patterned SU-8 polymer 5 spin coated on a glass substrate 7. The dimensions of the rigid layer are 1 mm (width) by 5 mm (length) by 100 µm (thickness), and the elastic layer is formed of a silicone film of thickness 100 µm. The rigid layer 4 is fabricated to contain fluid flow chambers and/or channels. A single channel 8 of width 200 µm and depth 100 µm is shown in cross-section in FIGS. 33a and 33b.

The rigid and elastic layers have equivalent length and width, and are affixed together creating the two-layer device 2. First a layer of SU-8 resin is spin coated on the glass substrate 7. The thickness of the SU-8 can be precisely controlled by the spin rate. After the SU-8 is exposed to UV radiation through a mask, well-defined microstructures can be formed where the exposed area is cross-linked and unexposed area is washed away by solvent. A uniform layer of epoxy adhesive is then applied on the surface of the SU-8 resin, to which the elastic layer 6 is then adhered. Alternatively, oxygen plasma can be used to create a chemically reactive surface of the microfluidic device before elastic film is press bonded to the microfluidic device.

As shown in FIG. 33*a*, when no force is applied to the elastic layer 6, the elastic layer 6 is in its 'at rest' state and is planar, permitting fluid flow through the channel 8. When force is applied to the elastic layer 6 in the region of the channel 8, the elastic layer 6 is deformed in the region of the channel 8, thereby affecting fluid flow in the channel 8. In the example of FIG. 33*b*, the force applied to the elastic layer 6 is sufficient to cause the elastic layer 6 to contact the opposing wall of the channel 8, thereby causing the channel 8 to close. Thus the application, or removal, of force to the elastic layer 6 in the region of the channel 8 can be used to cause a portion of the channel 8 to operate as a valve.

Although FIGS. 33*a* and 33*b* show a single channel that is operable as a valve, any desired number and arrangement of channels and/or chambers can be provided in the microfluidic device, and force can be selectively applied to deform any part of the elastic layer in order to control and/or otherwise manipulate fluid flow or fluid dynamics in the chambers or channels in any way that is desired.

It is a feature of the described embodiments that the microfluidic device is detachable from a control platform that can be used to apply force to the elastic layer in order to control fluid flow within the microfluidic device.

A control platform 10 is illustrated in FIG. 34. The control platform comprises a microactuator mechanism 12 disposed on a face 14 of the control platform 10. The microactuator mechanism is linked to a controller 16 that is operable to control operation of the microactuator mechanism 12. The microactuator mechanism is operable to move a micromechanical element (indicated by dotted lines in FIG. 34). When the face 14 of the control platform is engaged with the elastic layer 6 of the microfluidic device 2, operation of the microactuator mechanism 12 causes the micromechanical element to apply a force to, and thus deform, a corresponding portion of the elastic layer 6.

The controller is, for example, a general purpose computer programmed with suitable control and interfacing software, or may be a suitable dedicated hardware device, for example comprising one or more ASICs (application specific integrated circuits).

The part of the elastic layer 6 that is deformable by the microactuator mechanism 12 can be selected by aligning the microactuator mechanism 12 with the selected part of the elastic layer 6. In the example of FIGS. 33*a* and 33*b*, the microactuator mechanism 12 is aligned with the part of the elastic layer 6 that forms a wall of the channel 8 if it is desired to open or close the channel 8. Operation of the microactuator mechanism 12 then closes the channel 8. Subsequent deactivation, or removal, of the microactuator mechanism 12 relieves the elastic layer, returning the elastic layer to a planar form, and re-enabling fluid flow in the channel 8.

The microactuator mechanism 12 can be any electromechanical or electromagnetic device controllable by application of electrical current or magnetic field to move a micromechanical element to deform the elastic layer. Any suitable, known electromechanical or electromagnetic device may be used. Alternatively the microactuator mechanism may comprise a heating or cooling device that is operable to deform the elastic layer by selectively heating or cooling parts of the elastic layer. Alternatively, the microactuator mechanism may be operable to deform the elastic layer by applying fluid pressure, for example via a pneumatic or vacuum system. The microactuator mechanism may be formed of any suitable material, including (but not limited to) silicon, glass, ceramic, metal or polymer material.

In the embodiment of FIG. 34, the dimensions of the control platform 10 match the dimensions of the microfluidic device 2. The position of the microactuator mechanism 12 on the face of the control platform 10 corresponds to the position on the microfluidic device 2 of that part of the elastic layer 6 forming the wall of the channel 8. Thus, if the edges of the control platform 10 are aligned with the edges of the microfluidic device 2, as shown in FIG. 35, and the control platform 10 and the device 2 are brought together the microactuator mechanism 12 opposes that part of the elastic layer 6 forming the wall of the channel 8, and operation of the microactuator mechanism 12 opens or closes the channel 8. Thus, a simple technique for correctly aligning the control platform 10 and the microfluidic device 2 is provided. The rigid layer 4 gives the device 2 a well-defined shape, more easily enabling precise alignment with the underlying control platform 10.

Once the control platform 10 and the microfluidic device 2 have been aligned to a desired position and coupled together so that operation of the microactuator mechanism 12 causes deformation of the elastic layer 6, they are fixed together using screws that pass through fixing holes (not shown) in the microfluidic device 2 and are screwed into threaded holes (not shown) in the control platform 10. Any other suitable fixing arrangement can be used, for example a clamp, nuts and bolts, or releasable adhesive.

In the embodiment of FIGS. 34 and 35, the control platform 10 and the microfluidic device 2 can be aligned merely by aligning their edges. In alternative embodiments, further alignment features are provided. For example, a disposable microfluidic device 22 is shown in FIG. 36, which is provided with alignment holes 24. The control platform 20 comprises four precisely positioned alignment pillars 26 located at its corners, two of which are shown in FIG. 36. The microfluidic device 22 can be precisely aligned with the control platform 20 by inserting the alignment pillars 26 into the alignment holes 24. The disposable microfluidic device 22 can be easily plugged in to and thus correctly aligned with the control platform 20.

Various alternative alignment features are provided in different embodiments. For example, in some embodiments, various different positions of a microfluidic device on the control platform are used, depending on the operations to be performed on the microfluidic device and/or the type of microfluidic device to be coupled to the platform. In some such embodiments, alignment holes are provided on both the microfluidic device and the control platform, and different alignment positions can be selected by inserting pins between different pairs of alignment holes. Although the use of alignment pillars or pins and alignment holes has been described, any type of male and female connectors can be used to align the microfluidic device and the control platform. Alternatively or additionally, alignment marks are provided on the control platform and the microfluidic device that are aligned when the control platform and the microfluidic device are in a correct position.

In the embodiment of FIG. 34, force is applied by the control platform to a part of the elastic layer of the microfluidic device by movement of a mechanical element driven by an electromechanical micro-actuator mechanism. As mentioned above, force can also be applied to deform the elastic layer by applying fluid pressure to the elastic layer, and an example of an embodiment that uses such application of fluid pressure is illustrated in FIGS. 37a and 37b. A microfluidic device 30 is shown in cross-section in FIG. 37a and comprises a fluid chamber 32 connected to a fluid channel, both formed within a rigid layer 36 of the microfluidic device 30. The elastic layer 6 forms a wall of the fluid chamber 32. The fluid channel runs in a direction perpendicular to the plane of the figure and is not shown in FIG. 37a.

A control platform 40 that is coupleable to the microfluidic device 30 for control of operation of the microfluidic device 30 is also shown in FIG. 37a. The control platform 40 comprises a fluid channel 42 that is connectable to a gas supply 44. The gas supply 44 is linked to a controller 46 that is operable to control the gas supply 44 to supply pressurised gas to the gas channel 42. An output 48 of the gas channel is provided in a face 50 of the control platform 40. An O-ring 52 is provided that is disposed on the face 50 around the output 48 of the gas channel. The controller 46 comprises at least one valve for controlling the supply of gas from the gas supply 44 and a suitable general purpose computer programmed with suitable control and interfacing software for controlling the at least one valve. The general purpose computer may be replaced by a suitable dedicated hardware device, for example comprising one or more ASICs (application specific integrated circuits).

In order to perform operations on the microfluidic device 30, the control platform 40 and the microfluidic device are aligned and fixed together as shown in FIG. 37b. The O-ring 52 is compressed between the face 50 of the control platform 40 and the elastic layer 6, and forms an air-tight connection that seals a volume connecting the output 48 of the gas channel and the part of the elastic layer 6 that covers the chamber 32.

In operation, pressurised gas is supplied by the gas supply 44 via the gas channel 42 to the sealed volume. The pressurised gas in the sealed volume applies a force to the elastic layer 6 over an area B defined by the O-ring. The pressurised gas causes the part of the elastic layer 6 forming a wall of the chamber 34, and having an area A, to deform and to cause fluid to flow from the chamber 34 into the channel. The chamber 34 and the channel form part of a microfluidic mixing device and, in operation, the controller 46 causes pressure to be applied and released from the sealed volume repeatedly in order to repeatedly deform and relax the elastic layer 6, thus contributing to a mixing of the fluid in the mixing device.

In variants of the embodiment of FIGS. 37a and 37b a vacuum, or under-pressure, rather than an over-pressure is applied to the elastic layer (for example, by pumping the sealed volume defined by the O-ring). In such embodiments, the elastic layer in its normal state can be in contact with the opposing wall of the chamber or channel and the application of the vacuum, or under-pressure, causes the elastic layer to move away from the opposing wall, opening the chamber or channel.

It is a feature of the embodiment of FIGS. 37a and 37b that the area A of the elastic layer that is deformable to cause operation of the microfluidic mixer (or other types of microfluidic control components, in other embodiments) is smaller than the area B over which force is applied to the elastic layer by the control platform 40. The use of pneumatics or other fluid pressurisation techniques to apply force to the elastic layer provides for greater tolerance in the alignment of the control platform and the microfluidic device, when the area over which force is applied is greater than the area of the elastic layer that is to be deformed to perform microfludic operations. In such embodiments, it is sufficient that the larger area over which force is applied covers, or at least overlaps, the smaller area that is to be deformed.

The microfluidic devices can be attached and detached from the control platform, and operations perfomed on the microfluidic devices, without having to change the set up of the control platform each time (the microfluidic devices and control platform can have a plug and use decoupled design). For example, for embodiments that use fluid pressurisation techniques, such as the embodiment of FIG. 37, the gas supply 44 and the controller 46 can remain connected to the control platform 50 whilst a series of microfluidic devices can be attached to and detached from the control platform 40. There is no need to reconnect gas or other inputs each time the microfluidic device on the control platform is changed.

The decoupled design means that it is relatively straightforward to perform measurements or operations on a series of microfluidic devices, using the same control components provided on the control platform. As the microfluidic devices have a relatively simple structure, are relatively straightforward to manufacture, and do not need to include complex electromechanical devices, or sensors, they can be treated as disposable, if desired.

In some cases a series of measurements can be performed by the same control platform on microfluidic devices containing a series of different fluid samples or fluid samples under a series of different conditions. In one example, a series of measurements or operations can be performed on a series of different volumes of the same sample, by attaching a series of microfluidic devices in turn, each microfluidic device having a sample chamber of a different size. The embodiment of FIG. 37, for example, is suitable for performing such a series of measurements or operations, particularly if the area of the sample chamber in each case is smaller than the area over which the force is applied by the control platform (the area contained by the O-ring in FIG. 37).

The embodiments described in relation to FIGS. 33 to 37 include a microfluidic device having a single chamber or channel on which operations are performed by deforming the elastic layer, and a control platform having a single microactuator mechanism or other feature for applying force to the elastic layer. In practice many different chambers or channels can be included on the same microfluidic device, each of which can be used to perform microfluidic operations under control of a single control platform having multiple microactuator mechanisms or other devices for applying force, or performing measurements or other operations.

An embodiment with multiple channels, and multiple locations on the control platform that are used to apply force is illustrated in FIGS. 38a to 38c, and comprises a microfluidic device 60 made of Polymer SU-8 on a glass substrate, which contains three microfluidic chambers 61, 62, 63 linked by a channel 64 having channel dimensions 200 μm (width) by 5 cm (length) by 100 μm (thickness). The elastic layer 65 is formed of bonded silicone film of thickness 80 μm. The control plate 66 is made of a plastic material, PMMA, of dimensions 3 cm (width) by 5 cm (length) by 1 cm (thickness), and contains three pneumatic components each comprising an O-ring (not shown) and a gas channel 67a, 67b, 67c and output 68a, 68b, 68c that are operable to apply force to the elastic layer 65. The pressure or vacuum applied via the outputs 68a, 68b, 68c in operation causes deformation of the elastic layer 65, which can manipulate the fluid in the microfluidic device.

The control platform can also include various components to perform operations on the fluids in the microfluidic devices. The decoupled nature of the technology enables a high degree of flexibility in the control of reactions compared to existing microfluidic devices, allowing incorporation of any active micro-components for reaction control and/or monitoring into the control platform. This may include (but is not limited to) the integration of microheaters, micromagnets, microdiodes (UV or other), and micro-optical or other detectors or sensors to the control platform for use in any kind of applications, including biomedical applications.

This flexibility also extends to the fabrication of the microfluidic device. For example, a single type of microfluidic device may be built to perform all types of reactions on multiple different control platforms, each built for a different function. Alternatively, a single control platform can be used to perform all types of reactions on multiple different microfluidic devices (also referred to as chips), each built for a different function.

For some components, for example microheaters, micromagnets, and at least some types of sensor or detector, it can be important to have direct contact or at least a minimum distance between the component and the microfluidic device, in order for the component to perform its function correctly on the fluid within the microfluidic device.

Contact, or at least a sufficiently small gap, between components of the control platform and the microfluidic device can be provided by mounting the components on the control platform with springs, elastic cushioning material or other biasing elements for ensuring that the components protrude above the face of the control platform. That can be particularly important for embodiments in which fluid pressure is used to apply force, and in which an O-ring or other sealing mechanism is used to create a seal between the face of the control platform and the microfluidic device, as O-rings or other sealing mechanisms are usually of non-negligible thickness and leave a gap between the control platform and the microfluidic device.

An example of such an embodiment is illustrated in cross-section in FIG. 39, which shows a control platform 70 for use with a microfluidic device 90. The microfluidic device is similar to that illustrated in FIGS. 37a and 37b, but includes a further chamber 92 connected to a further fluid channel. The channel and the further channel run in a direction perpendicular to the plane of the figure and are not shown in FIG. 39. The control platform 70 comprises a pressurised gas channel 72 and output 74 for applying pressure to the elastic layer 6 when coupled to the microfluidic device 30. An O-ring 76 is provided to form a seal between the elastic layer 6 and the face 78 of the control platform 70 around the output 74. The control platform also includes a further component, in this case a microheater 80 that can be aligned with, and heat fluid in, the further chamber 92. The microheater 80 is mounted on springs 82, 84. The springs 82, 84 bias the microheater 80 away from the face of the control platform 70. It can be seen from FIG. 39 that when the face of the control platform and the elastic layer of the microfluidic device are not in contact, the microheater protrudes from the face of the control platform above the level of the O-ring 76.

When the face of the control platform and the elastic layer, or other surface, of the microfluidic device are clamped or otherwise joined together, the microheater component 80 is contacted by the elastic layer 6 and is at least partially pushed into the body of the control platform until the elastic layer contacts and is sealed against the O-ring 76. Good contact is maintained between the microheater component 80 and the elastic layer 6 by the biasing effect of the springs 82, 84.

As has already been mentioned, the deforming of the elastic layer of the microfluidic device in the region of one or more fluid channels or chambers can cause the fluid channels or chambers to operate as microfluidic control components, for example valves, mixers or pumps.

The operation of a fluid channel as a valve has already been described in relation to FIG. 33. A further embodiment in which a fluid channel is operated as a valve is illustrated in FIGS. 40a and 40b, which shows in a planar view a fluid flow channel 100 of dimensions 1 mm (width) by 5 mm (length) by 100 μm (thickness) formed in a glass substrate, and that comprises a microvalve region 102. The glass substrate is covered with an elastic layer formed of SU-8 material, which forms a wall of the fluid flow channel 100. Fluid flow through the channel 100 in the microfluidic device is controlled using the microvalve region 102. Fluid can flow through the channel 100 when the microvalve region 102 of the channel is open (the microactuator mechanism of the control platform is not applied to the elastic layer, elastic layer is planar) as indicated schematically in FIG. 40a. Fluid flow through the channel is stopped as indicated schematically in FIG. 40b when the microvalve region 102 of the channel 100 is closed (the microactuator mechanism is applied to the elastic layer in the microvalve region 102, elastic layer is deformed, blocking the channel).

A micropump component can be also be formed, and uses a similar mechanism to the microvalve, based upon the application of force to deform the elastic layer so that it is forced into a fluid flow channel or chamber in the rigid layer of the microfluidic device. However, in a micropump the deformation of the elastic layer may be such as to not completely close the channel or chamber and thus not to preclude fluid flow through the channel or channel. Instead the deformation of the elastic layer of the micropump component forces the fluid to flow through or out of the channel in one or more directions.

FIGS. 41a and 41b illustrate schematically the operation of a micropump arrangement 110 implemented using a decoupled two-layer microfluidic device. The micropump arrangement 110 represented schematically in planar view in FIGS. 41a and 41b comprises a microfluidic device comprising a fluid flow channel 112 of dimensions 1 mm (width) by 15 mm (length) by 100 μm (thickness) formed in a glass substrate, and having an opening 111, 113 at each end. The fluid flow channel 112 comprises two microvalve regions 114, 116 flanking a micropump region 118 in which the fluid flow channel 112 widens to form a circular microchamber of dimensions 5 mm (diameter) and 100 μm (depth). The glass substrate is covered with an elastic layer in the form of a membrane of SU-8 material, that forms a wall of the fluid flow channel. The microfluidic device illustrated in FIGS. 38a to 38c has a geometry that is suitable for use in the micropump arrangement of FIGS. 41a and 41b.

The microfluidic device is aligned with and coupled to a control platform, such that microactuator mechanisms of the control platform are aligned with and individually operable to deform the elastic membrane at the two microvalve regions 114, 116 and at the micropump region 118.

In order to perform a pumping operation, the control platform repeatedly operates the microactuator mechanisms in a predetermined sequence. In the first stage of sequence, the microactuator mechanism adjacent to the first microvalve 114 is activated to close the first microvalve 114, whereas the second microvalve 116 remains open. The microactuator mechanism adjacent to the micropump region 118 is then activated to force fluid out of the microchamber. As the first microvalve 114 is closed, the fluid is forced along the channel 112 towards and through the second valve 116.

In the next stage of the sequence, the microactuator mechanism adjacent to the first microvalve 114 is de-activated to open the first microvalve 114, and the microactuator mechanism adjacent to the second valve is activated to close the second microvalve 116 (the microactuator mechanism adjacent to the microchamber remains activated during those operations).

The microactuator mechanism adjacent to the microchamber is then deactivated, releasing the elastic membrane adjacent at that location and pulling fluid through the opening 111 to the channel 112, and towards and through the first microvalve 114 and the microchamber, in the direction of the (now-closed) second microvalve 116.

The sequence is then repeated, to pump fluid through the channel 112 in a controlled fashion. Performing the sequence of operations in reverse pumps fluid through the channel 112 in the opposite direction.

The size of the microchamber and/or the fluid flow channel 112 can be varied in order to vary the pumping rate or other properties of the pump. For example, in variants of the embodiment of FIGS. 41*a* and 41*b*, the diameter of the microchamber varies between 0.05 mm and 5 mm in diameter.

It has been found that the pumping rate of the pump can also be varied by varying the frequency at which the sequence of stages is repeated (and thus the frequency at which the elastic membrane is deformed and allowed to relax). A graph of pumping rate as a function of frequency of operation (equal to the frequency of activation of the microactuator mechanism adjacent to the microchamber of the micropump in this case) is provided in FIG. 42. The flow rate is proportional to frequency until the frequency reaches the resonant frequency of the membrane. When the actuation frequency greater than the resonant frequency of the elastic membrane in the region of the microchamber, the maximum amplitude of deformation of the elastic membrane is not fully achieved. Therefore, the pumping volume is reduced upon further increase of the actuation frequency.

The repeated deformation of the elastic layer can also be used to provide mixing effects. In one example, the micropump of FIG. 41 can be operated as a mixer. The opening 111 of the fluid flow channel 112 is connected to one source of fluid, and the other opening 113 is connected to another source of fluid, and the fluids from the two sources are allowed to pass to the microchamber. The microactuator mechanisms are then operated to close the microvalves 114, 116. With the microvalves 114, 116 closed, the microactuator mechanism adjacent to the microchamber is then repeatedly activated at a frequency (for example, greater than 100 Hz) much higher than the resonant frequency of that part of the elastic membrane forming a wall of the microchamber (for example, the resonant frequency in the embodiment of FIG. 41 is around 10 Hz). By operating at such a frequency, the elastic layer is deformed with an amplitude (for example 5 microns) that may be smaller than the amplitude obtainable if operating at a frequency lower than the natural frequency, but that is sufficient to induce mechanical disturbance in the fluids to mix the fluids inside the microchamber. The fluids may be both be liquids, or at least one of the fluids may be a gas.

In another arrangement, a microchamber is used as a mixing chamber by repeatedly deforming the elastic layer forming a wall of the mixing chamber, as described in the preceding paragraph, but instead of the fluid being constrained to the mixing chamber by the closure of valves on both sides of the mixing chamber (for example microvalves 114, 116 described in the preceding paragraph) the microchamber is connected to an open fluid flow channel on each side and the fluid is mixed as it flows through the microchamber.

In another arrangement, each end 111, 113 of the fluid flow channel is connected to a respective microchamber. In that arrangement, the micropump is operated to alternately pump the fluids to be mixed between the microchambers in one direction and then in the reverse direction. It has been found that repeating the pumping operation in one direction and in the reverse direction more than once is sufficient to mix two fluids.

The microfluidic control components described in relation to FIGS. 40 and 41 may also be implemented in integrated microfluidic structures that comprise both fluid channels and/or chambers and components for manipulating the fluid in the channels and/or chambers. The microfluidic control components do not have to implemented in a decoupled structure such as those described in relation to FIGS. 33 to 39, in which a control platform is coupleable and decoupleable from a microfluidic device.

Various materials for use as the elastic layer have been described, but the elastic layer is not limited to being formed of such materials. Any suitable material can be used for the elastic layer, for example silicone, polyurethane elastomer, butyl rubber, nitrile rubber, ethylene acrylic elastomer, ethylene propylene rubber, natural rubber, styrene containing block copolymer elastomers, santoprene elastomer and polychroroprene elastomer. The elastic layer can be of any suitable thickness, and the most appropriate thickness may depend on the microfludic operations to be performed and on the size and arrangement of the microfluidic chambers and channels. For the embodiments illustrated in FIGS. 33 to 42, it has been found that it is desirable for the elastic layer to have a thickness less than or equal to 250 µm.

The embodiments described in relation to FIGS. 33 to 39 have included a rigid layer that is substantially rigid in its entirety. In alternative embodiments, the rigid layer comprises a substantially rigid framework and flexible or other material attached to the substantially rigid framework.

The microfluidic control platform can be formed of any suitable material, and is usually formed of a rigid material, for example glass, plastic, polymer or ceramic.

The microfluidic systems can be used for manipulation of or operations on microfluidic amounts of fluids, either gases or liquids, for any purpose. Any type of sample may be manipulated or operated on using the systems. Examples of samples include but are not limited to:—particulate matter including nano-particles, quantum dots, polymer or magnetic beads; organisms; organs; tissues (such as tumour biopsies and blood vessels); cell samples, samples of cell derived parts or substances, any cells or eukaryotic or prokaryotic origin such as primary cell cultures, stem cells and cell lines, and including animal, plant, yeast and bacterial cultures. The samples may be samples for a biological or biochemical assay such as, for example, blood, urine, saliva, cell derived part or substance (such as proteins, genes, genomes, DNA, RNA, organelles such as mitochondria or ribosome, or cell or organelle membranes).

Certain embodiments may eliminate the need to integrate microactuator components onto a microfluidic device, making device fabrication and investigation significantly less complex than existing systems, therefore lowering manufacturing costs, increasing the potential for high value manufacture, and also contributing to the disposability of microfluidic devices.

Certain embodiments open the possibility of modular microfluidic device fabrication, giving the potential to easily change and assemble custom microfluidic systems for different applications, as determined by an end user.

Magnetic means can be used for the trapping and/or mixing of nucleic acid sequences (parts) and/or oligonucleotide linker sequences (oligos) which are bound to magnetic beads in the microfluidic device. Magnetic means can also be used for the purification of nucleic acid sequences immediately prior to step (iv) of the method of the invention, as described herein.

Magnetic particles or beads can be chemically treated to make them biologically active, which causes them to bind to other biological components, such as nucleic acid sequences or oligonucleotide linker sequences, present in a reaction mixture. In one embodiment, where magnetic particles or beads are used for the purification of nucleic acid sequences, the magnetic particles or beads bind to part purification oligos, as defined herein.

When the magnetic particles bind to the desired biological components, the magnetic particles with biological components attached can be pumped through the microfluidic device, for example from the input chamber to the reaction chamber, as for a fluid. The magnetic particles can then be retained in a particular chamber, for example the reaction chamber, using a magnetic field, generally generated by a hard magnet. The magnetic particles can then be removed from a particular chamber, for example the reaction chamber, by removing the magnetic field and then pumping new fluid into that chamber to wash the beads into another chamber, for example an output chamber. In one embodiment, a magnetic field is produced manually by holding a magnet close to a particular reaction chamber and then removed by taking the magnet away from the reaction chamber.

A magnet can also be used to mix the magnetic particles with biological components attached. For example, this can be done manually by holding a magnet close to a particular chamber and moving the magnet, for example in a circular motion.

Magnetic particles can therefore be used both to purify and mix products in a microfluidic device. In one embodiment of the method of the invention therefore, the nucleic acid sequences are bound to magnetic beads and said magnetic beads are trapped and/or mixed in any one of said chambers using magnetic means.

The magnetic beads used are typically superparamagnetic nanoparticles, such as those made of iron oxide. The magnetic beads are of a size suitable for use in a microfluidic device as described herein, and so the diameter of such beads will be in the μm range, for example from 0.5 μm to 3 μm, from 1 μm to 2 μm, typically around 1 μm.

In one embodiment, the magnetic beads are coated with or covalently attached to streptavidin. In this embodiment, the magnetic beads bind to biotin which can be coupled to a nucleic acid sequence, oligonucleotide linker sequence or other oligo, such as a part purification oligo as defined herein. Streptavidin magnetic beads are available, for example, from New England Biolabs, MA.

Trapping and mixing of magnetic particles can be carried out using hard magnets such as neodymium (NdFeB) magnets, optionally including soft iron parts. In one embodiment, the magnetic means comprises rotating machined hard magnets or stacks of hard magnets with machined soft iron parts.

In this embodiment, hard magnets can be produced with very specific features such as those shown in FIG. 18 which then, by rotating the magnet, induce both trapping and mixing of the magnetic particles. The features can be cut, for example, by machining from one end using powder blasting, or a grinding process using diamond tools.

Alternatively, hard magnets can be connected to soft iron parts, on which the desired features (for example as shown in FIG. 19) have been produced, typically by machining using standard machining/milling tools. Then, the stack of hard magnet/soft iron part is rotated to induce both the trapping and mixing effect In this embodiment, commercially available amorphous magnetic foils (for example Iron or Cobalt based magnetic alloys), with very high magnetic permeabilities (for example with $\mu_r$ from $10^5$ to $10^6$), can be used to cover the machined and exposed areas of the hard magnet (see FIG. 20), to screen the magnetic field emanating from these areas. This field might actually overlap with the field generated from the upper structures, and tends to homogenize the applied magnetic field on the reaction chamber. This forces the particles to concentrate around the centre of the chamber minimizing their rotation and mixing effect. Thus the use of an amorphous magnetic foil screens the magnetic field coming from these areas which might overlap with the active field and would otherwise reduce the mixing efficiency. In one embodiment, the magnet has a teardrop shape, as shown in FIG. 20.

Alternatively, another magnet can be used to magnetize the magnetic particles, with a weaker magnetic field strength in order to allow for the driving magnetic field to act more efficiently on the particles. The magnetic field can be applied either from the bottom of the reaction chamber, by direct application or through a soft iron material, or from the sides of the chips by using large hard magnets which would allow a homogeneous magnetic field distribution around the reaction chamber.

In the case of mixing the magnetic particles in the reaction chamber covered by a flexible membrane, being sealed and having an air connection, the mixing can be further enhanced by pulsing the air connection inducing a slight deflection of the membrane, which forces the magnetic particles to interact even more with the different substances present in the chamber. This process is schematically represented in FIG. 21.

Trapping and mixing of magnetic particles can alternatively be carried out using magnetic coils, for example magnetic coils arrayed and stacked on a planar printed circuit board (PCB) platform, or manufactured by winding enamelled copper wires. In this embodiment, the magnetic means comprises magnetic coils to which a magnetic field is applied.

In this embodiment, different geometries of the magnetic coils can be used, such as rectangular or semi-circle shaped coils, arrayed and stacked together. FIG. 22 shows different geometries designed for the PCB board (FIG. 22a) and for the winding of enamelled wires (FIGS. 22b and 22c).

A simple configuration consists of a stack of two layers of coils as shown on FIG. 22. An alternative configuration is to use four layers of coils, two of which define magnetic channels for the magnetic particles to be confined to, while driving them for the other set of two.

The principle behind trapping the magnetic particles relies on the combination of two components of magnetic fields.

The first component is provided by either one hard magnet, when applied from the bottom of the chip through a soft iron part (FIG. 23a), or a stack of several hard magnets when applied from the sides of the chip (FIG. 23b). Both top and side views of the two configurations are shown on FIGS. 23a and 23b. The second component of the magnetic field applied on the magnetic particles is provided by the magnetic coils. The magnetic field gradient induced by the time varying applied electrical current crossing these coils will be enough to trap them.

In a similar manner, mixing of the magnetic particles can be performed by driving the particles in a rotational movement in the reaction chamber. This can be realized by passing a periodic square current through the coils in a sequence that allows dragging the particles from one centre of coil to the nearest one, with speeds around a few millimeters per second, until the particles make a 360° turn in the reaction chamber.

Depending on the rotation speed of the magnetic particles in the reaction chamber, this approach can be used for magnetic trapping and separation of magnetic particles; as a magnetic stirrer (at relatively low speeds up to a few hundred RPMs) to stir and mix different fluids and products in the reaction chamber; or as a magnetic mixer (at relatively high speeds more than 300 RPMs) to break the bonds in the aggregates of magnetic particles and mix them with the different liquids and reagents involved in the processes.

The method of the invention can also be used for the preparation of a combinatorial library of nucleic acid sequences.

According to a second aspect, the present invention therefore provides a method for the preparation of a library of polynucleic acid sequences, the method comprising simultaneously producing a plurality of different polynucleic acid sequences using the method of the first aspect of the invention.

In one embodiment of the second aspect of the invention, the method for the preparation of a library of polynucleic acid sequences comprises simultaneously carrying out the method of the first aspect of the invention, i.e.
(i) providing a first nucleic acid sequence N1 which has an oligonucleotide linker sequence $L1^{3'}$ at the 3'-end of the nucleic acid sequence;
(ii) providing a second nucleic acid sequence N2 which optionally has an oligonucleotide linker sequence $L2^{3'}$ at the 3'-end of the nucleic acid sequence and which has an oligonucleotide linker sequence $L2^{5'}$ at the 5'-end of the nucleic acid sequence,
wherein the 5'-end linker sequence $L2^{5'}$ of nucleic acid sequence N2 is complementary to the 3'-end linker sequence $L1^{3'}$ of nucleic acid sequence N1;
(iii) optionally providing one or more additional nucleic acid sequences N, wherein nucleic acid sequence N2 has an oligonucleotide linker sequence $L2^{3'}$ at the 3'-end of the nucleic acid sequence, and wherein said one or more additional nucleic acid sequences N comprises a terminal additional nucleic acid sequence NZ, and wherein each additional nucleic acid sequence N has an oligonucleotide linker sequence at its 3'-end, wherein said terminal additional nucleic acid sequence NZ optionally lacks an oligonucleotide linker sequence at its 3'-end and wherein each additional nucleic acid sequence N has an oligonucleotide linker sequence at its 5'-end,
wherein for the first additional nucleic acid sequence N3 the 5'-end linker sequence $L3^{5'}$ is complementary to the 3'-end linker sequence $L2^{3'}$ of nucleic acid sequence N2 and for each second and subsequent additional nucleic acid sequence N the 5'-end linker sequence is complementary to the 3'-end linker sequence of the respective preceding additional nucleic acid sequence;
and
(iv) ligating said nucleic acid sequences to form said polynucleic acid sequence;
wherein at least step (iv) is carried out on a microfluidic device;
a plurality of times with different combinations of nucleic acid sequences N, thereby producing a plurality of different polynucleic acid sequences.

In this embodiment, the method of the first aspect of the invention is carried out a plurality of times simultaneously, and the output of this method is "n" distinct samples with "n" defined assemblies, i.e. the number of samples is equivalent to the number of assemblies.

In another embodiment of the second aspect of the invention, the method for the preparation of a library of polynucleic acid sequences comprises carrying out the method of the first aspect of the invention once, but carrying out the method with a mix of nucleic acid sequences for one or each of the nucleic acid sequence N1, N2 etc.

For example, for a 3-part assembly, the method of the first aspect of the invention comprises the following steps:
(i) providing a first nucleic acid sequence N1 which has an oligonucleotide linker sequence $L1^{3'}$ at the 3'-end of the nucleic acid sequence;
(ii) providing a second nucleic acid sequence N2 which has an oligonucleotide linker sequence $L2^{3'}$ at the 3'-end of the nucleic acid sequence and which has an oligonucleotide linker sequence $L2^{5'}$ at the 5'-end of the nucleic acid sequence,
wherein the 5'-end linker sequence $L2^{5'}$ of nucleic acid sequence N2 is complementary to the 3'-end linker sequence $L1^{3'}$ of nucleic acid sequence N1;
(iii) providing a third nucleic acid sequence N3 which has an oligonucleotide linker sequence $L3^{5'}$ at the 5'-end of the nucleic acid sequence,
wherein the 5'-end linker sequence $L3^{5'}$ of nucleic acid sequence N3 is complementary to the 3'-end linker sequence $L2^{3'}$ of nucleic acid sequence N2;
and
(iv) ligating said nucleic acid sequences to form said polynucleic acid sequence;
wherein at least step (iv) is carried out on a microfluidic device.

In one embodiment of the second aspect of the invention, the method of the first aspect of the invention can be carried out using a random mixture of a number of different nucleic acid sequences, for example 3 different nucleic acid sequences to replace N1: N1a, N1b, and N1c. Each of the different nucleic acid sequences has the same oligonucleotide linker sequences $L1^{5'}$ and $L1^{3'}$. Each of the nucleic acid sequences N2 and N3 can also be replaced by a set of similar variants, e.g. N2a, N2b and N3a, N3b, N3c, N3d. All variants within each set have the same oligonucleotide linker sequence so that any assembly that includes one part from the N1 set, one part from the N2 set, and one part from the N3 set could form. For example, N1b, N2a, N3c is one possible assembly.

If the method of the first embodiment of the invention is carried out using 3 variants for nucleic acid sequence N1, 2 variants for nucleic acid sequence N2 and 4 variants for nucleic acid sequence N3, it can be seen that the resulting assembly will produce a library containing a random set of assemblies. In this example, there would be 24 possible assemblies that are generated in the combinatorial library.

In this embodiment, the output of this method is thus one randomized sample containing many different assemblies. This method can be used to create multiple different assemblies in a single reaction by varying the nucleic acid sequences at each position of the assembly as required.

The present invention also extends to the microfluidic device itself.

According to a third aspect, the present invention therefore provides a microfluidic device comprising at least one input chamber, at least one storage chamber, at least one reaction chamber and at least one output chamber and wherein each of said at least one input chamber, at least one storage chamber and at least one output chamber is linked by a separate fluid channel to said at least one reaction chamber. In one embodiment, the reaction chamber is substantially elliptical. In one embodiment, the microfluidic device comprises two input chambers, one storage chamber, one reaction chamber and two output chambers.

According to a fourth aspect, the present invention therefore provides a microfluidic device comprising at least two input chambers, at least one auxiliary chamber and at least one output chamber, wherein each of said at least two input chambers and said at least one auxiliary chamber is linked by a central fluid channel to said at least one output chamber. In one embodiment, one or more of the input chambers is linked to the central fluid channel by a further fluid channel. In one embodiment, one or more of the auxiliary chambers is linked to the central fluid channel by a further fluid channel. In one embodiment, the microfluidic device comprises two auxiliary chambers and two output chambers.

According to a fifth aspect, the present invention therefore provides a microfluidic device comprising at least one input chamber, at least one auxiliary chamber, at least one reaction chamber, at least one waste chamber and at least one output chamber, wherein said at least one input chamber is linked by a fluid channel to said at least one reaction chamber, said at least one reaction chamber is linked by a fluid channel to said at least one output chamber, said at least one auxiliary chamber is linked by a fluid channel to said at least one waste chamber, and wherein the fluid channel linking said at least one auxiliary chamber to said at least one waste chamber intersects the fluid channel linking said at least one input chamber to said at least one reaction chamber. In one embodiment, the number of input chambers is equal to the number of reaction chambers and the number of output chambers. In one embodiment, the microfluidic device comprises one auxiliary chamber and one waste chamber. In one embodiment, an additional fluid channel branches from the fluid channel that links one or more of said input chambers to one or more of said reaction chambers and joins the fluid channel that links one or more of said reaction chambers to one or more of said output chambers.

In one embodiment of the third, fourth or fifth aspect of the invention, one or more of the fluid channels has one or more valves. In one embodiment, one or more of the fluid channels has two valves and wherein a pump chamber is located between said two valves.

In one embodiment, the chambers and the fluid channels of a microfluidic device according to the third, fourth or fifth aspect of the invention are located between a rigid layer and an elastic layer and the microfluidic device is configured so that deformation of the elastic layer manipulates fluid if present in said chambers or said fluid channels.

In one embodiment, the microfluidic device according to the third, fourth or fifth aspect of the invention is part of a microfluidic system further comprising a control platform comprising means for deforming the elastic layer thereby to manipulate fluid in the at least one fluid chamber or channel.

Other features of the microfluidic device according to the third, fourth and fifth aspects of the invention are as described in relation to the first aspect of the invention According to a sixth aspect, the present invention provides a method for designing nucleic acid sequences suitable for use in a method according to the first aspect of the invention, comprising:
(i) analysing a nucleic acid sequence;
(ii) generating oligonucleotide linker sets from each nucleic acid sequence; and
(iii) checking each oligonucleotide linker set to identify conflicting linker/part overhangs, dimerization, complement binding and/or a linker-part binding region.

The input for this method is a nucleic acid sequence (or "part"). Typically, the nucleic acid sequence is in a database. In step (i) of the method of this aspect of the invention, the nucleic acid sequence is analysed. In step (ii), oligonucleotide linker sets for use in the method of the invention are generated for each nucleic acid sequence. By "oligonucleotide linker sets" is meant a pair of oligonucleotide linker sequences that bind to the 3' and 5' end of a particular nucleic acid sequence. In step (iii), each oligonucleotide linker set is checked to identify sequences that would interfere with the ability of the oligonucleotide linkers to be used in the method of the invention. Such sequences include conflicting linker/part overhangs, dimerization, complement binding and/or a linker-part binding region. The method optionally includes a further step (iv), in which if any such sequences are identified, the oligonucleotide linker sets are altered to remove any such sequences.

This aspect of the invention allows component parts to be designed so that they will be amenable to construction via the part-linker DNA assembly technology.

The method of the sixth aspect of the invention is illustrated in FIG. 29.

According to a seventh aspect, the present invention provides a method for planning the assembly of a polynucleic acid sequence from a plurality of nucleic acid sequences to be carried out by a method according to the first aspect of the invention, comprising:
(i) analysing a plurality of assemblies of a polynucleic acid sequence, said plurality of assemblies comprising different combinations of nucleic acid sequences and oligonucleotide linker sequences;
(ii) checking each of said plurality of assemblies of a polynucleic acid sequence to identify repeat parts, repeat termini and/or dimerization events; and
(iv) if repeat parts, repeat termini and/or dimerization events are identified, either correcting said assembly or warning the user that assembly correction is not possible.

This aspect of the invention allows the determination of which assemblies to construct in parallel and how to share sub-components optimally across assemblies.

The method of the seventh aspect of the invention is illustrated in FIG. 30. Exemplary inputs and outputs are shown in FIG. 31.

According to a eighth aspect, the present invention provides a system comprising means for carrying out the method according to the sixth or seventh aspect of the invention.

According to a ninth aspect, the present invention provides a computer program which, when run on a computer, implements the method according to the sixth or seventh aspect of the invention.

According to a tenth aspect, the present invention provides a computer readable medium or carrier signal encoding a computer program according to the ninth aspect of the invention.

FIG. 32 shows how the bioinformatics aspects of the invention interrelate. The different aspects shown in FIG. 32 are as follows:

The method of the sixth aspect of the invention is referred to in FIG. 32 as the Part Designer. The Part Designer queries the part database for a part sequence. Oligonucleotide linker sets are generated from the part sequence subject to the constraints in Tech Options as set out below. These constraints include the Tm of the linker-part binding region, sequence of the linker overhang, etc. If all constraints cannot be satisfied, the Part Designer reviews and modifies the failed oligonucleotide linker sets and returns the best set of oligonucleotide linkers according to priorities outlined in Tech Options. The user is warned of potential dimerization events, low Tm of complementary strands, restriction sites present in the part sequence, etc.

Pathway Generator: The user may query the part database for individual parts or sets of attributes. Part database attributes may include the type of the part (promoter, regulator, cassette, etc.), organism, start codon, etc. The user then inserts a list of parts into the desired position on the pathway. Upon submission, the Pathway Generator creates a list of all possible assemblies.

The method of the seventh aspect of the invention is referred to in FIG. 32 as the Assembly Planner. The user inputs a list of assemblies by hand or from the Pathway Generator. The Assembly Planner checks each assembly for repeat parts, repeat termini, dimerization events, etc. If found, the Assembly Planner attempts to correct the assembly by trying alternate oligonucleotide linker sets. If the Assembly Planner cannot correct the assembly, the user is warned. The user has the option of outputting an optimized assembly plan.

Tech Options: This module is a centralized repository of control options for the Part Designer, Pathway Generator and Assembly Planner. It includes both design parameters and hardware limitations. Tech Options can be input by the user.

Part Database: The Part Database stores information about parts and oligonucleotide linker sets. The user may add parts and oligonucleotide linker sets (through Part Designer) to the database.

Also provided herein is a method or microfluidic device substantially as described herein with reference to the accompanying drawings.

In another aspect, the present invention provides a method of mixing and/or trapping carried out on a microfluidic device, said method comprising using magnetic means to mix and/or trap magnetic beads in said microfluidic device. In one embodiment, the magnetic means comprises machined hard magnets or stacks of hard magnets with machined soft iron parts. In another embodiment, the magnetic means comprises magnetic coils to which a magnetic field is applied.

One embodiment of the invention is shown in Example 1. Example 1 demonstrates a 2-part assembly using the plasmid pSB1C3 and DNA encoding either GFP or RFP. Prior to carrying out the method of the invention, the parts are digested with the restriction enzyme EarI to produce the necessary overhangs. A successful assembly of pSB1C3.GFP produces green cells and a successful assembly of pSB1C3.RFP produces red cells. The parts used in Example 1 are shown in schematic form in FIG. 9.

Accordingly, in one embodiment the present invention provides a method according to the first aspect of the invention, wherein the method is as described in Example 1. In another embodiment the present invention provides a method according to the first aspect of the invention, wherein the method is as described in Example 3. In yet another embodiment the present invention provides a method according to the first aspect of the invention, wherein the method is as described in Example 4.

Preferred features of the second and subsequent aspects of the invention are as described for the first aspect mutatis mutandis.

BRIEF DESCRIPTION OF THE FIGURES

The invention will now be further described by way of reference to the following Examples and Figures which are provided for the purposes of illustration only and are not to be construed as limiting on the invention. Reference is made to a number of Figures, in which.

EXAMPLES

Example 1—2-Part Assembly on Chip

Protocols for on-Chip Assembly

The biology reactions consisted of two 2-part assemblies: RFP or GFP with a plasmid backbone pSB1C3 (pSB1C3 is also referred to herein as 1C3 or 1c3). pSB1C3 encodes resistance to the antibiotic chloramphenicol. A successful assembly of pSB1C3.GFP produces green cells and a successful assembly of pSB1C3.RFP produces red cells. The number of colonies (yield) and percent of colonies with correct phenotype (efficiency) was determined for test assemblies performed both on chip (using the microfluidic device) and off chip (in the conventional fashion with tubes and pipettes).

Figure 1:
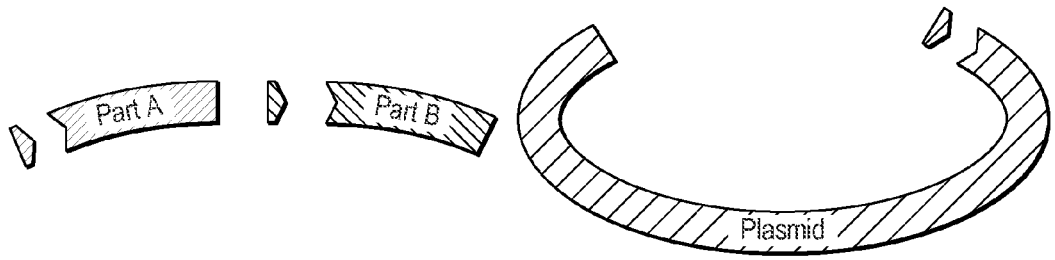
FIG. 1 is a schematic diagram of the method of the present invention. In phase 1, the parts and linkers are prepared. In phase 2, parts are ligated to appropriate linkers based on the desired pathway assemblies. In phase 3, all parts are ligated together. In this example, there are 3 parts being assembled: part A, part B and the plasmid backbone. Depending on the ligation method used, the assembly may leave a standard scar sequence between the parts (e.g. 3 bp).
Figure 1:
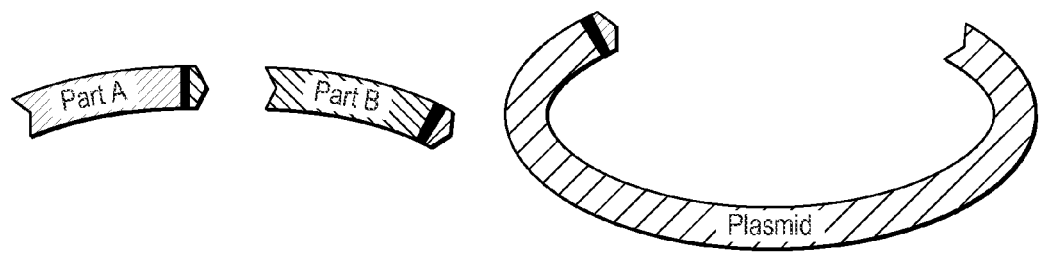
Figure 1:
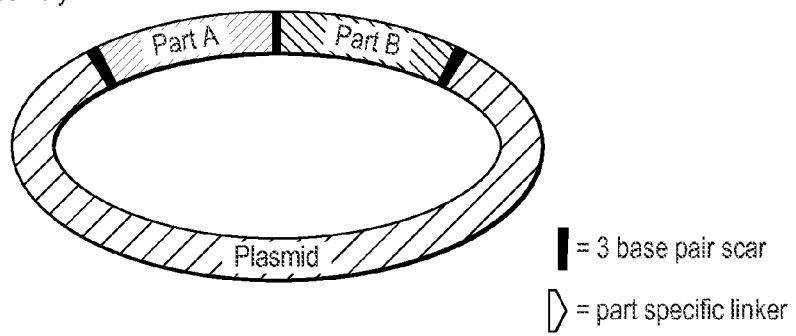
Figure 2:
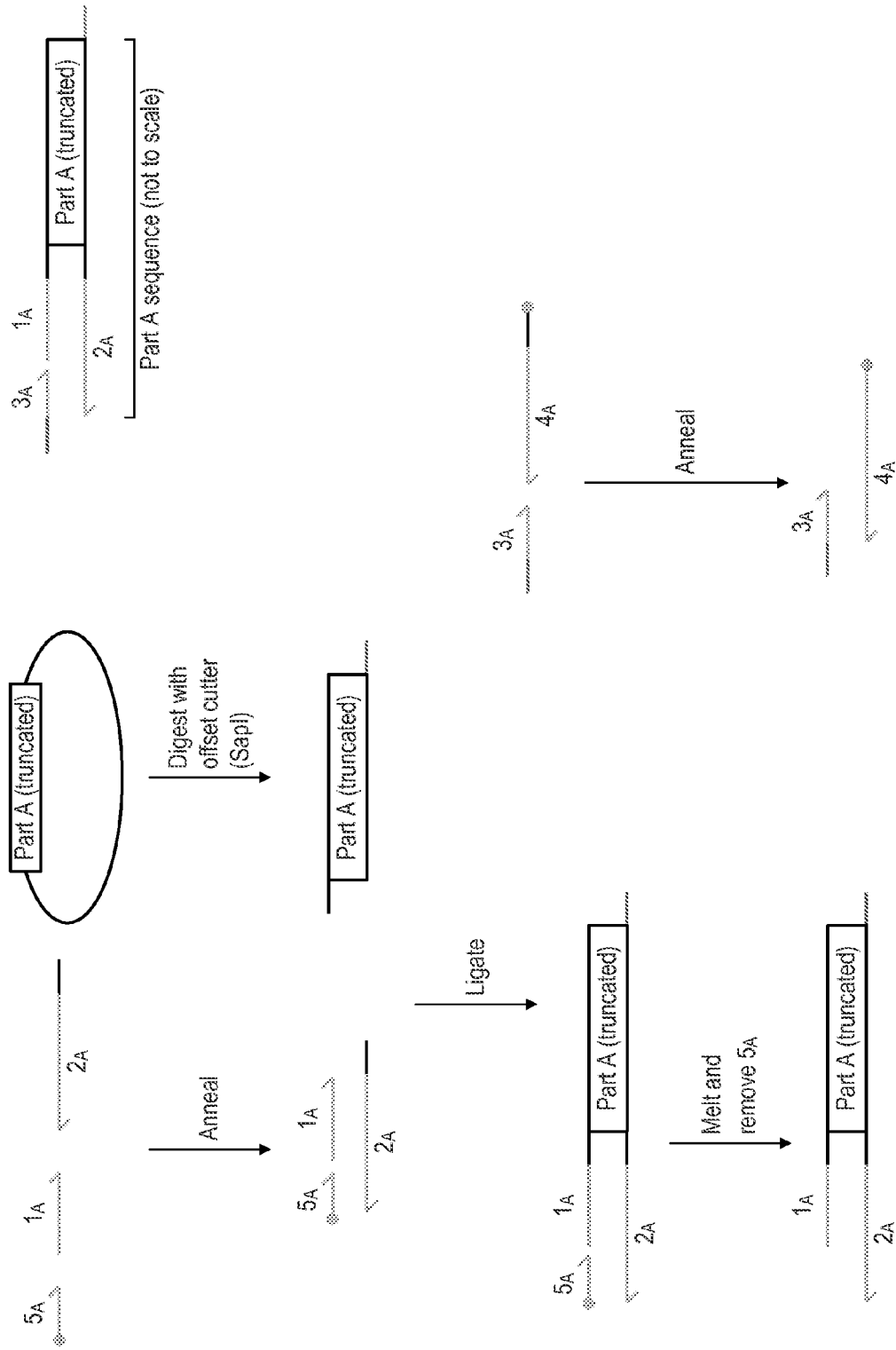
FIG. 2 is a schematic diagram of the part preparation phase of one embodiment of the invention. Parts are prepared to have overhangs and are stored with a set of oligos associated with the part. The overhang at the 3'-end of Part A (truncated) is a standard 3 bp sequence common to all parts in a library. The biotinylated oligo $5_A$ can be used for purifying the part. The biotin is represented by the circle. Oligos $3_A$ and $4_A$ are stored for use during the assembly process.
Figure 3:
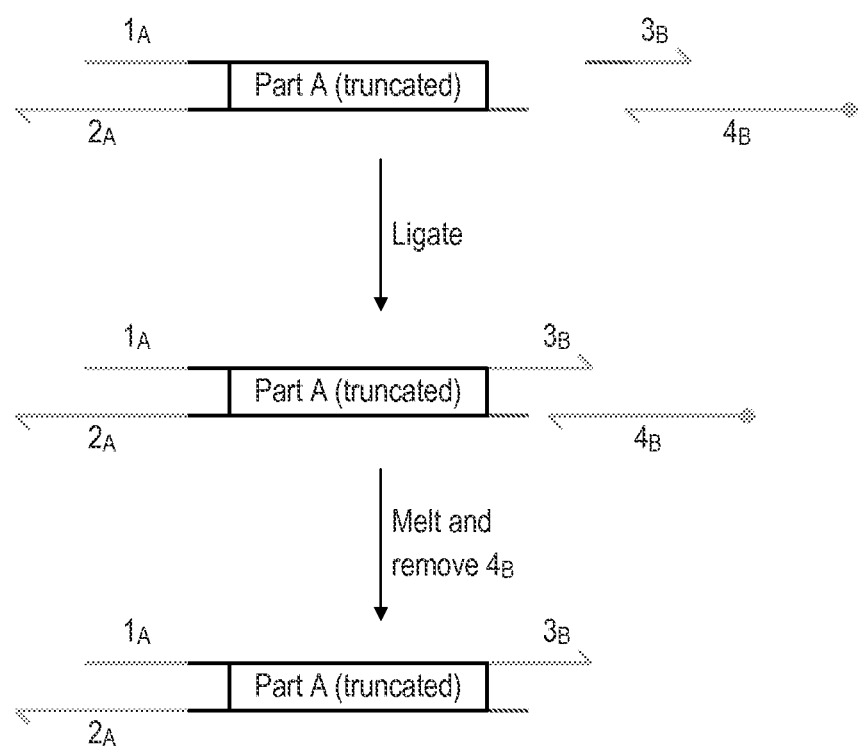
FIG. 3 is a schematic diagram of the part-linker fusion phase of one embodiment of the invention. In the part-linker fusion phase, part A is ligated with oligos for the next part B.
Figure 4:
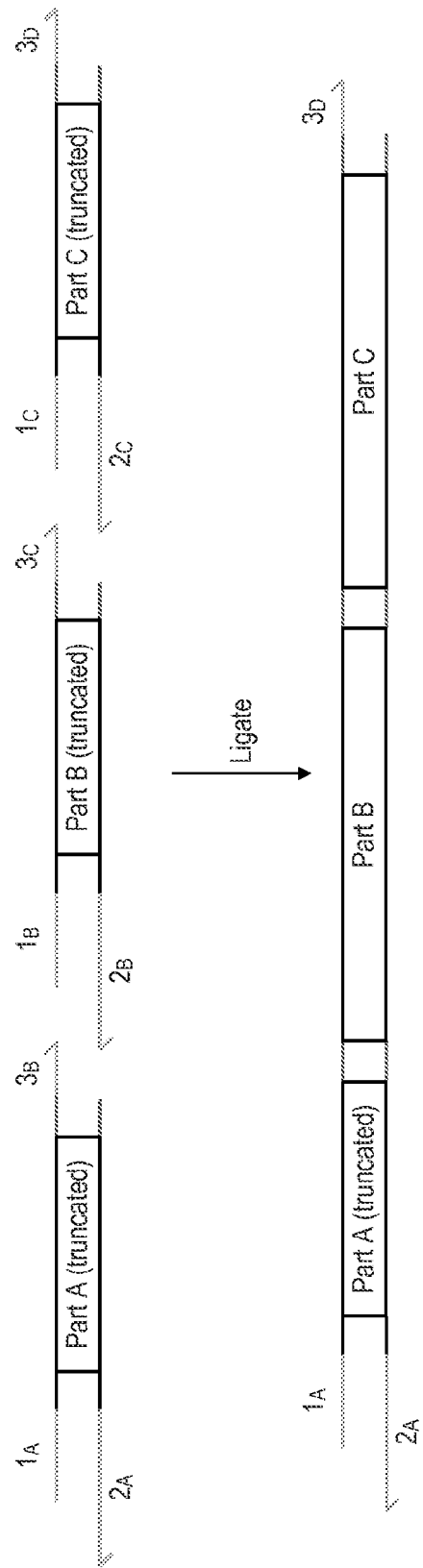
FIG. 4 is a schematic diagram of the pathway assembly phase of one embodiment of the invention. In the pathway assembly phase, part-linker fusions are ligated together.
Figure 5:
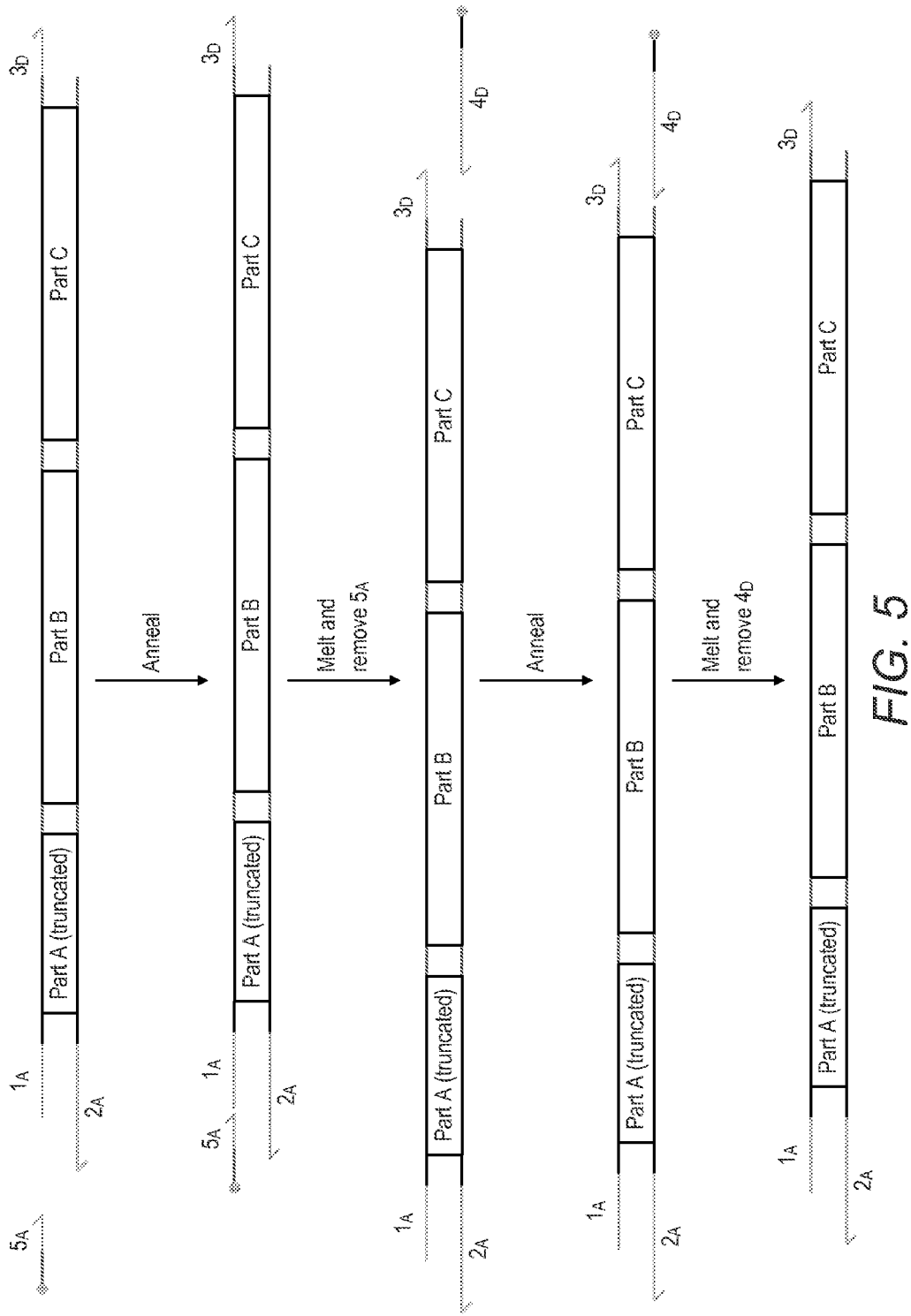
FIG. 5 is a schematic diagram of the purification of the final assembly in one embodiment of the invention. The final assembly can be purified via biotinylated oligos ($5_A$ and $4_D$). The biotin is represented by the circle.
Figure 6:
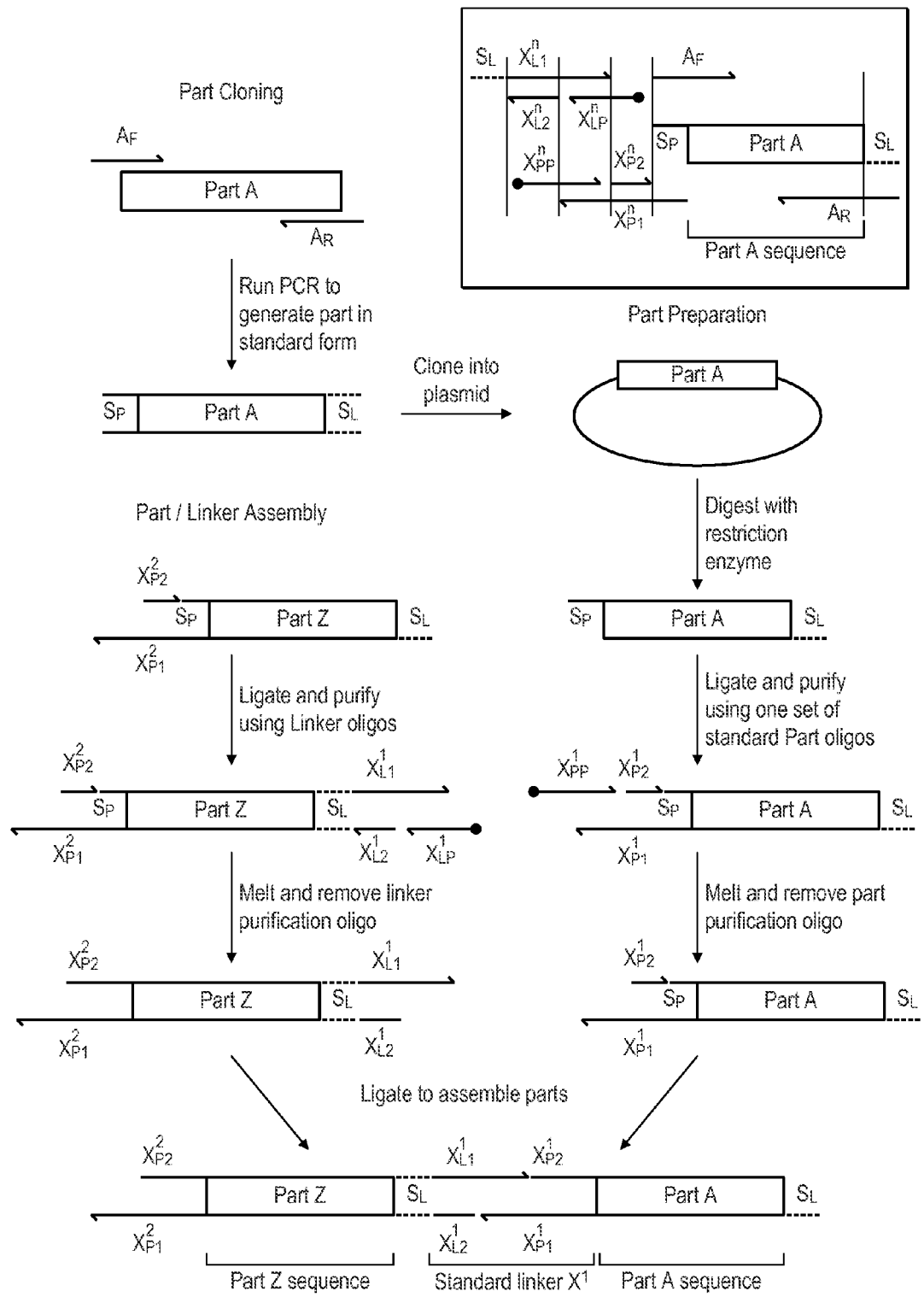
FIG. 6 is a schematic diagram of a part-linker DNA assembly scheme using partially double-stranded oligonucleotide linkers.
Figure 7:
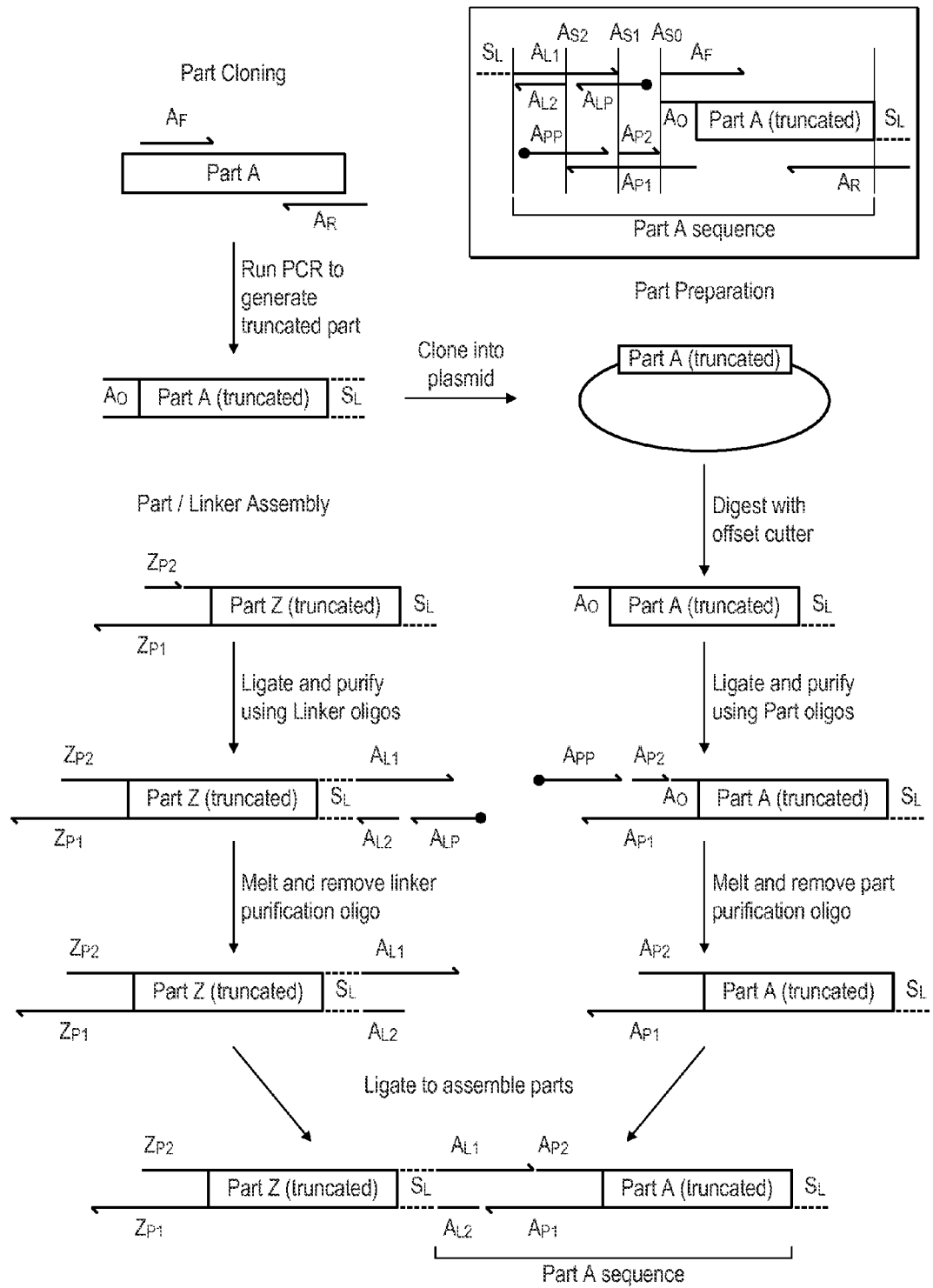
FIG. 7 is a schematic diagram of a part-linker DNA assembly scheme using partially double-stranded oligonucleotide linkers and truncated parts.
Figure 8A:
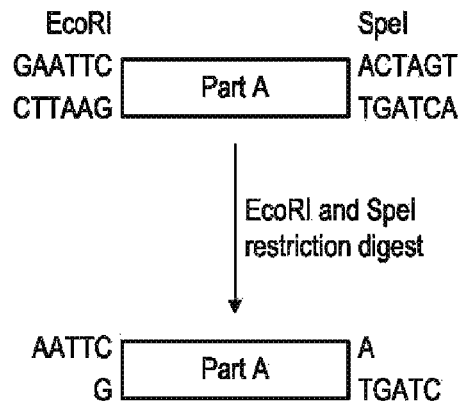
FIG. 8 shows the expected flanking sequences (overhangs) on parts following digest with (A) EcoR1/Spe1 and (B) SapI/EarI. It can be seen that the parts prepared using EcoR1/Spe1 have standard 4-bp overhangs, whilst the parts prepared using SapI/EarI have standard 3-bp overhangs.
Figure 8B:
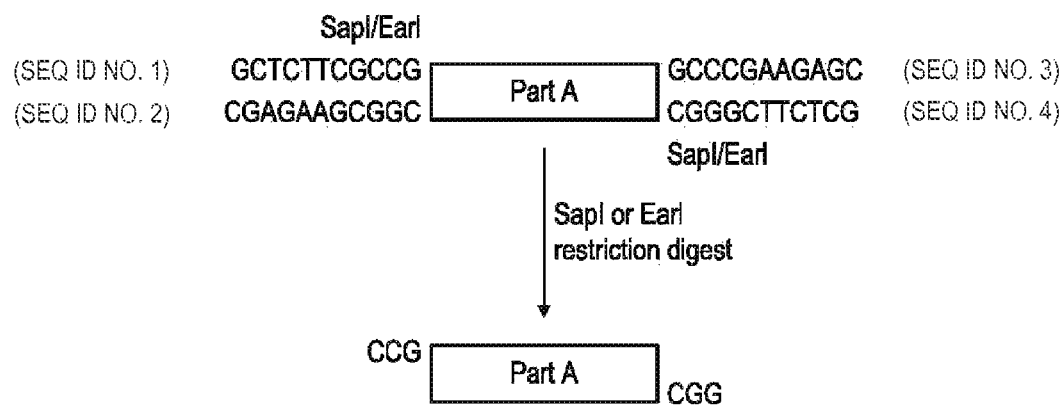
Figure 9:
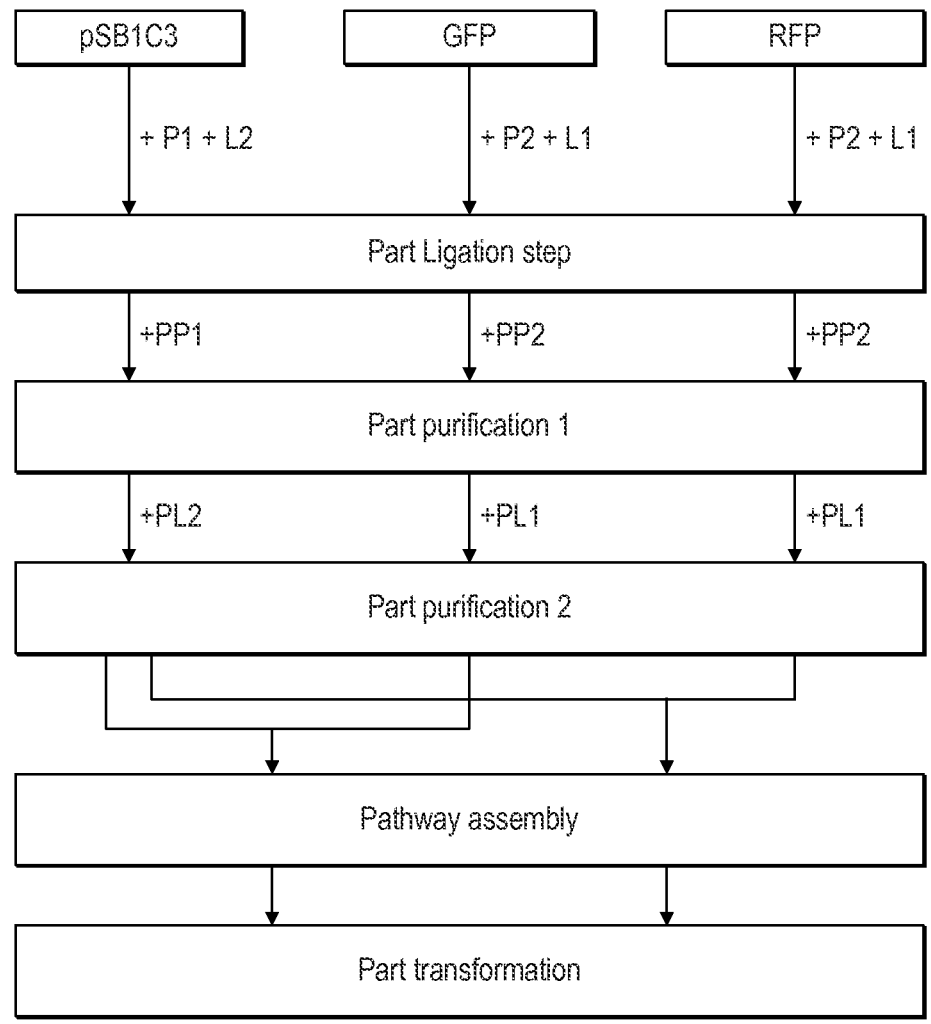
FIG. 9 is a schematic diagram of the protocol used for 2-part assemblies in Example 1.
Figure 10:
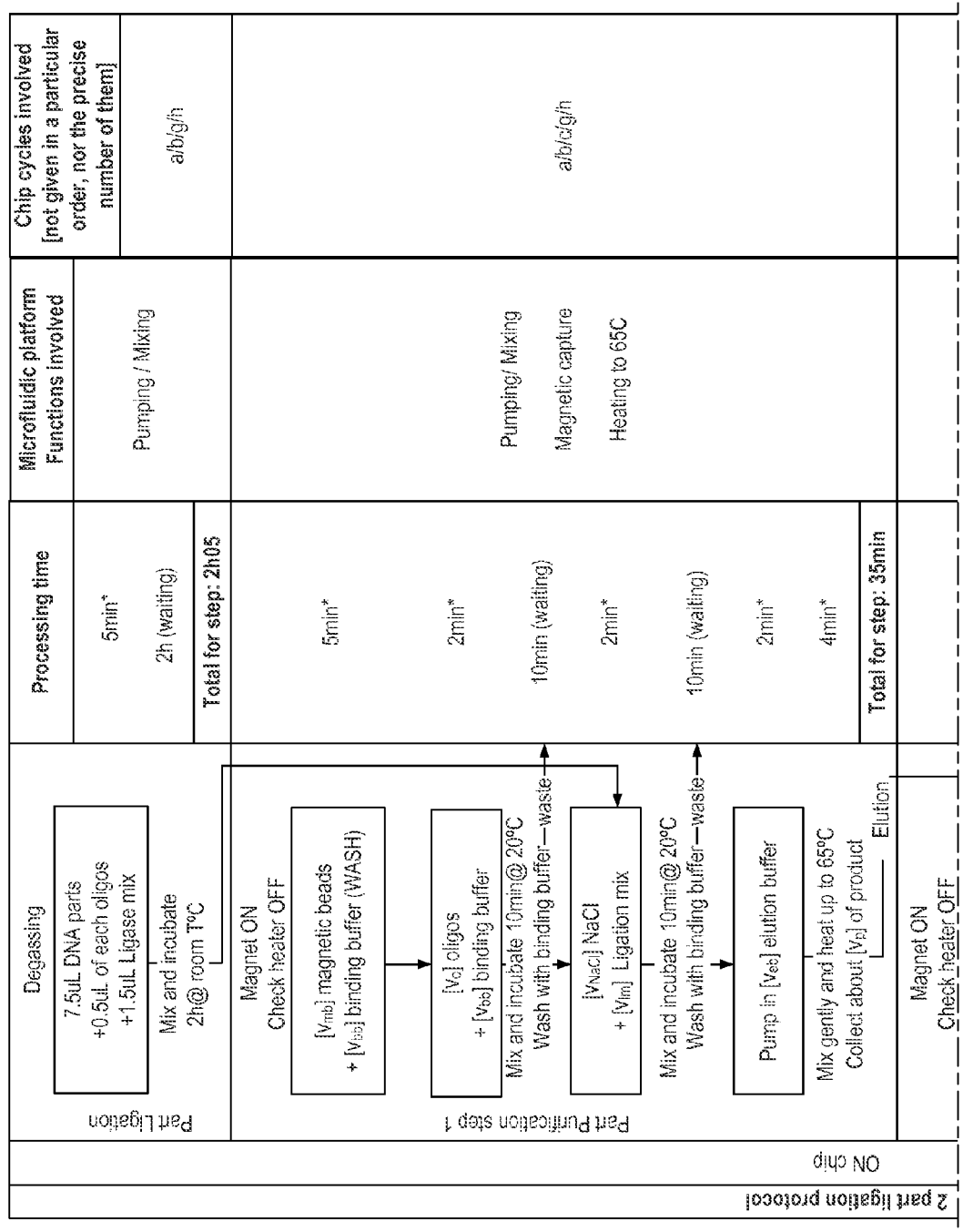
FIG. 10 shows in more detail the protocol used for 2-part assemblies in Example 1. The letters in the last column of FIG. 10 refer to chip cycles shown in FIG. 28.
Figure 10:
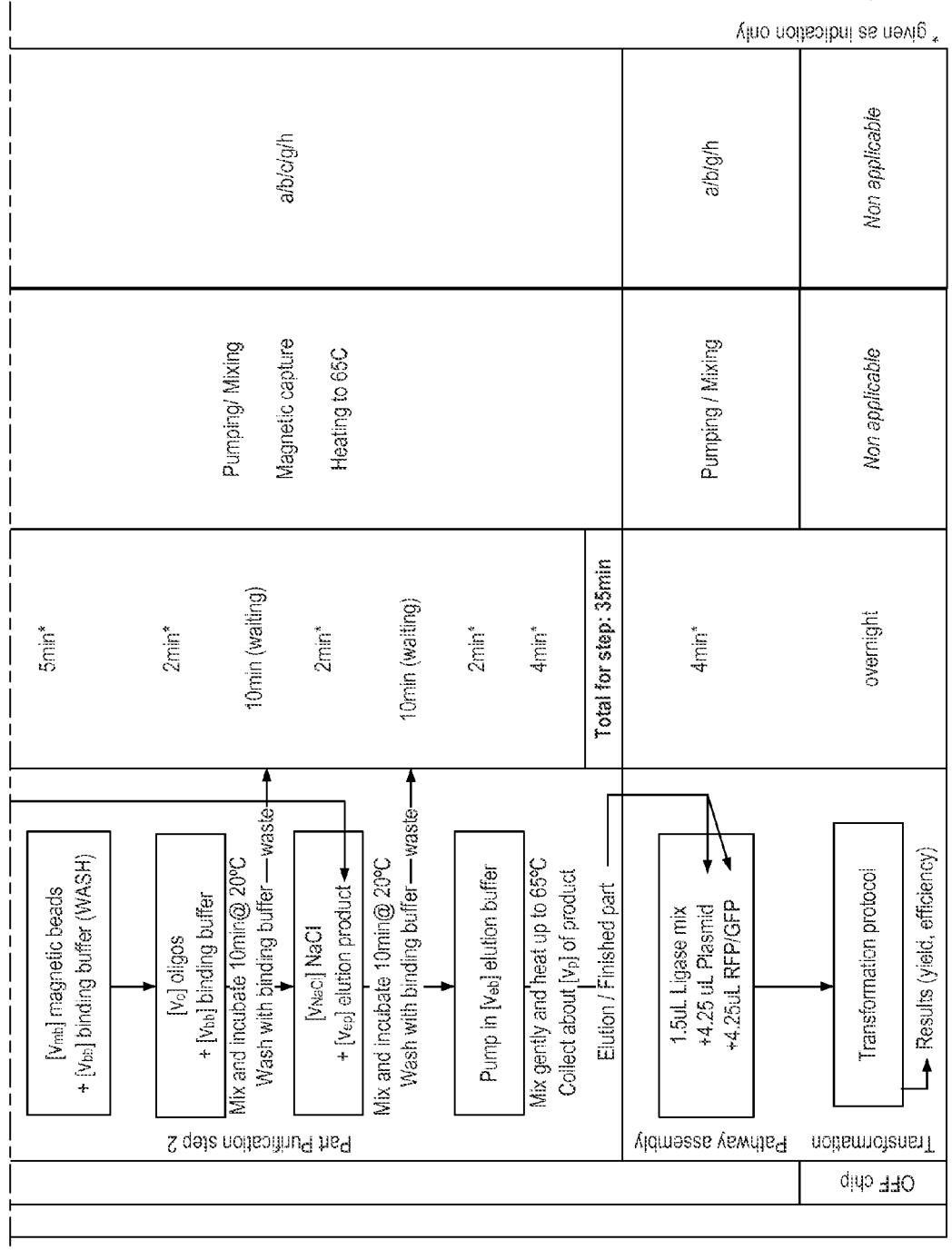
Figure 11:
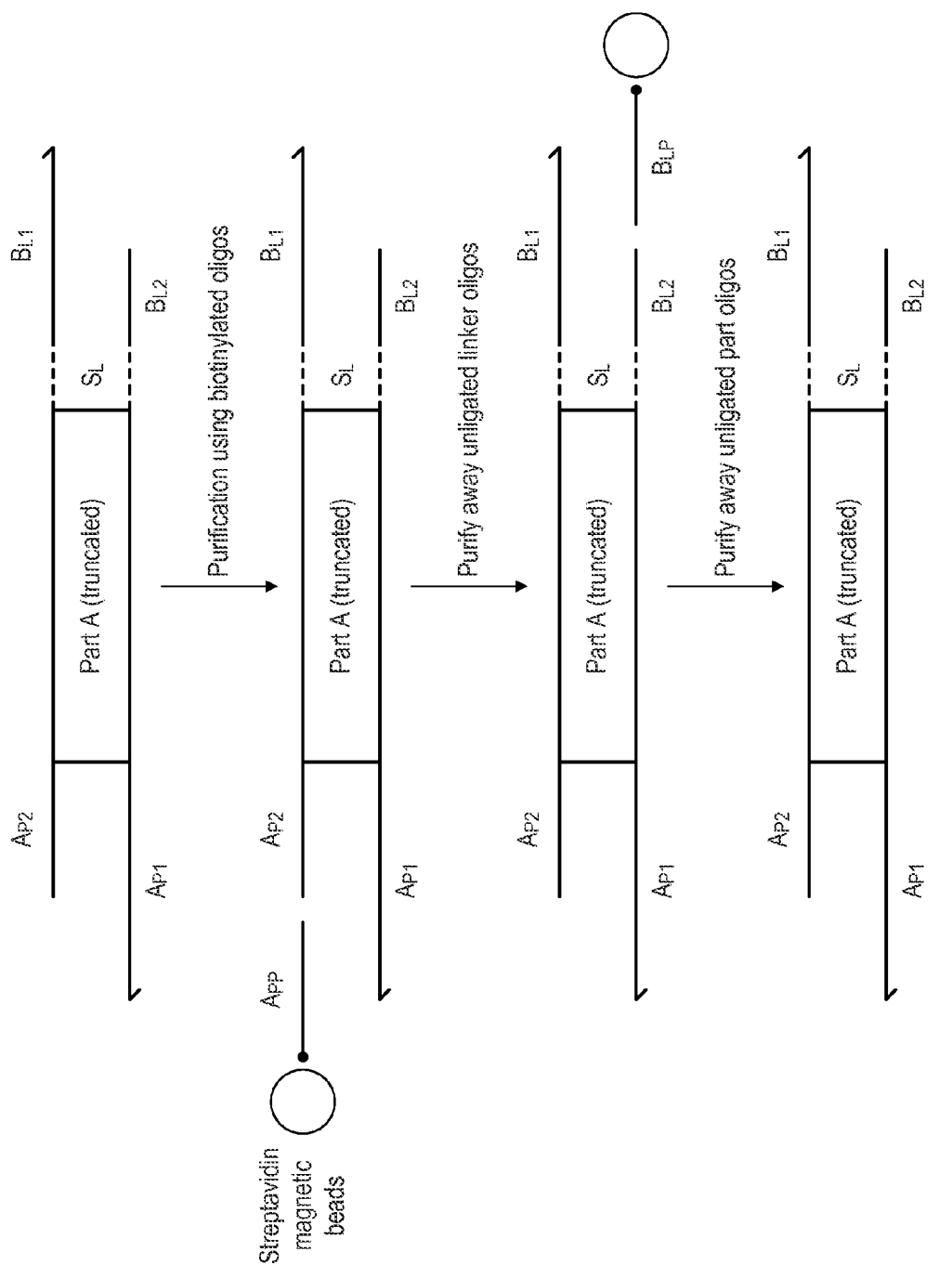
FIG. 11 shows a purification approach that can be used in the part/linker pair purification step.

The following parts (nucleic acid sequences), oligos (linkers) and reagents were used, as shown in FIGS. 9 and 10.

Pre-prepared parts:
  pSB1C3 DNA pre-digested with EarI
  RFP DNA pre-digested with EarI
  GFP DNA pre-digested with EarI
uncut pSB1C3.RFP as a positive control for transformation
2 pairs of part/linker oligos for the 2-part assemblies, P1, L1, P2, L2
matching biotinylated purification oligos for the above part/linker oligos, PP1, PL2, PP2, PL2
Buffers:
  Binding buffer: 10 mM Tris-HCl pH 7.5, 500 mM NaCl
  Elution buffer: 10 mM Tris-HCl pH 7.5
Salt solution: 4M NaCl
Ligation mix: 15 ul mix is 10 ul T4 DNA ligase buffer, 4 ul T4 DNA ligase (New England Biolabs, MA catalogue #MO202S), 1 ul EarI (New England Biolabs, MA catalogue #R0528S)
Magnetic beads: Streptavidin magnetic beads (New England Biolabs, MA catalogue # S1420S). These are 1 μm superparamagnetic particles covalently coupled to a highly pure form of streptavidin. The magnetic beads bind to the biotinylated part purification oligos.

The protocol for the on-chip method is as follows and as described in more detail in FIG. 10:

Ligations: 7.5 uL DNA parts, 0.5 uL of each oligo, 1.5 uL ligase mix

Ligations carried out were pSB1c3 with oligos P1 and L2, RFP with oligos P2 and L1, GFP with oligos P2 and L1

Mix and incubate for 2 hours at room temperature (RT)

The biological and fluidic protocols used for two-step purification of RFP and pSB1C3 parts were as follows and as described in more detail in FIG. 10 (see part purification step 1 and part purification step 2). As described below, three different protocols were used and so in FIG. 10, the volume of each reagent is indicated as [Vx], x being a subscript corresponding to the particular reagent.

Initial Protocol:
1. In a new or washed chip, 25 uL of beads are loaded in the reaction chamber and washed with 50 uL of binding buffer
2. Pump 2 uL of oligos with 10 uL binding buffer
3. 10 minutes wait at RT
4. Wash with 20 uL binding buffer
5. 15 uL ligation mix and 2 uL NaCl
6. About 10 minutes wait at RT
7. Wash with 20 uL elution buffer
8. Heat at 65 C then pump another 20 uL elution buffer
9. Collect 20 uL elution product e1
10. In a new or washed chip, 25 uL of beads are loaded in the reaction chamber and washed with 50 uL of binding buffer
11. Pump 2 uL oligos with 10 uL binding buffer
12. 10 minutes wait at RT
13. Wash with 20 uL binding buffer
14. 20 uL elution product e1 and 2.5 uL NaCl
15. 10 minutes wait at RT
16. Wash with 20 uL elution buffer
17. Heat at 65 C then pump another elution buffer
18. Collect 20 uL elution product e2

Updated Purification Protocol A
1. In a new or washed chip, 25 uL of beads are loaded in the reaction chamber and washed with 50 uL of binding buffer
2. Pump 5 uL of oligos with 10 uL binding buffer
3. 10 minutes wait at RT
4. Wash with 20 uL binding buffer
5. Pump 15 uL ligation mix and 2 uL NaCl
6. About 10 minutes wait at RT
7. Wash with 30 uL elution buffer
8. Heat at 65 C then pump another 20 uL elution buffer
9. Collect 20 uL elution product e1
10. In a new or washed chip, 25 uL of beads are loaded in the reaction chamber and washed with 50 uL of binding buffer
11. Pump 5 uL oligos with 10 uL binding buffer
12. 10 minutes wait at RT
13. Wash with 30 uL binding buffer
14. 20 uL elution product e1 and 2.5 uL NaCl
15. 10 minutes wait at RT
16. Wash with 20 uL elution buffer
17. Heat at 65 C then pump another 20 uL elution buffer
18. Collect 20 uL elution product e2

Updated Purification Protocol B
1. In a new or washed chip, 20 uL of beads are loaded in the reaction chamber and washed with 50 uL of binding buffer
2. Pump 5 uL of oligos with 10 uL binding buffer
3. 10 minutes wait at 20 C
4. Wash with 50 uL binding buffer
5. Pump 15 uL ligation mix and 2 uL NaCl
6. About 10 minutes wait at 20 C
7. Wash with 50 uL binding buffer
8. Pump 5 uL elution buffer, Heat at 65 C then pump another 10 uL elution buffer
9. Collect 10 uL elution product e1
10. In a new or washed chip, 20 uL of beads are loaded in the reaction chamber and washed with 50 uL of binding buffer
11. Pump 5 uL oligos with 10 uL binding buffer
12. 10 minutes wait at RT
13. Wash with 50 uL binding buffer
14. 10 uL elution product e1 and 2.5 uL NaCl
15. 10 minutes wait at RT
16. Wash with 20 uL elution buffer
17. Pump 5 uL elution buffer in the main chamber, heat at 65 C then pump another 10 uL elution buffer
18. Collect 10 uL elution product e2

Off-Chip/on-Chip Discrepancy:
Second wash step only for the off-chip mixture
Pathway assembly: 1.5 uL ligase mix, 4.25 uL plasmid, 4.25 uL RFP or GFP Transformation was carried out in competent *E. coli* cells (New England Biolabs, MA catalogue # C30191) following the manufacturer's protocol. When purification protocol A was followed, the transformation protocol was: 5 uL ligation in 50 uL cells with 800/900 uLs SOC medium. When purification protocol B was followed, the transformation protocol was: 2 uL of ligation in 50 uL cells with 300 uL SOC medium. The transformed cells were plated out onto plates containing the antibiotic chloramphenicol and the outcome of the experiments determined by counting the number of colonies (yield) and percent of colonies with correct phenotype (efficiency). A successful assembly of pSB1C3.GFP produces green cells and a successful assembly of pSB1C3.RFP produces red cells.

Microfluidic Device and System

The method of the present invention is carried out on a microfluidic device. In the experiments described in this Example, the biological parts, liquids and reagents were first loaded onto the microfluidic chip. Then, an automated control unit platform, based on air and pneumatic valve actuation, allowed the user to perform all the biological manipulations and reactions on chip. At the end of the process, the biological products were then collected from the outputs.

Figure 12:
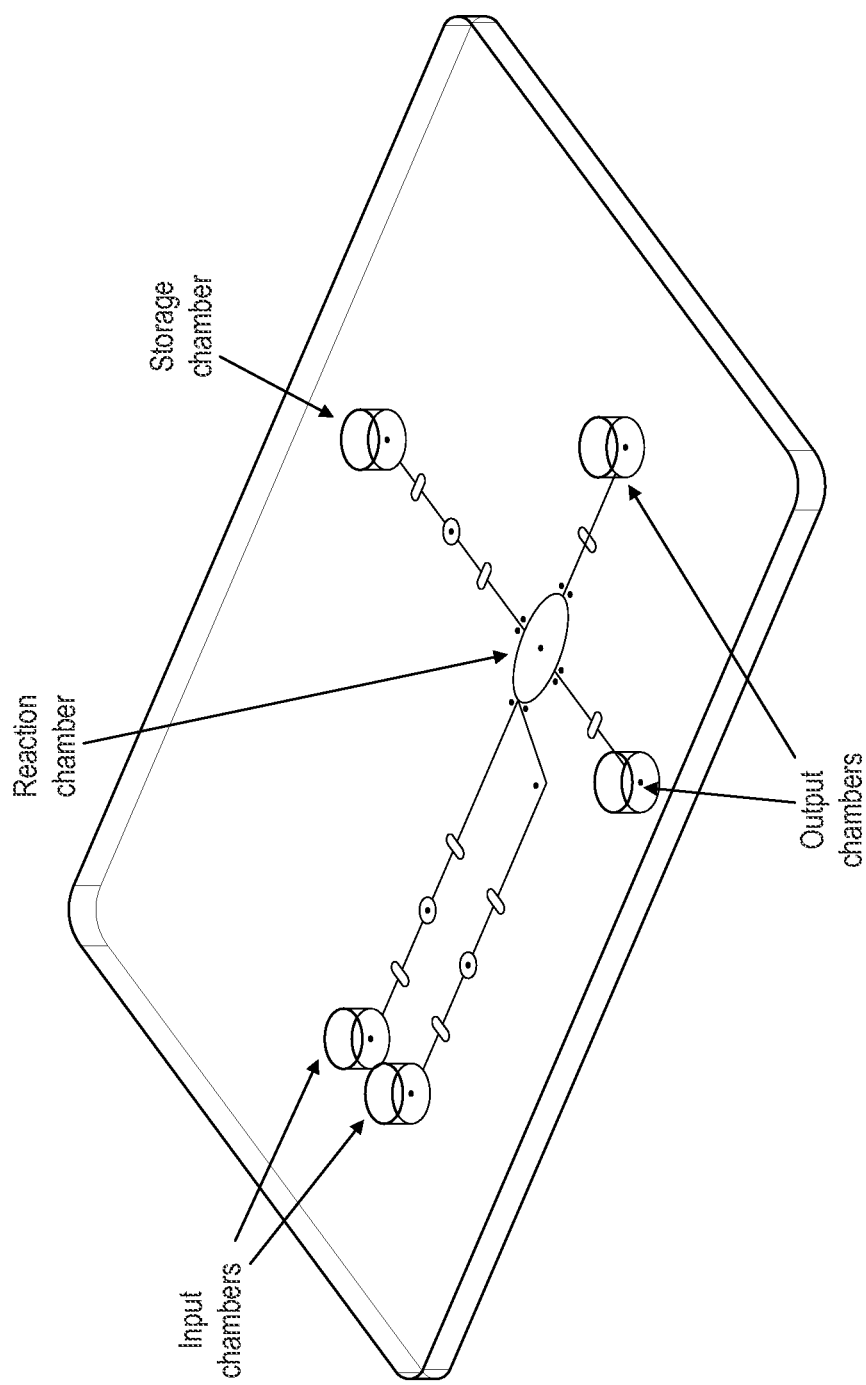
FIG. 12 shows the 3D layout of the microfluidic device used in Example 1. The two input chambers have parallel fluid channels linking them to the central elliptical reaction chamber. The fluid channels of the two input chambers have two valves and a pump chamber. The storage chamber has a fluid channel linking it to the central elliptical reaction chamber. The fluid channel of the storage chamber also has two valves and a pump chamber. The two output chambers are linked by a fluid channel to the central elliptical reaction chamber. Control of the device is provided by 12 air channels, one temperature control and one magnetic part.
Figure 13:
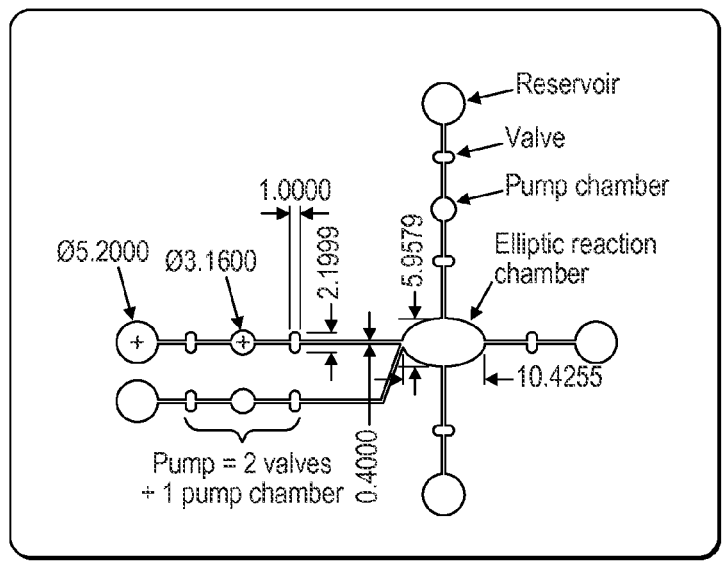
FIG. 13 shows the dimensions of the microfluidic device used in Example 1.
Figure 13:
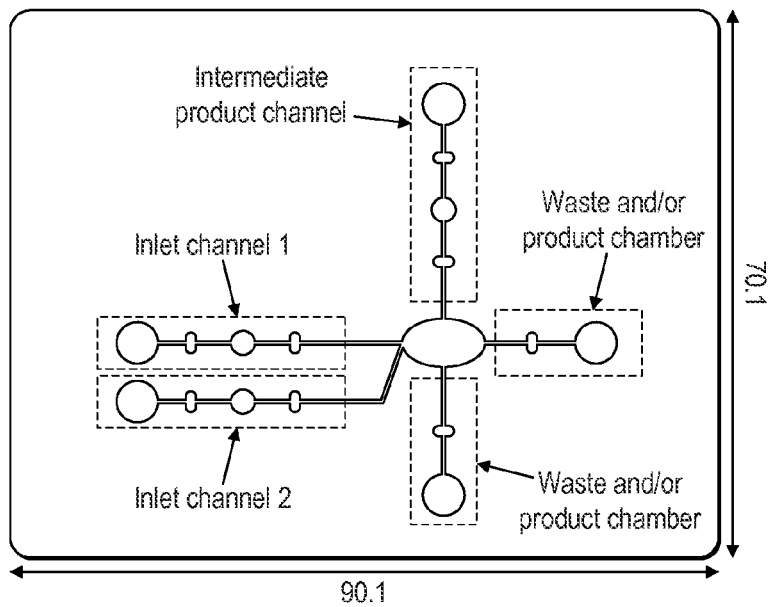

The microfluidic device used in this Example has a number of microfluidic functions. In addition to the basic microfluidic functions of pumping and mixing, the microfluidic device also has heating and magnetic control functions. The basic 3D layout of the microfluidic device used in this Example is shown in FIG. 12, and FIG. 13 shows the dimensions of the microfluidic device. The device contains two input chambers, two output chambers (for waste and/or products) and one storage chamber (temporary holding chamber or reservoir) with fluid channels linking each of these chambers to a central elliptical reaction chamber. Each "pump" unit for the two input chambers and the storage chamber feature two valves and one pump chamber, as shown in FIG. 13. The storage chamber allows the storage of product whilst flushing the reaction chamber. As can be seen from FIG. 13, the depth of all of the structures (chambers, channels etc) is 250 μm and the dimensions of the microfluic device are 70.1 mm×90.1 mm.

As shown in FIG. 13, the inlet channel 1 comprises the first input chamber, together with its two valves and one pump chamber, the inlet channel 2 comprises the second input chamber, together with its two valves and one pump chamber, the intermediate product channel comprises the storage chamber (temporary holding chamber or reservoir), together with its two valves and one pump chamber, and each of the two waste and/or product chambers comprises an output chamber together with its valve.

Figure 28:
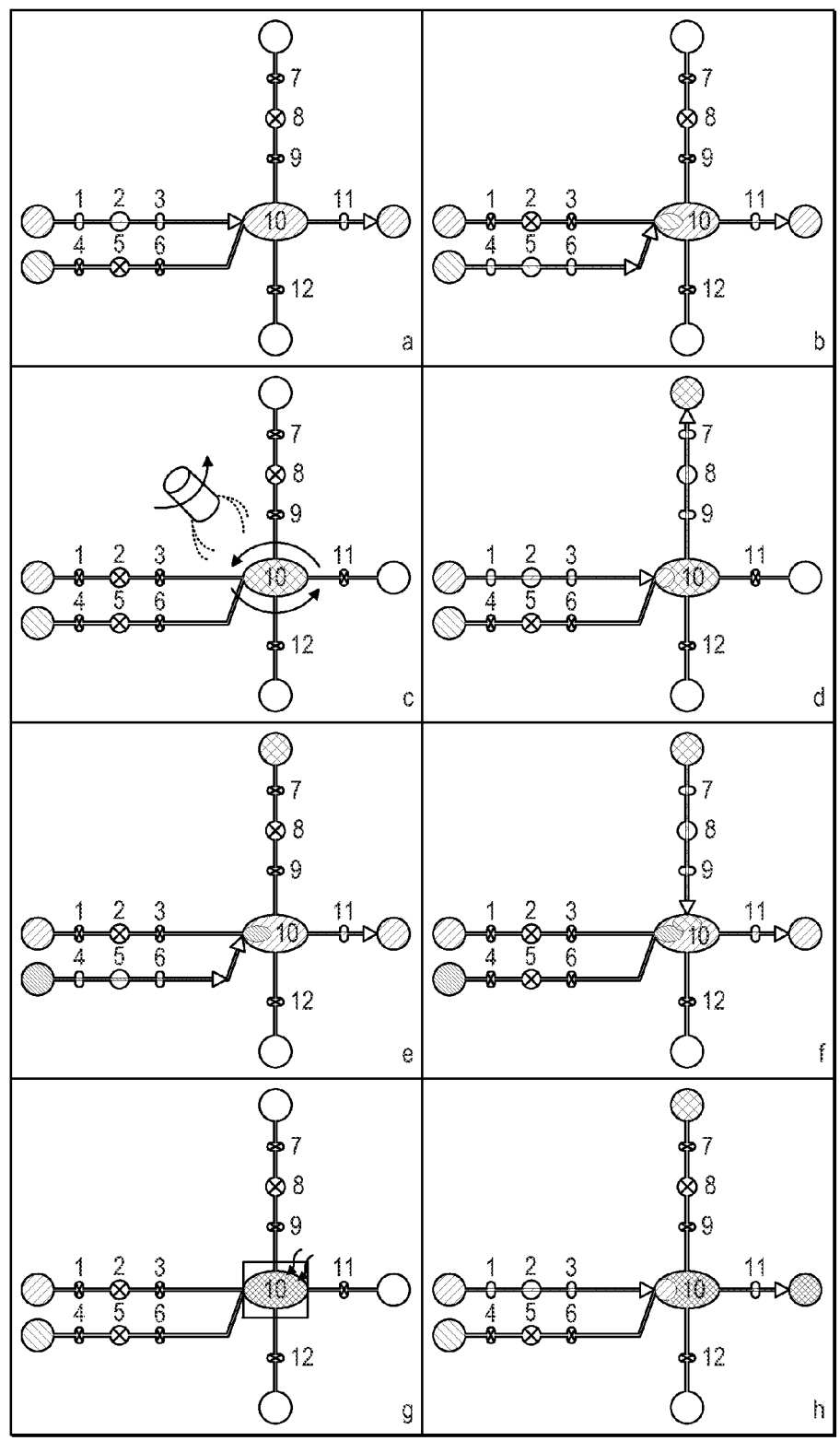
FIG. 28 summarises a number of different fluidic steps that were used in Example 1.
Figure 29:
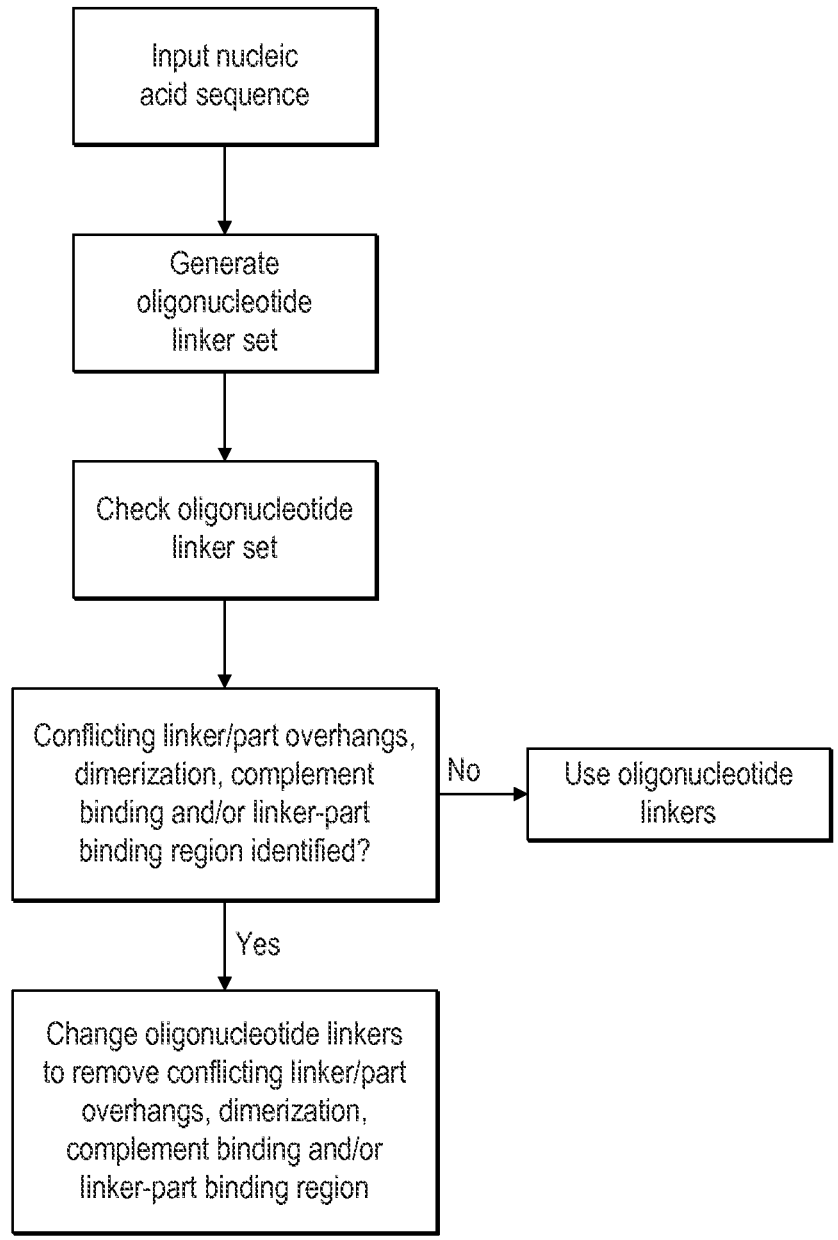
FIG. 29 is a flowchart of the method of the sixth aspect of the invention.
Figure 30:
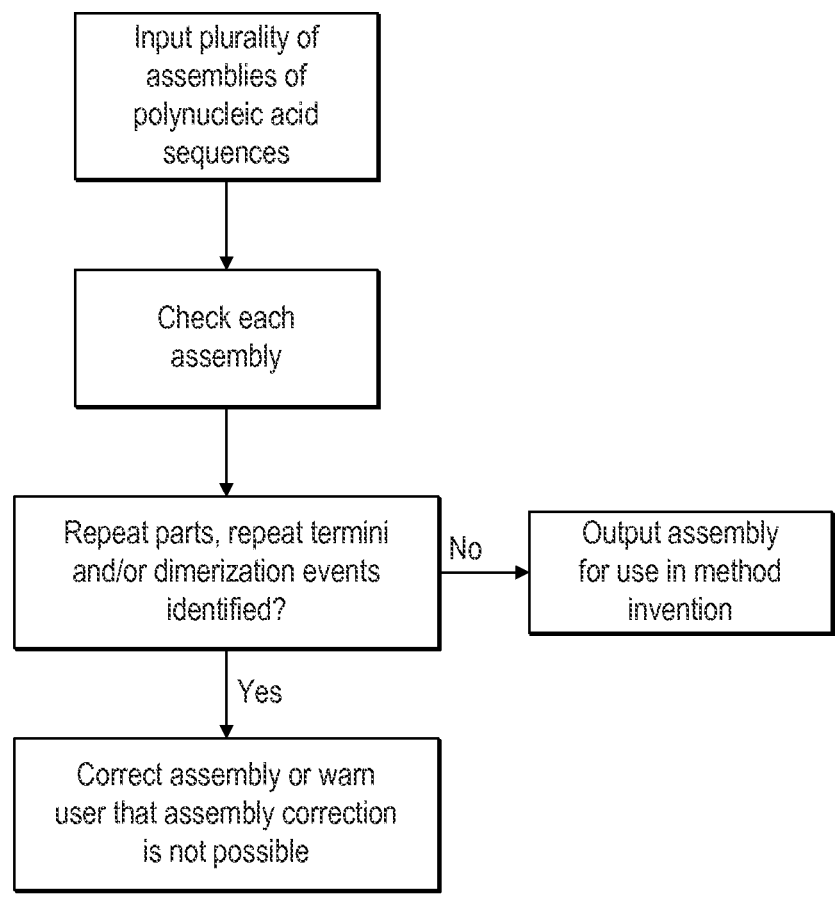
FIG. 30 is a flowchart of the method of the seventh aspect of the invention.
Figure 31:
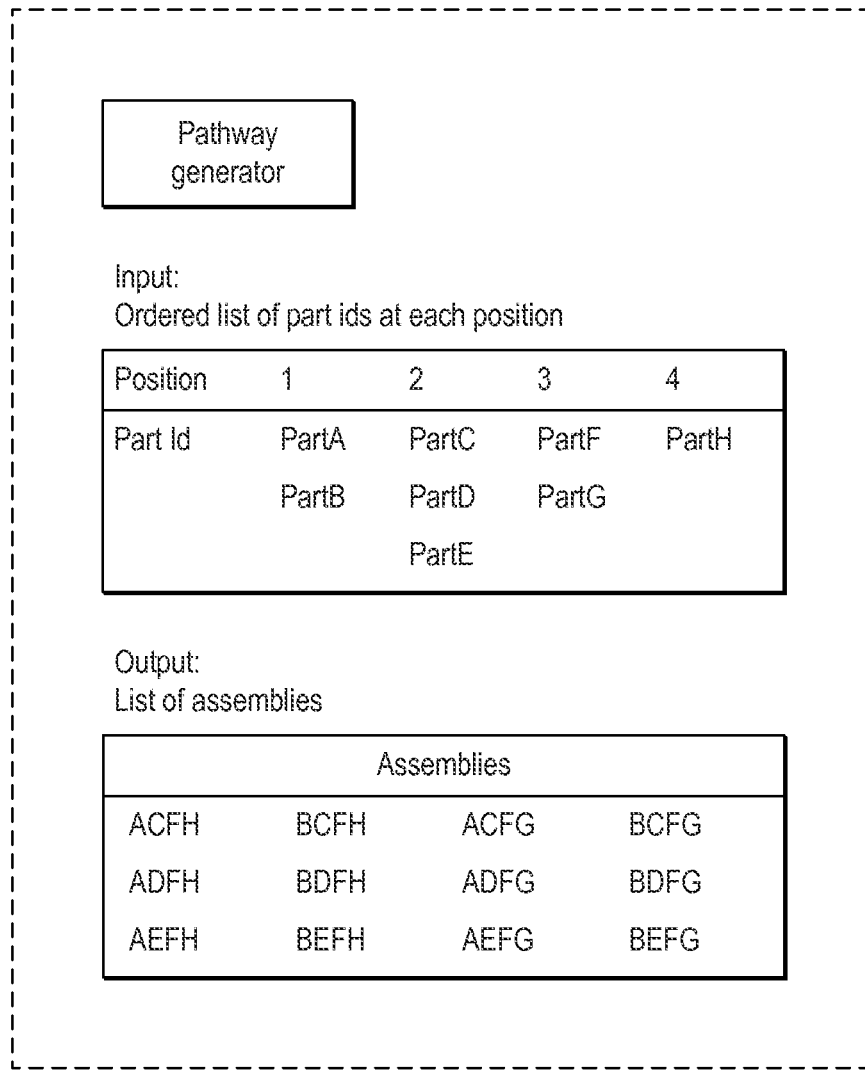
FIG. 31 shows exemplary inputs and outputs of the seventh aspect of the invention.
Figure 32:
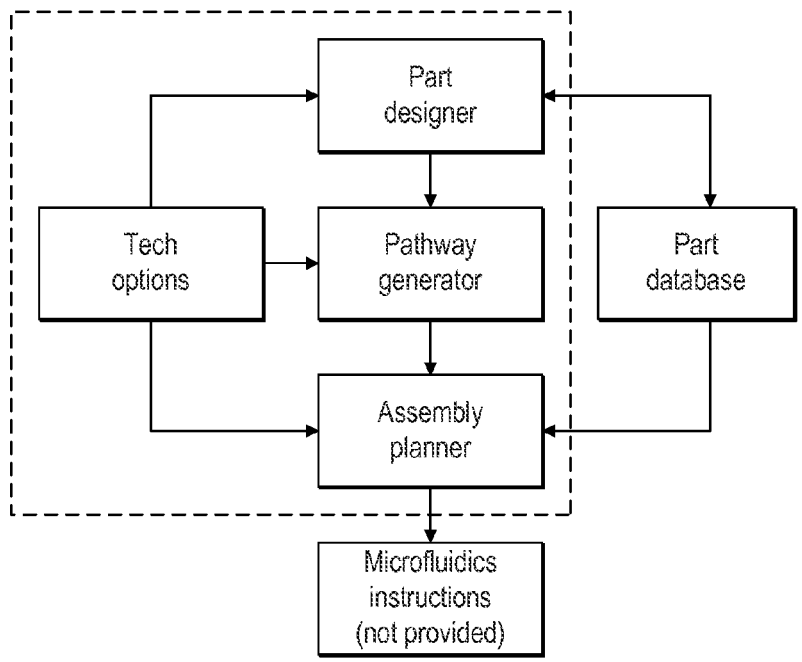
FIG. 32 is a schematic of the bioinformatics aspects of the invention.
Figure 33A:
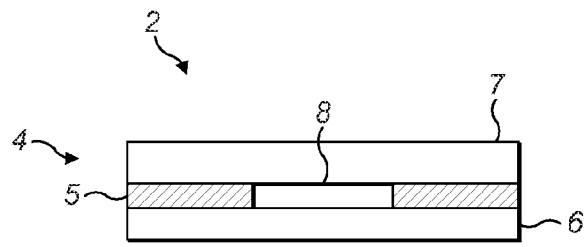
FIGS. 33a and 33b are schematic illustrations of a microfluidic device according to one embodiment.
Figure 33B:
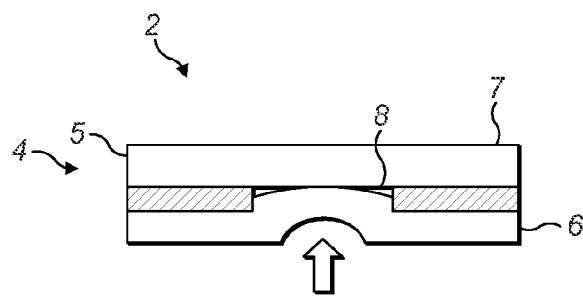
Figure 34:
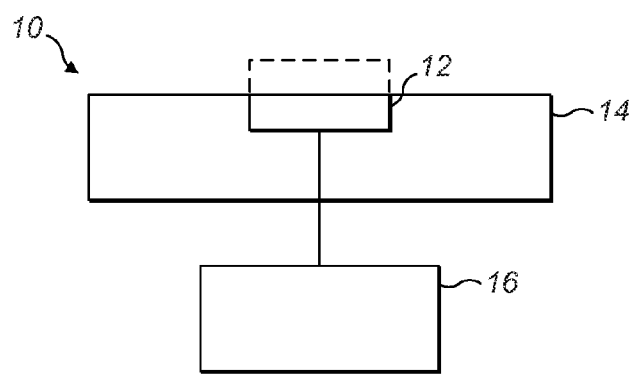
FIG. 34 is a schematic illustration of a control platform.
Figure 35:
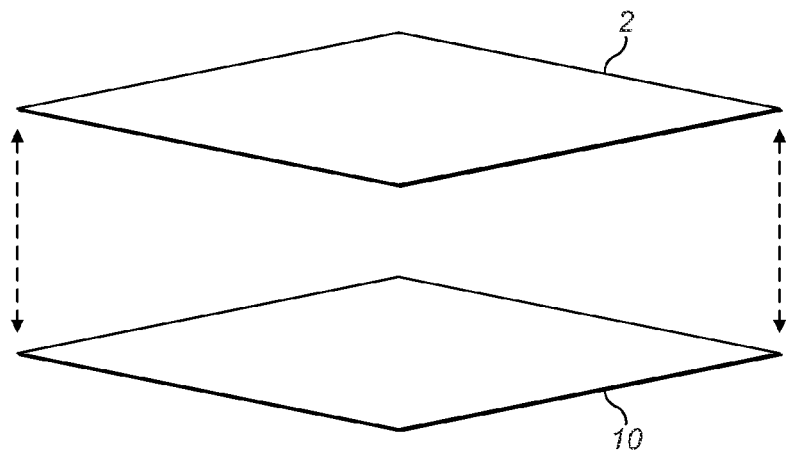
FIG. 35 is a schematic illustration, in perspective view, of the microfluidic device and the control platform.
Figure 36:
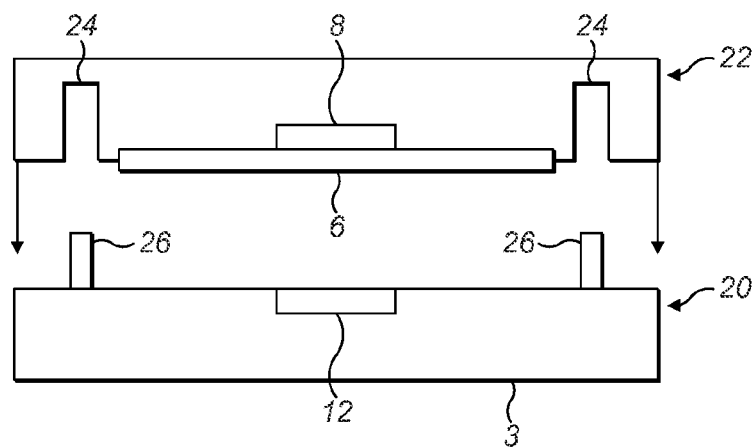
FIG. 36 is a schematic illustration of a microfluidic device and a control platform, which include alignment holes and pillars.
Figure 37A:
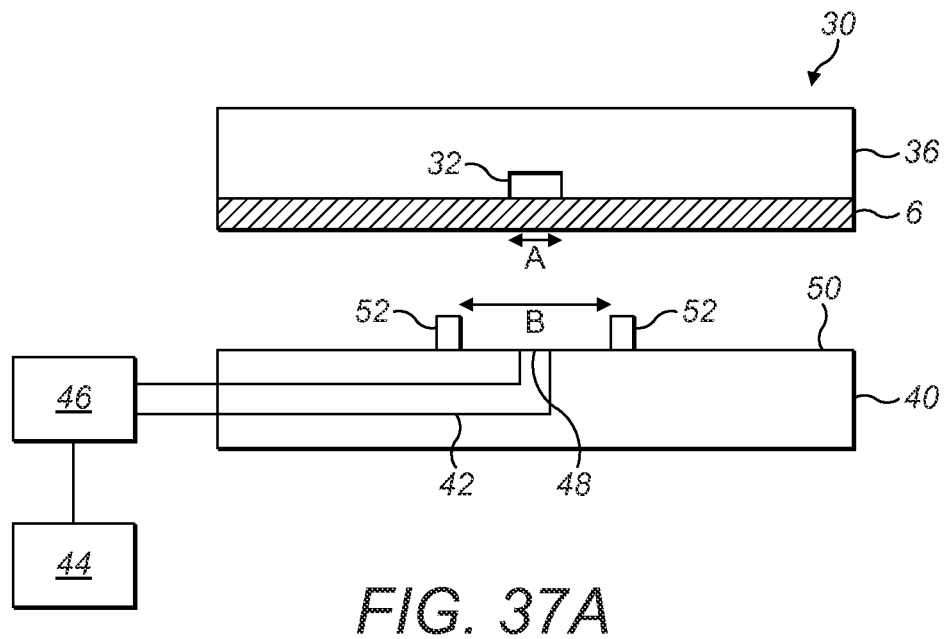
FIGS. 37a and 37b are schematic illustrations a microfluidic device and a control platform in a further embodiment.
Figure 37B:
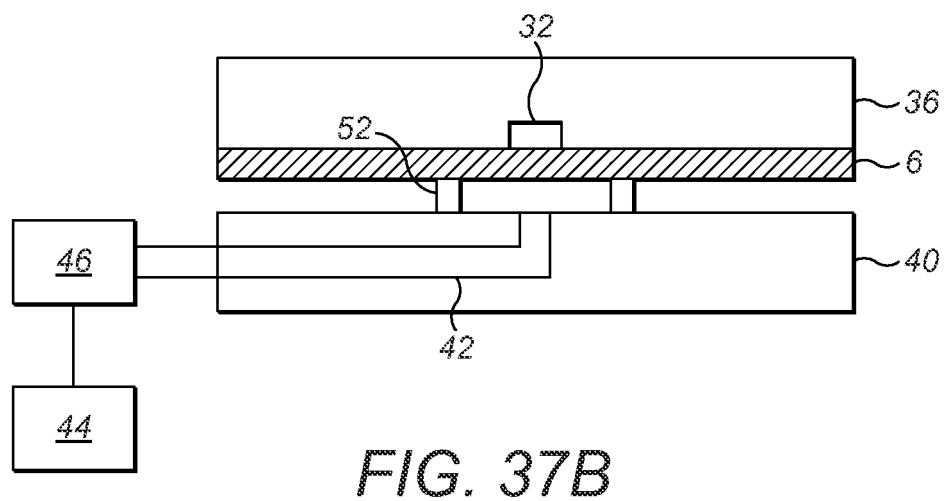
Figure 38A:
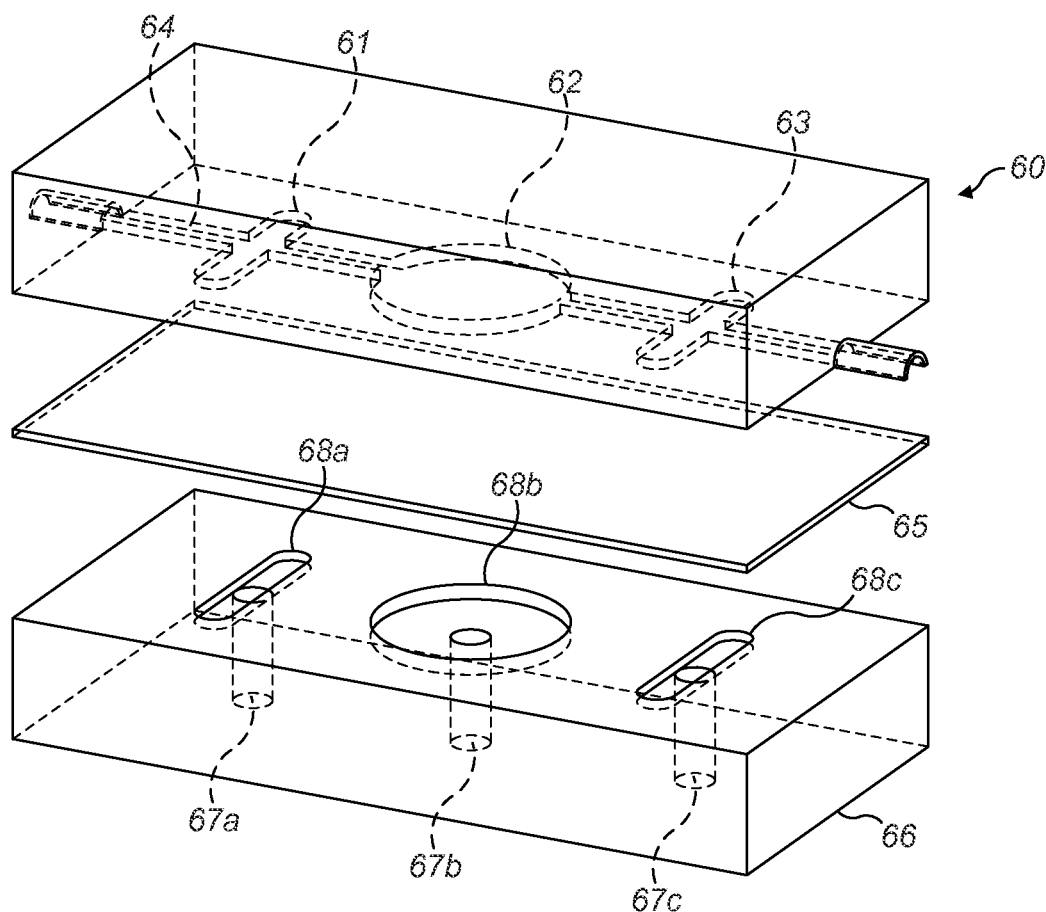
FIGS. 38a to 38c are schematic illustrations of a microfluidic device and a control platform according to a further embodiment.
Figure 38B:
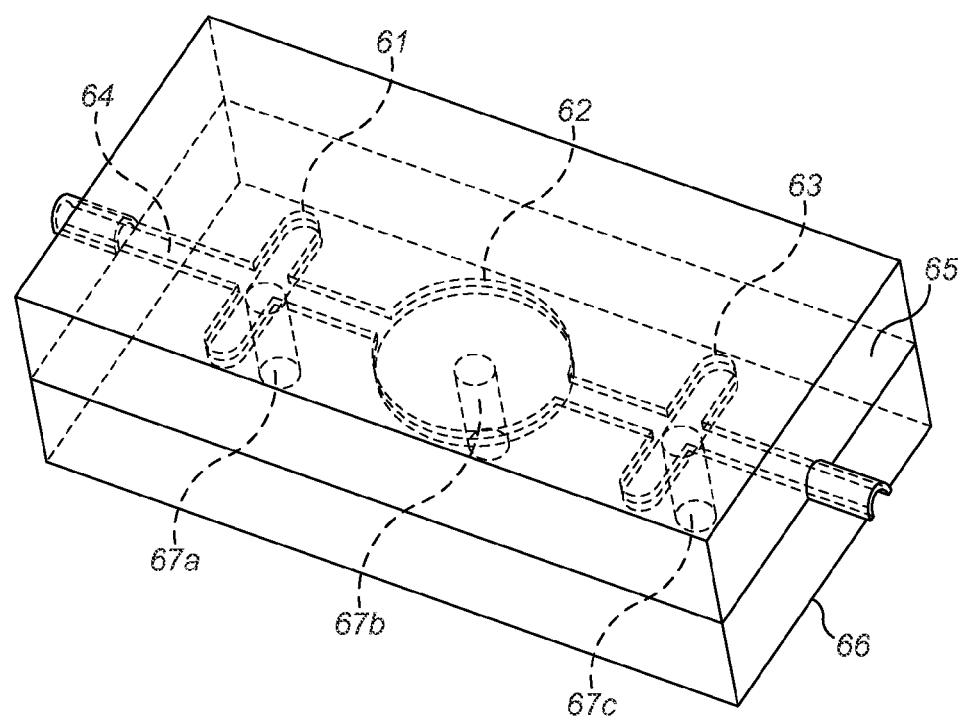
Figure 38C:
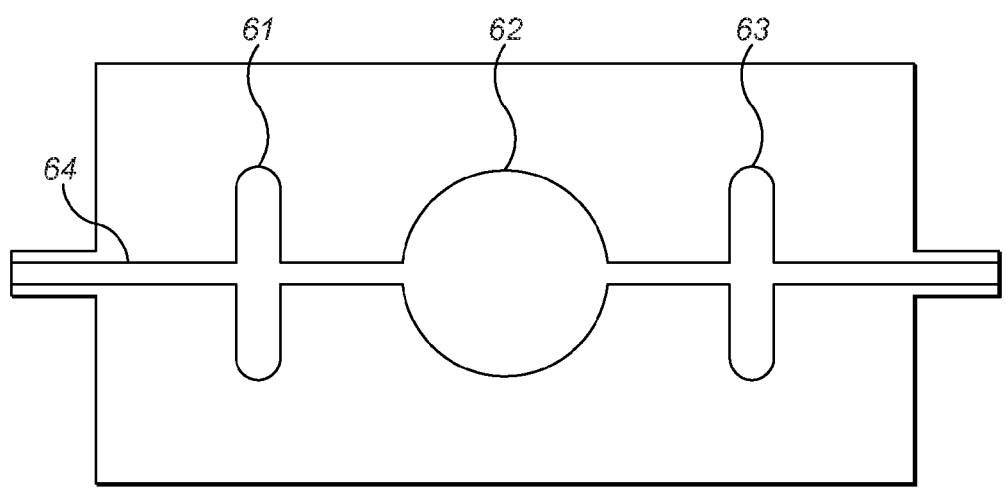
Figure 39:
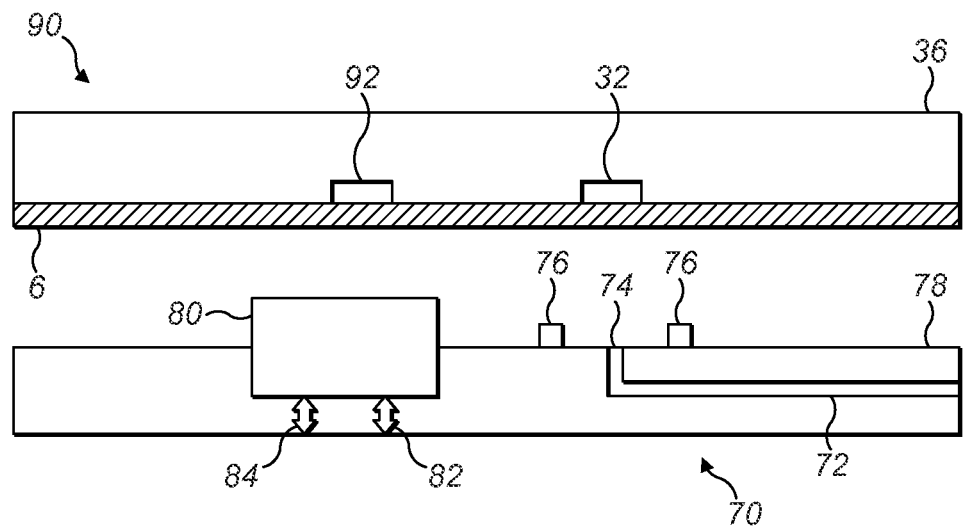
FIG. 39 is a schematic illustration of a microfluidic device and a control platform according to another embodiment.
Figure 40A:
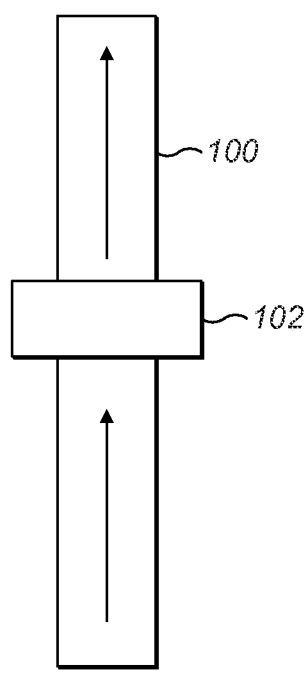
FIGS. 40a and 40b are schematic illustrations of a microfluidic valve.
Figure 40B:
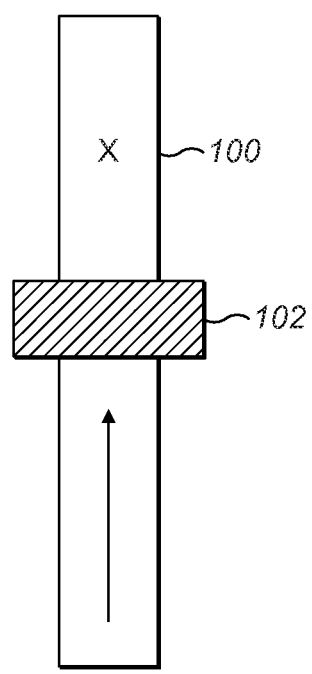
Figure 41A:
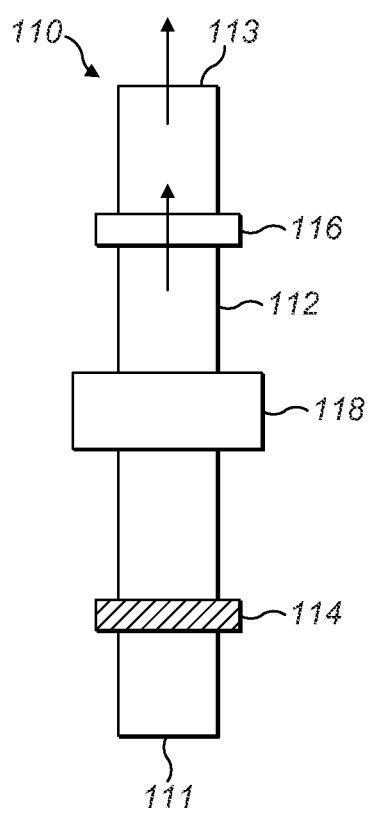
FIGS. 41a and 41b are schematic illustrations of a microfluidic pump or mixer.
Figure 41B:
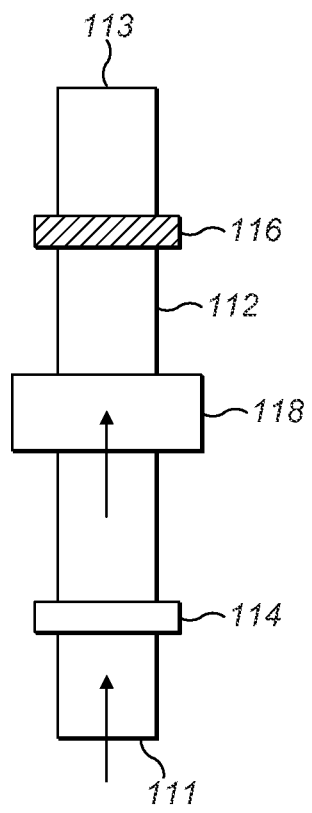
Figure 42:
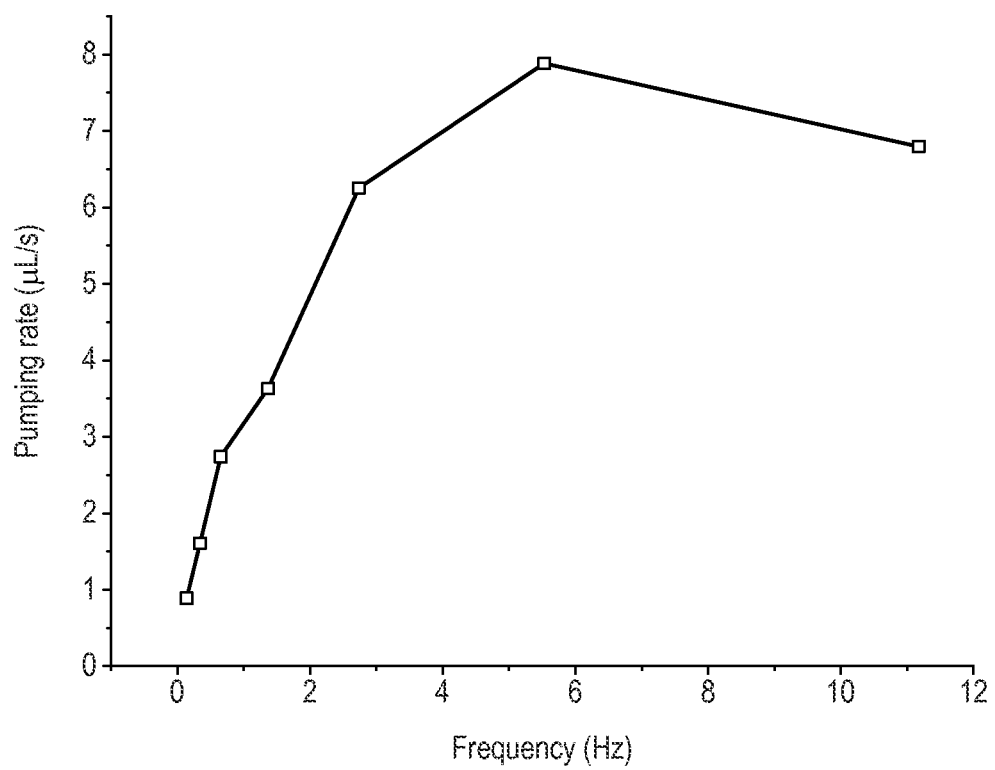
FIG. 42 is a graph of pumping rate as a function of actuator operation frequency for the microfluidic pump of FIGS. 40a and 40b.

A total of 12 pneumatic valves had to be synchronously controlled for driving the liquid flow in the microfluidic chip to and from the reaction chamber, along with one temperature control for the reaction chamber and one magnetic part for trapping and mixing of the magnetic particles to be used in the biological reactions. The valves can be numbered as shown in FIG. 28.

Figure 24:
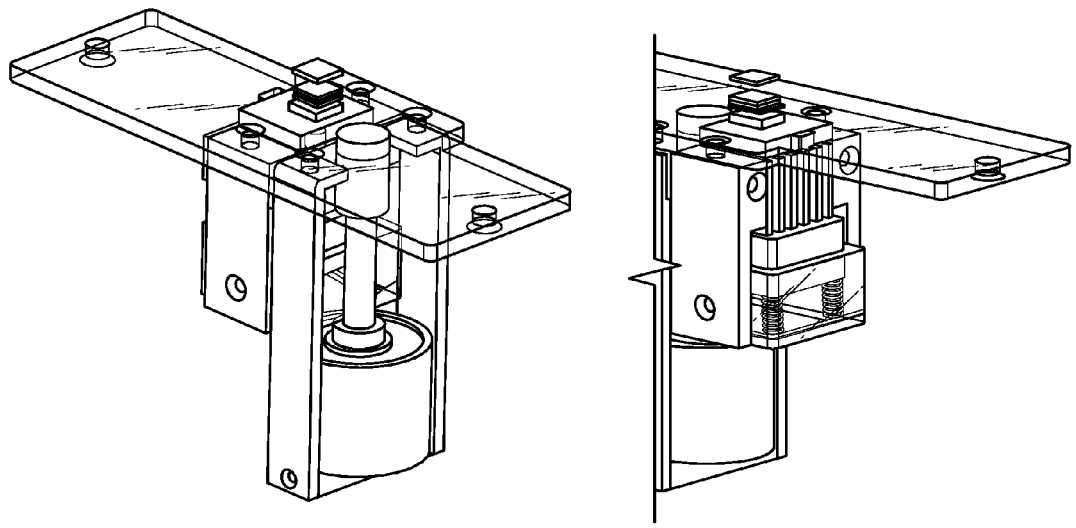
FIG. 24: Isometric left and right views of the heating/cooling and electromagnet sub-assembly.

The microfluidic system used in this Example has three main parts:
  The mechanical assemblies
  The electronics
  The software interface 1. The Mechanical Assemblies The mechanical assemblies can be sub-divided into two separate sub-assemblies. The first one contains both a heating/cooling element and an electromagnet used to magnetize the magnetic particles in the reaction chamber. FIG. 24 shows isometric left and right views of this sub-assembly.

The peltier device sits on a heat sink which in turn is mounted on top of a cooling fan. The peltier was positioned just underneath the reaction chamber, and was placed just on top of the soft iron part used to conduct the magnetic field lines to the reaction chamber. The cooling fan slides in a holder in which the base has an array of four compression springs. The springs are used to press the peltier element against the chip. All the different components are aligned and fixed using a set of four mounting brackets (as seen on the left image).

In addition, the first sub-assembly contains an electromagnet which was used for the magnetic part of the device. The electromagnet also sits on a mounting bracket and has a soft iron bar connected to it. The soft iron bar is used as a magnetic canal to provide the chip with the required magnetic field in order to magnetize the magnetic particles.

As an alternative to the above described heater/cooler module with electromagnet sub-assembly, another possible configuration would be to put the peltier element on top of the machined soft iron part, just underneath the reaction chamber, and replace the electromagnet by a hard magnet which would then allow for both temperature and magnetic control on chip.

Figure 25:
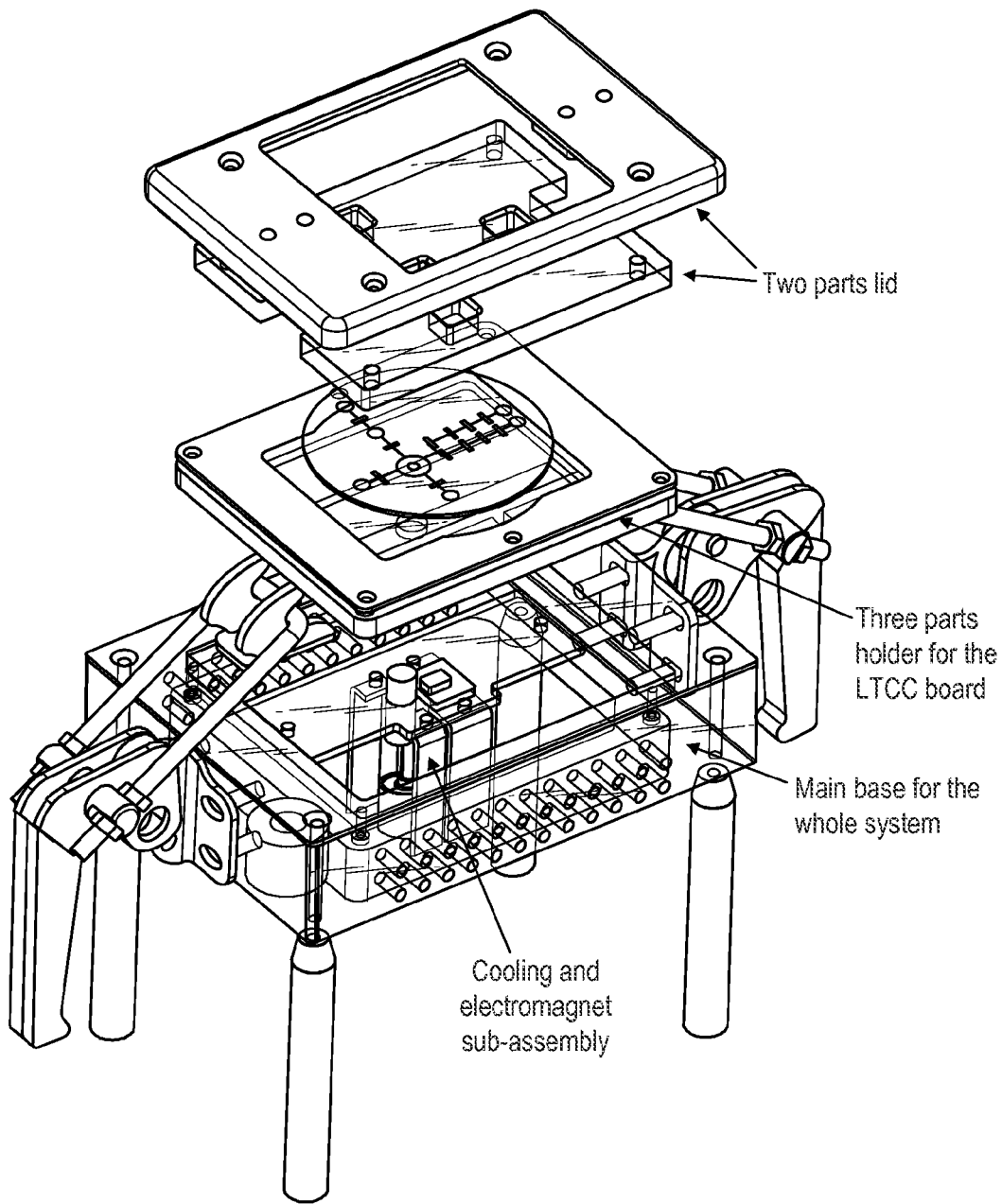
FIG. 25: Isometric view of the mechanical assembly for a control unit for a microfluidic device as described herein, which also includes the heating/cooling and electromagnet sub-assembly.

The second sub-assembly is the mechanical structure that holds all the different mechanical components, air connections, electronics, and on which the microfluidic device is mounted. The 3D design for this sub-assembly is shown in FIG. 25. The choice of plastic board allowed the base plate to be manufactured very quickly and efficiently. This plate sits in a three parts holder which allows both easy alignment of the microfluidic device and enough space for the air connections to come from the bottom of the plastic base.

Finally, all the different mechanical parts sit on a thick plastic base plate, which has all the air connections coming from two opposite sides, and the other two opposites sides have two hook clamps fitted on them. These are used to press the microfluidic device against the plastic board through the two parts lid.

In the absence of an air connection to the reaction chamber, the vibration of the membrane to promote mixing of the different bio-products could be induced using a vibrating piezoelectric film that can adhere to any physical support underneath, and which would generate slight transversal displacements of the membrane.

2. The Electronics

The liquid flow in the microfluidic channels is driven by synchronized pumping sequences. These sequences are controlled from a LabVIEW interface through an electronic platform connected to an array of pneumatic valves. These valves provide compressed air, through sealed connections, to the chip thus deforming the elastic membrane covering the pumps and valves chambers. By using optimized pumping sequences, it is possible to have accurate control of the liquid flow in the microchannels. The electronic board that allows controlling each valve separately, or a set of valves in order to induce pumping sequences, is mainly a relay board made of an array of solid state relays, in which each relay is addressing one single pneumatic valve. This electronic board has two inputs connected to both the DAQ card (with a 25 way cable) and to a power supply, and two outputs connected to the solenoid valves manifolds by the mean of 15 way cables.

To control the peltier device, two thermocouples were used. The first one was placed above the Peltier device while the second one was placed below the reaction chamber. The electronics behind the temperature control of the peltier device relies on the use of a programmable power supply unit, and a National Instruments DAQ card. The Peltier can be controlled and activated via the LabVIEW control interface described below. The temperature can also be monitored via the same interface.

3 LabVIEW Control Interface

A semi-automated LabVIEW interface was used for the control of the microfluidic device platform.

Operation of Microfluidic Device for on-Chip Assembly

Figure 26:
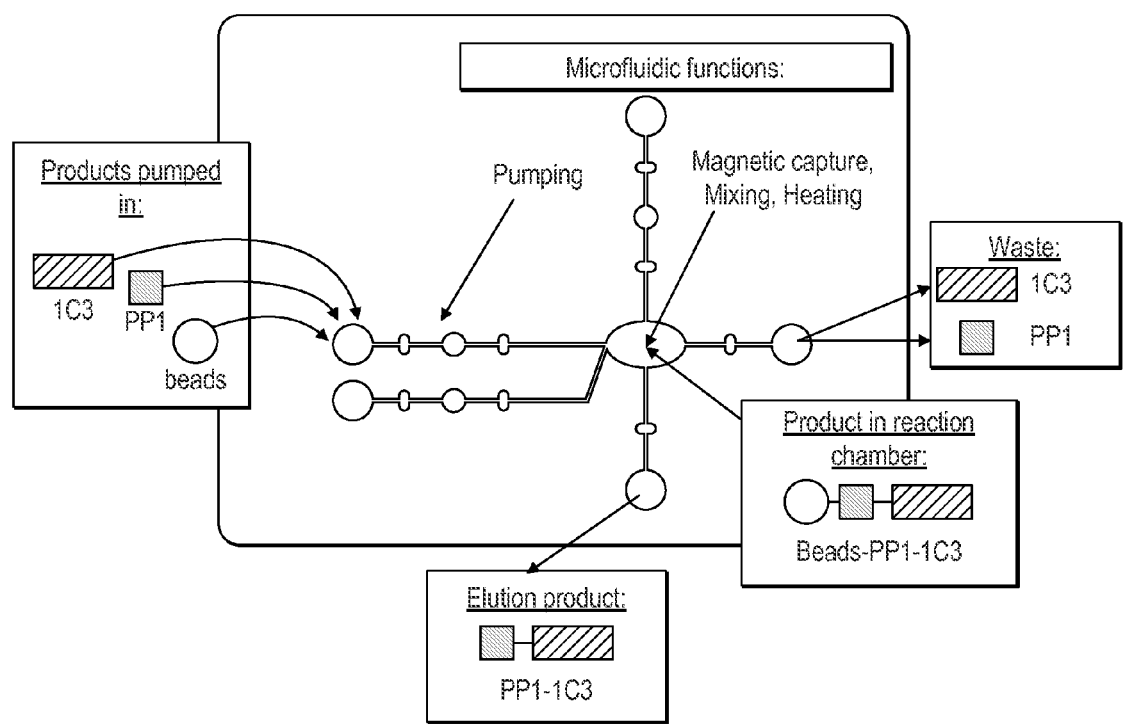
FIG. 26 is a diagram of the microfluidic functions and the different biological components involved in the first purification step of the plasmid pSB1C3 as described in Example 1.

FIG. 26 summarizes how the biology interacts with the different microfluidic functions for a specific example: the first purification (part purification step 1) of the pSB1C3 ligation mix, as shown schematically in FIGS. 9 and 10 (NB in FIG. 26, pSB1C3 is referred to as 1C3). This step and all other purification steps require the entire range of functions present on the microfluidic system: pumping, mixing, magnetic capture and heating. These steps were extensively demonstrated on-chip (see below).

As can be seen from FIG. 26, the products pumped in were the pSB1C3 DNA, the biotinylated purification oligo PP1 and streptavidin magnetic beads. These products were pumped through to the central reaction chamber where magnetic capture of the magnetic beads, mixing of the input products and heating took place. The output of these reactions was the product of pSB1C3-PP1 bound to the magnetic beads by means of the purification oligo PP1. The elution product in one of the output chambers was pSB1C3-PP1 whilst the other output chamber contained the waste, which was unligated pSB1C3 and PP1.

Figure 27:
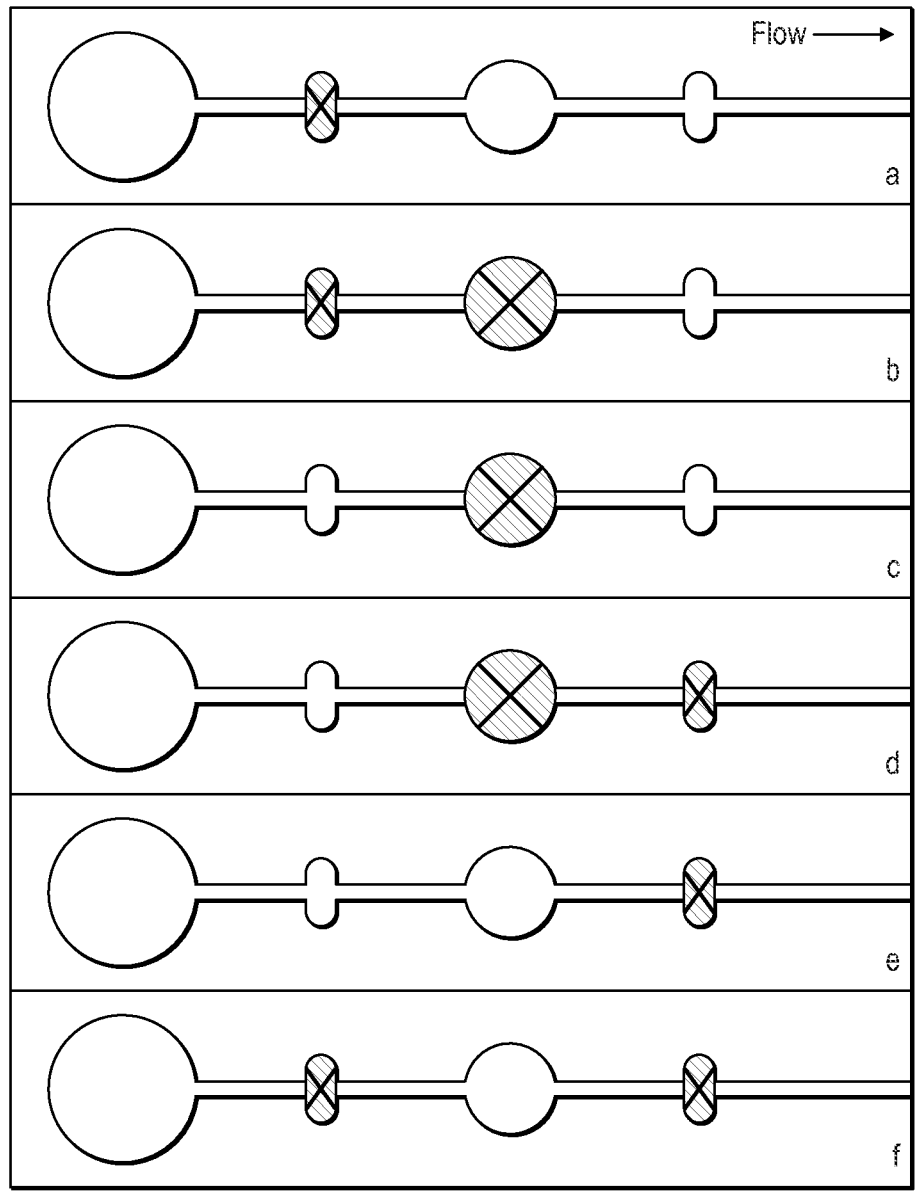
FIG. 27 demonstrates an example of how to operate a pump to flow liquid from one of the chambers into another chamber in a microfluidic device as described herein.

Pumping to flow liquid from one of the input chambers into the reaction chamber was carried out as shown in FIG. 27. In this Example, only one pump between one input chamber and the reaction chamber was used at a time. Therefore, while one pump between one input chamber and the reaction chamber was activated, the other pump between the other input chamber and the reaction chamber remained closed at all times.

FIG. 28 summarises a number of different fluidic steps that were used in this Example and are as described herein.

Magnetic mixing was performed manually, i.e. by moving the magnet above the chamber by hand.

Heating was carried out via a Peltier device placed below the chamber, in direct contact with the elastic membrane Results Results Obtained with the Updated Purification Protocol A Four transformations were performed. Table 1 shows the details of the part ligation and the results obtained. Experiments 3 and 4 represent full off-chip and full on-chip respectively.

TABLE 1

| Experiment | Name of the transformations | ON/OFF CHIP status | Yield (number of colonies) | Efficiency (coloured/ n.coloured cells) |
|---|---|---|---|---|
| 1 | RFP−.1C3+ | PART ON-CHIP | 42 | 33.3% |
| 2 | RFP+.1C3− | PART ON-CHIP | 8 | 37.5% |
| 3 | RFP−.1C3− | OFF-CHIP | 8 | 62.5% |
| 4 | RFP+.1C3+ | ON-CHIP | 102 | 52% |

On the edge on the plate (4) (full on-chip) a 100% efficiency was reached. This appeared to be due to a concentration effect and transformation protocol. One reason that explains the ring of cells on the edge was that the volume of the transformation mixture was too high (850 uL instead of 300 uL): only a small amount of liquid is needed to fill the plate and then the rest of it reaches the edges where it stays highly concentrated. In the subsequent experiment, only 300 uL of transformation mixture was used (see below).

Results Obtained with the Updated Purification Protocol B

Four transformations were performed. Table 2 shows the details of the part ligation and the results obtained. Experiments 3 and 4 represent full off-chip and full on-chip respectively.

TABLE 2

| Experiment | Name of the transformations | ON/OFF CHIP status | Number of colonies | Number of colonies with phenotypic change | Efficiency (%) |
|---|---|---|---|---|---|
| 1 | RFP−.1C3+ | PART ON-CHIP | 14 | 11 | 79% |
| 2 | RFP+.1C3− | PART ON-CHIP | 5 | 4 | 80% |
| 3 | RFP−.1C3− | OFF-CHIP | 12 | 10 | 83% |
| 4 | RFP+.1C3+ | ON-CHIP | 7 | 6 | 86% |

By doubling the washing steps the efficiency of the off-chip purifications was greatly improved. Washing steps to get rid of unwanted oligos seem to be important steps in the on-chip protocol. The transformation protocol in these experiments also used a smaller amount of transformation medium.

In conclusion:

The present inventors have shown that it is possible to carry out assembly of polynucleic acid sequences on-chip The results obtained on-chip are close to the off-chip results.

Example 2—Chip 3A

Figure 14A:
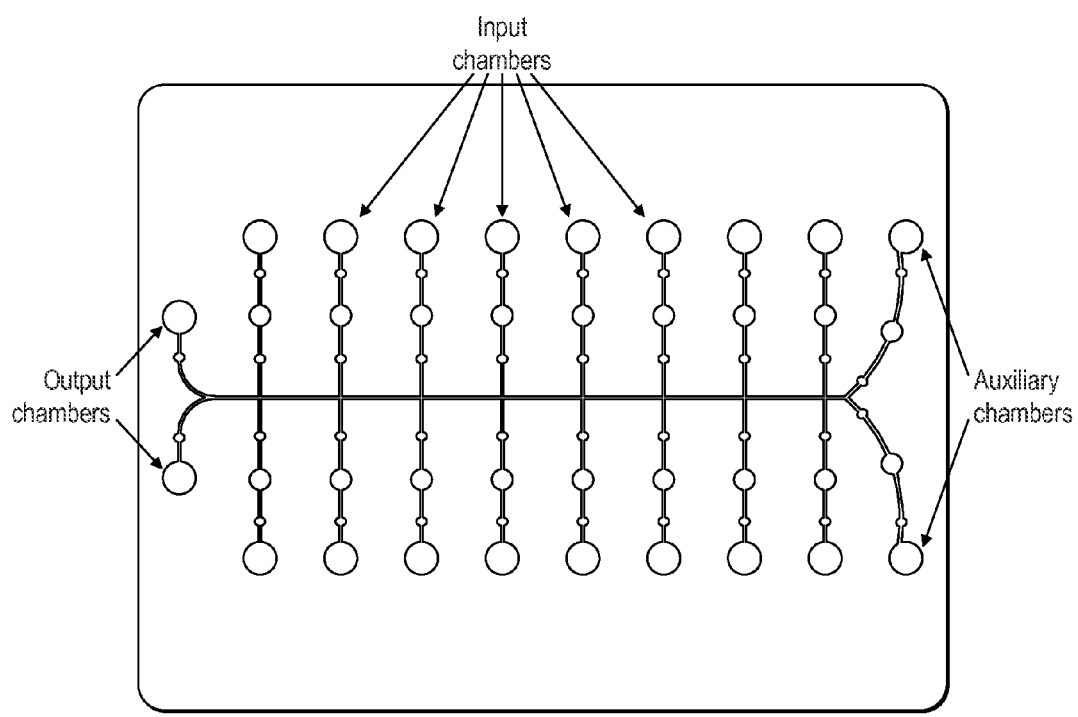
FIG. 14A shows the layout of another microfluidic device for use in the present invention.
Figure 14B:
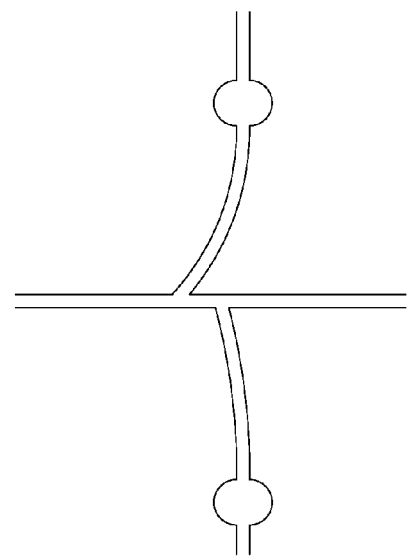
FIG. 14B shows the layout of asymmetric channels in this microfluidic device.
Figure 14C:
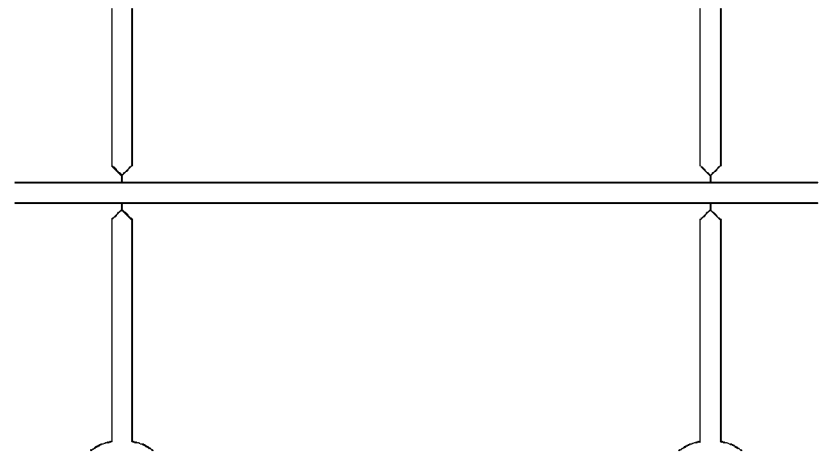
FIG. 14C shows nozzled tip channels in this microfluidic device.
Figure 15:
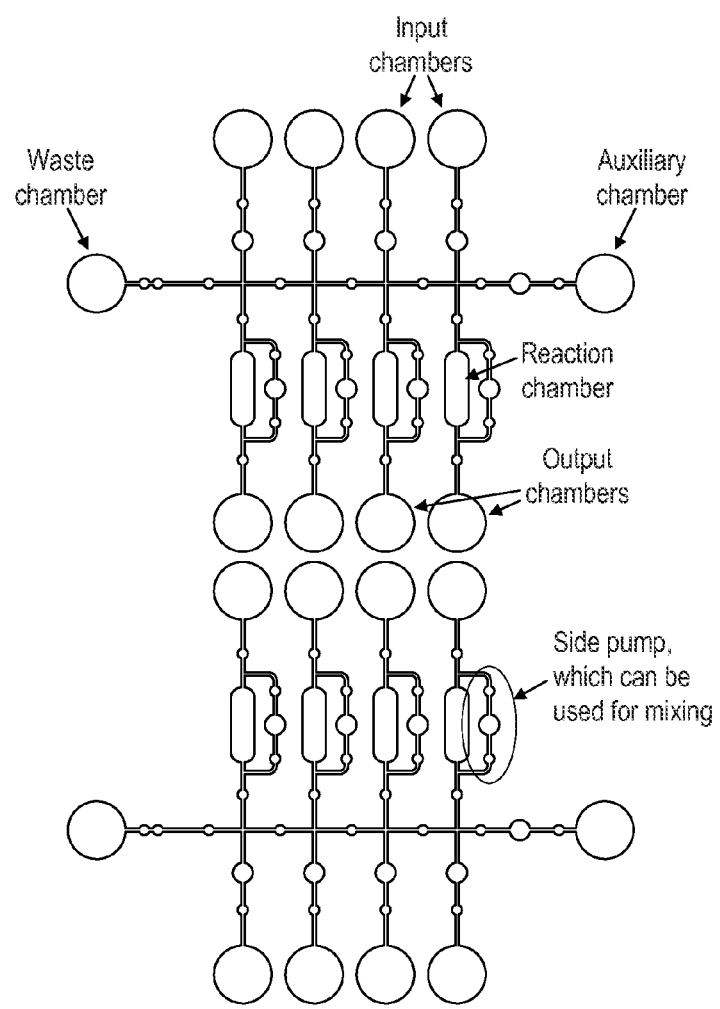
FIG. 15 shows the layout of another microfluidic device for use in the present invention.
Figure 16:
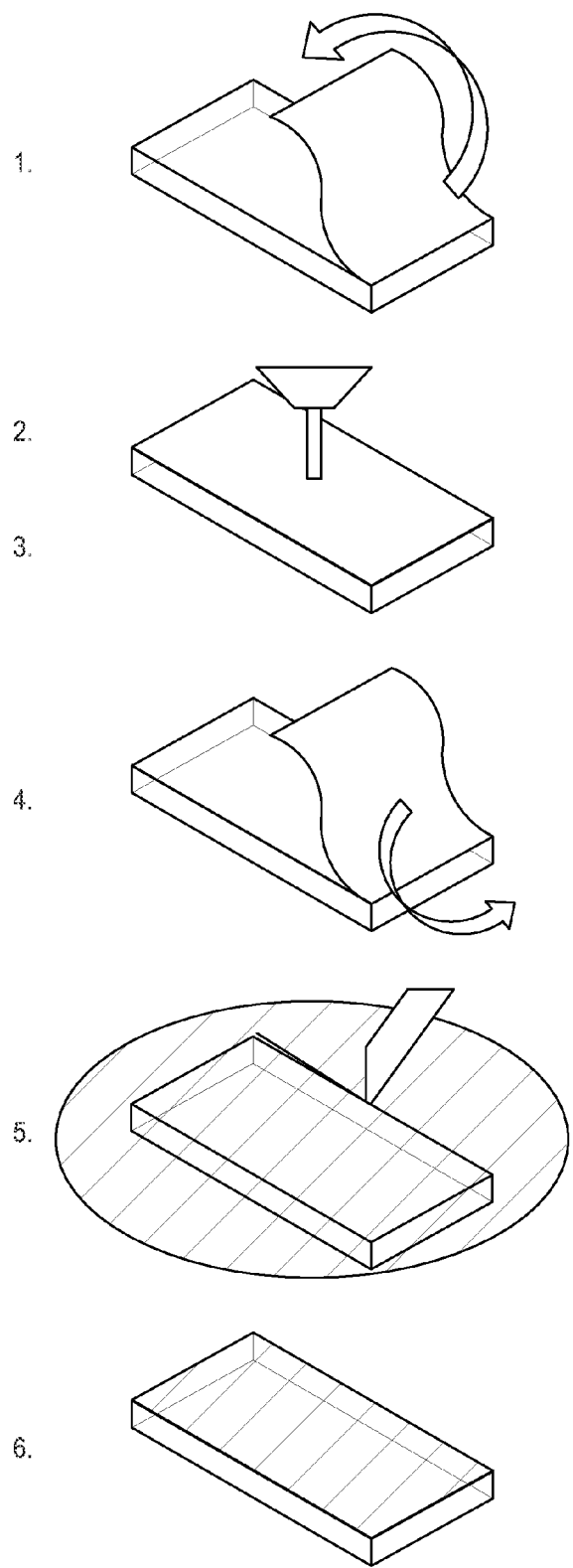
FIG. 16: Packaging of microfluidic membrane using laser cutting and one layer of double-sided adhesive tape. The steps are as follows: 1. 3M Adhesive transfer tape 467 MP applied on the PMMA block. 2. Load the PMMA block into the Epilog tool. Load the CAD file and set the parameters on Corel Draw. 3. Laser rastering and vector cutting. Raster parameters PMMA+tape: 25/100. Vector cutting PMMA+tape: 5/100/5000. 4. Peel the protective layer 5. Apply the membrane on the adhesive layer and deframe it. 6. Chip ready with an excellent bonding
Figure 17:
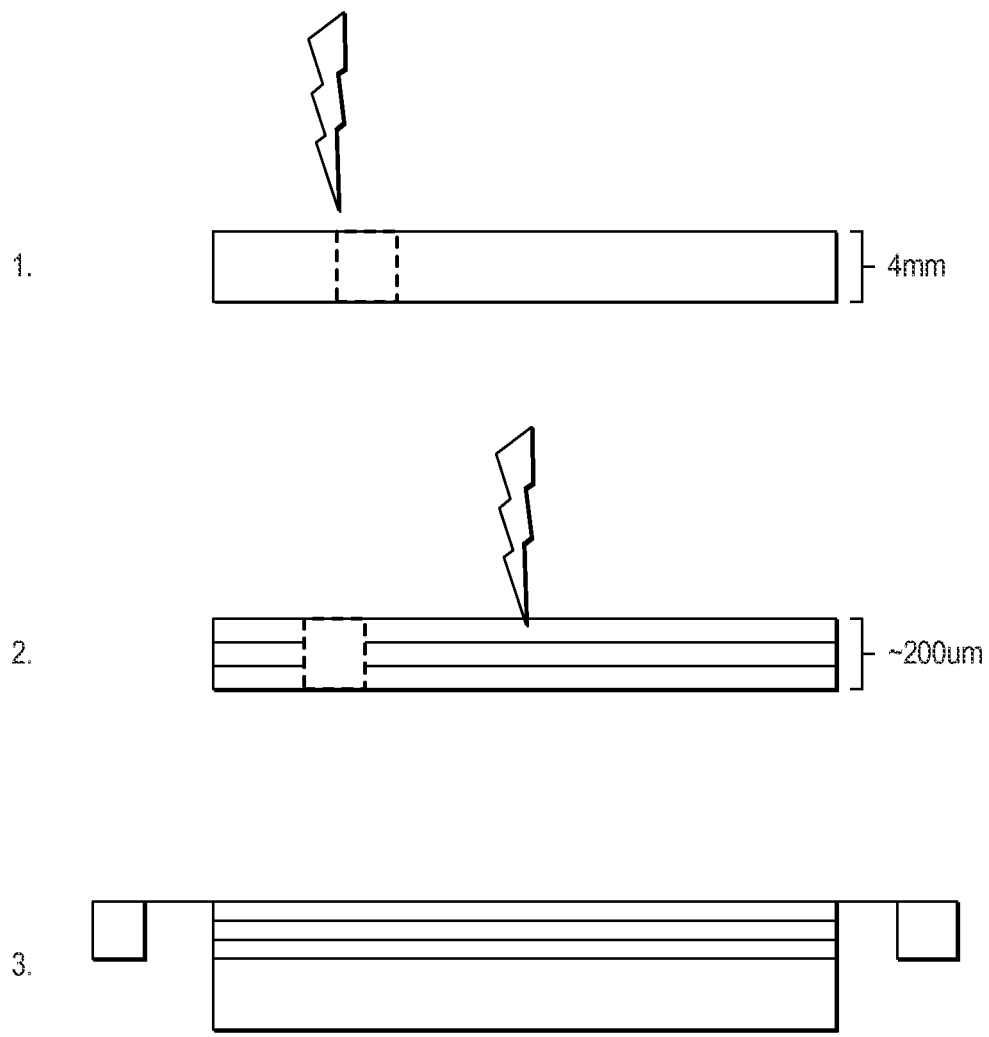
FIG. 17: Cut-through packaging technique using two layers of double-sided adhesive layers. The steps are as follows: 1. Laser cutting of the 4 mm PMMA sheet, Microfluidic access, and edges of the chip. 2. Laser cut-through of the microfluidic channels in a 0.125 mm layer of PMMA covered on both faces with 50 µm adhesive layer and protective cover. 3. Release protective cover, align and bond the channels (2) onto the PMMA block (1). Release the second protective cover and place the membrane.
Figure 18A:
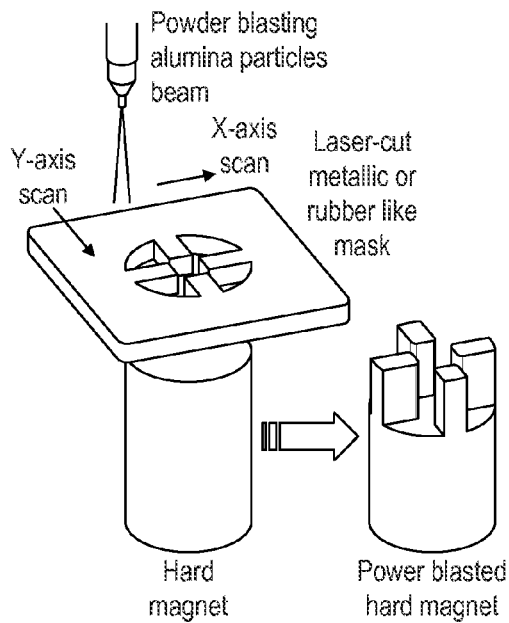
FIG. 18 shows schematic views of the machining of hard magnets using (a) powder blasting and (b) milling or grinding using diamond coated tools; (c) shows some examples of possible machined structures on hard magnets.
Figure 18B:
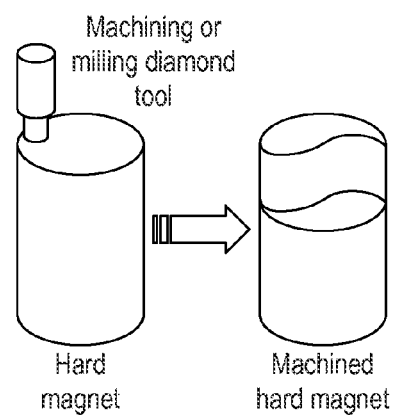
Figure 18C:
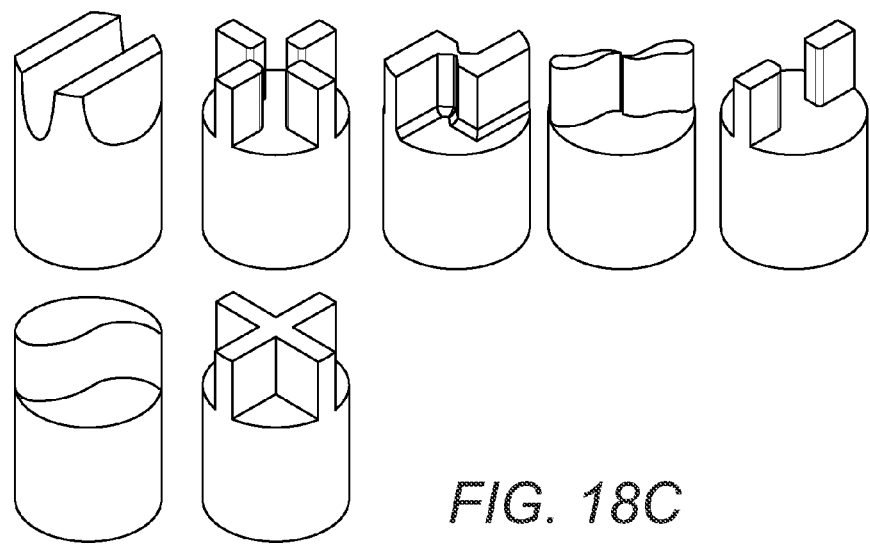
Figure 19:
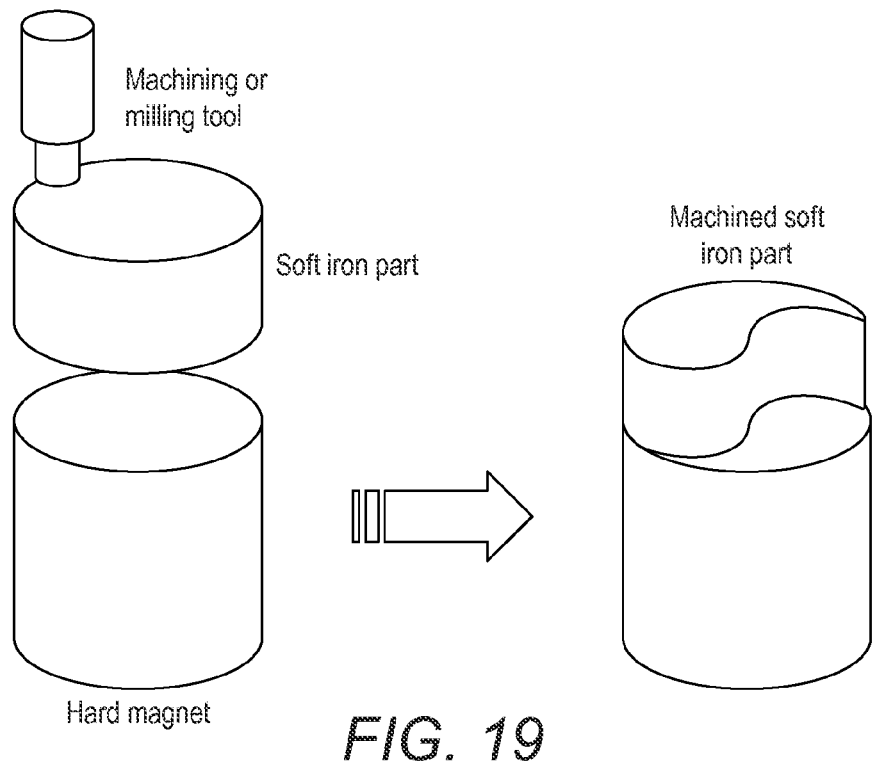
FIG. 19 shows the use of machined soft iron parts to focalise the magnetic field applied in order induce the same effect as for the machined magnets
Figure 20:
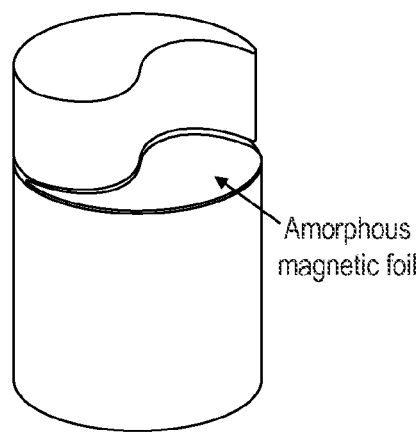
FIG. 20 shows the use of amorphous magnetic materials to cover the exposed or machined areas on the hard magnet.
Figure 21:
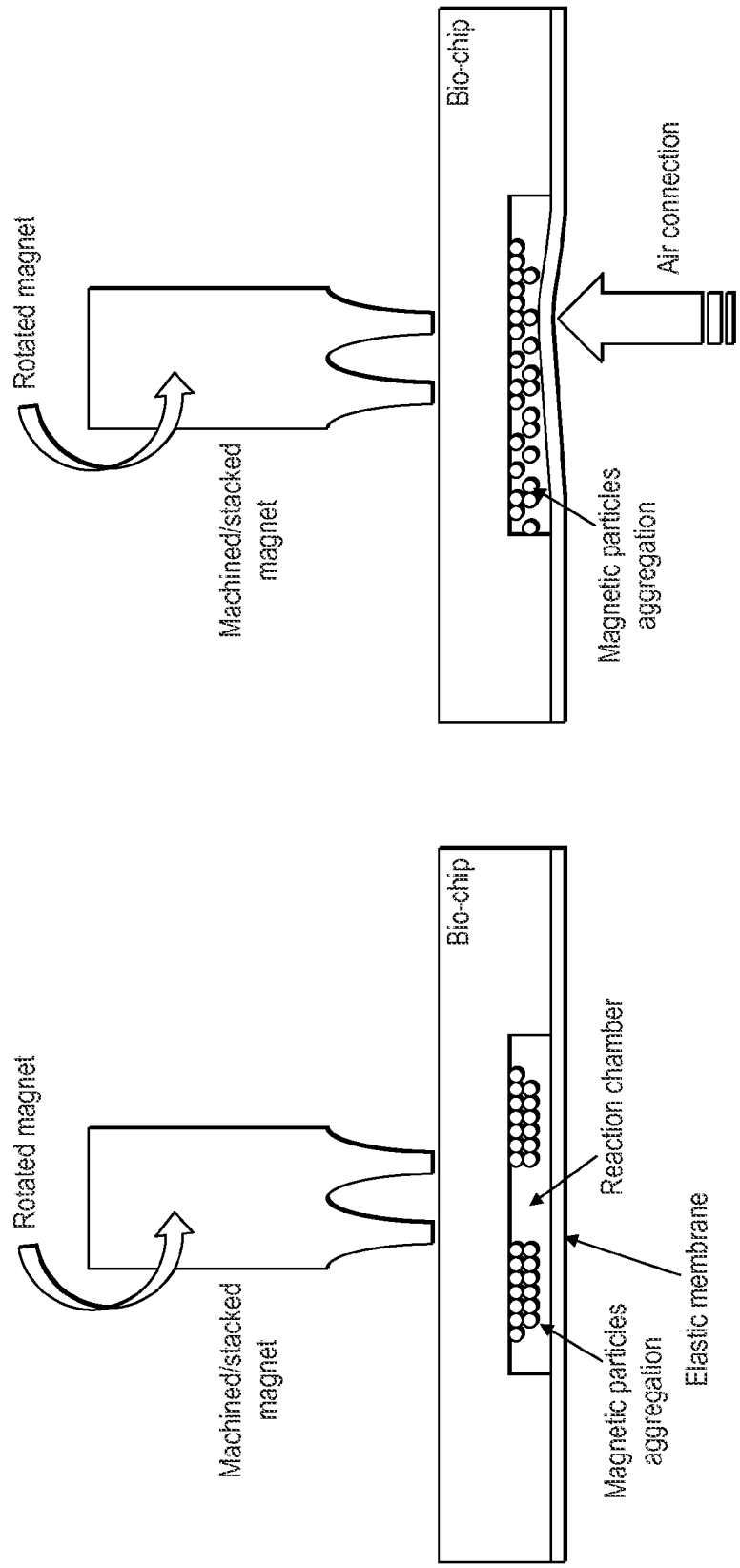
FIG. 21 shows a schematic view showing how the slight vibrations of the membrane can help during the mixing process.
Figure 22A:
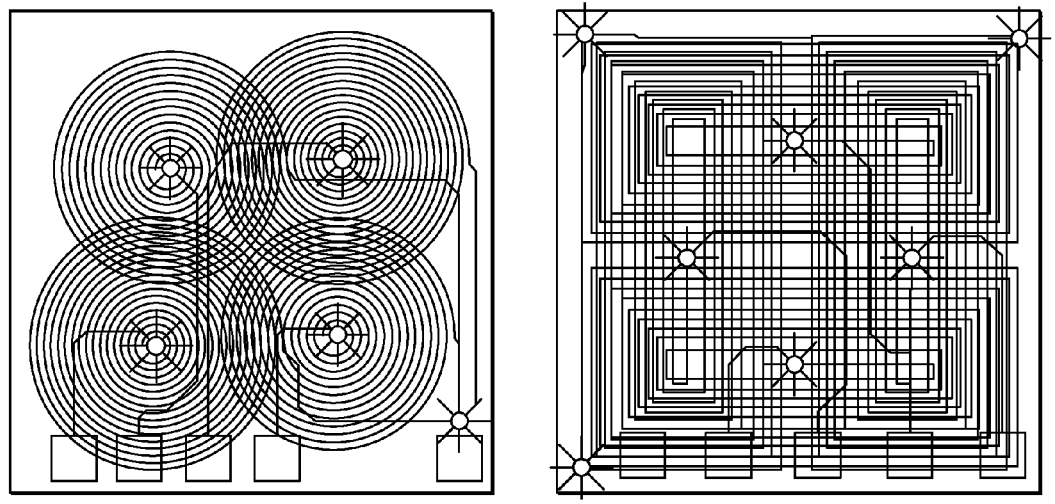
FIG. 22: Schematic views showing the layouts for the magnetic coils for (a) circular and rectangular geometries on PCB board, (b) rectangular and (c) semi-circular geometries for winding enamelled copper wire.
Figure 22B:
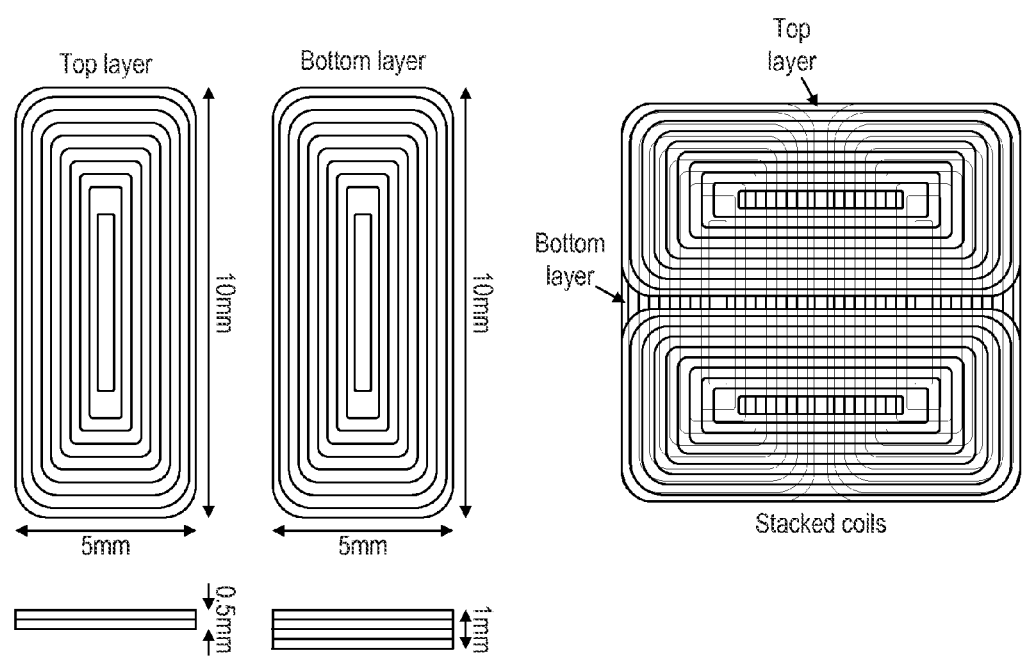
Figure 22C:
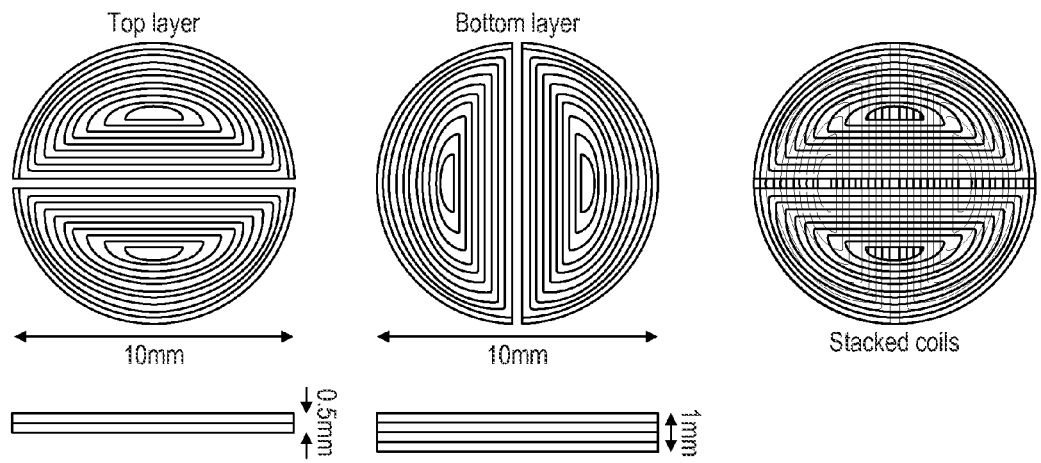
Figure 23A:
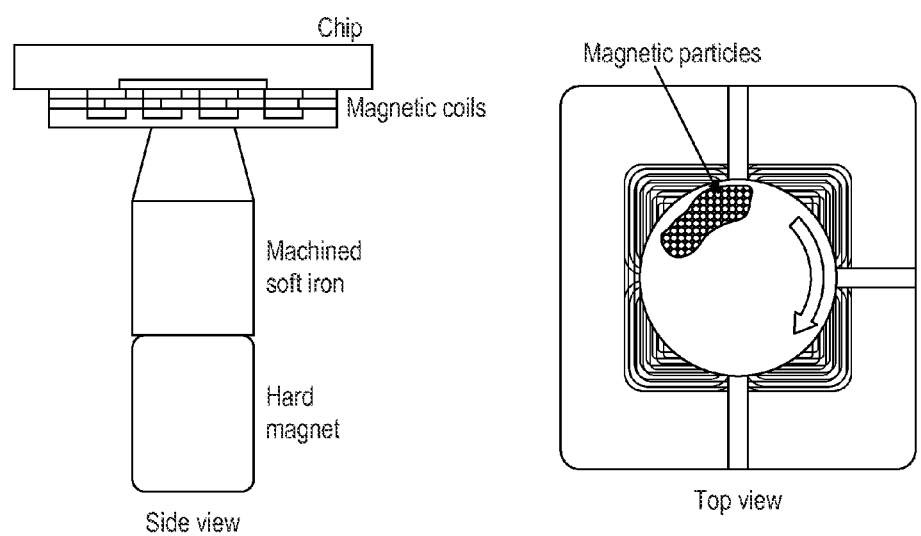
FIG. 23: Schematic top and side views of the magnetic coil based system for separation and mixing of magnetic particles; (a) shows a configuration for which the magnetizing field is applied from under the chip, where the coils are applied, through a machined soft iron part, and (b) shows a configuration in which the magnetizing magnetic field is generated by a stack of hard magnets applied on opposite sides of the chip.
Figure 23B:
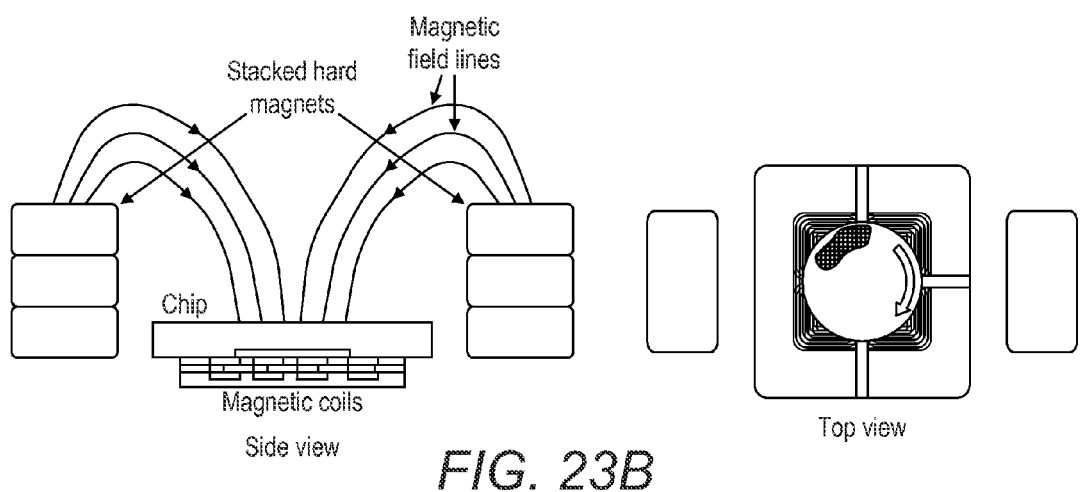

A microfluidic device as shown in FIG. 14A was manufactured using cnc machining and tested by washing fluid through the device.

Example 3—5-Part Assembly on Chip

A five-part assembly (RFP, GFP, KanR, AmpR and pSC101) with 0% contamination was demonstrated twice. Two identical experiments were carried out involving two on-chip tests and two off-chip tests. First of all the 5 parts, buffer and water were loaded into a chip well, The 5 parts and buffer were pumped (~0.5 uL of each part) sequentially into the main channel, pushed into the output well and collected with a pipette to form the product P1. 1 uL of Water from the water well was pumped into the output channel and pipette off the chip to waste. More water and then pumped and formed product P2. P3 was formed by a 5 parts assembly and the addition of 1.5 uL composed equally of blue and yellow food dye solution and mineral oil. P4 was a conventional off-chip 5 part assembly.

Table 3 summarizes the different products transformed and the results obtained.

TABLE 3

| Plate number | Content | Result |
|---|---|---|
| P1 | 5 parts ON-CHIP Assembly | Assembly successful |
| P2 | Water control | No contamination |
| P3 | 5 parts OFF-CHIP Assembly (with added dyes) | Assembly successful |
| P4 | 5 parts OFF-CHIP Assembly | Assembly successful |

In conclusion, a 5 part assembly without subsequent contamination has been demonstrated (n=2) on chip.

Example 4—10 Part-Assembly on Chip

Violacein Biosynthetic Pathway

Figure 43A:
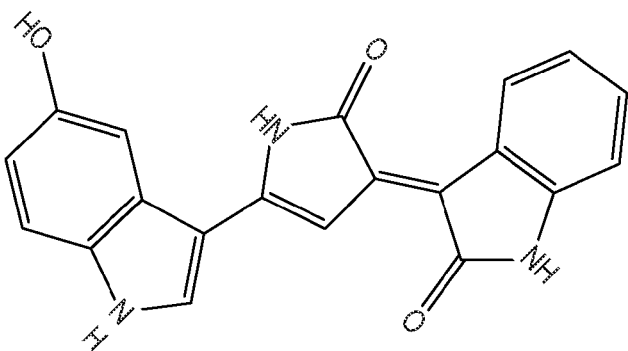
FIG. 43: (A) Chemical structure of the indole-derivative, Violacein. (B) The biosynthesis of violacein from the precursor, L-tryptophan. Note that VioC and VioD have overlapping function and thus, only VioC was utilized in the assemblies.
Figure 43B:
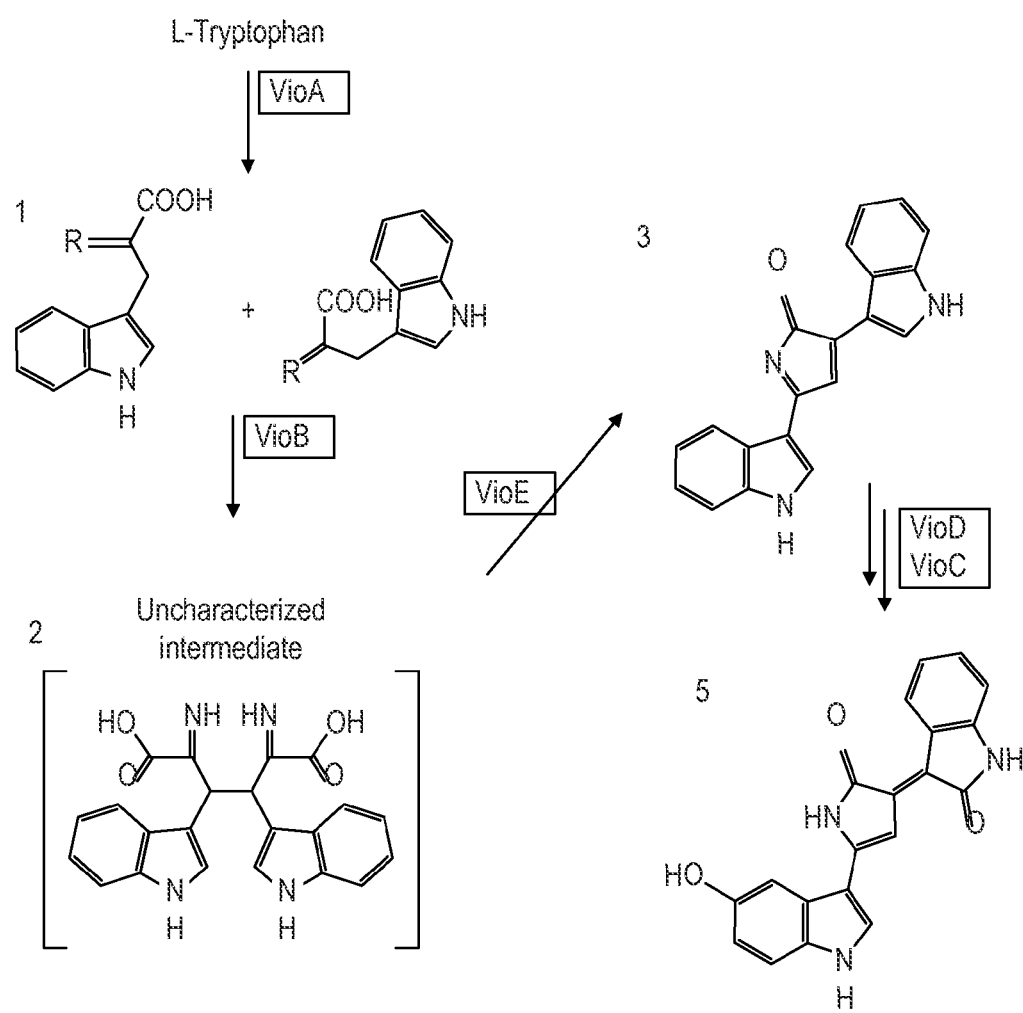

Violacein is an industrially-relevant, indole derivative possessing anti-tumoral, anti-ulcerogenic, antitumorigenic, antitrypanosomatid, and antiviral activities. FIG. 43A shows the chemical structure of Violacein. Biosynthesis of this product can be performed heterologously in E. coli and requires only 4 biosynthetic genes. FIG. 43B shows the biosynthesis of violacein from the precursor, L-tryptophan. The intensely colored violacein pigment can be used to diagnose successful assemblies, greatly aiding the assembly debugging process.

10-Part Assembly Design

The 10-way assembly contained the following parts:

TABLE 4

| Part Name | Part Description | Part Number |
|---|---|---|
| Kan kinase | Provides cells with resistance to the antibiotic, kanamycin | 1076 |
| vioA | Violacein biosynthetic enzyme | 1217 |
| vioB-alpha | Violacein biosynthetic enzyme, first domain of vioB | 1471 |
| vioB-beta | Violacein biosynthetic enzyme, second domain of vioB | 1475 |
| vioC | Violacein biosynthetic enzyme | 1223 |
| vioE | Violacein biosynthetic enzyme | 1225 |
| GFP | Includes a promoter and RBS, yields Green Fluorescent Protein | 1097 |
| P15a origin | Allows for plasmid replication by e. coli (medium copy) | 1532 |
| RFP | Includes a promoter and RBS, yields Red Fluorescent Protein | 1104 |
| β-lactamase | Provides cells with resistance to the antibiotic, ampicillin | 1109 |

Part Preparation for High-Order Assemblies

The 10 parts were prepared and then assembled on-chip. Part preparation methods are described below.

Linked Ligation/Digestion Reaction Conditions

Figure 44:
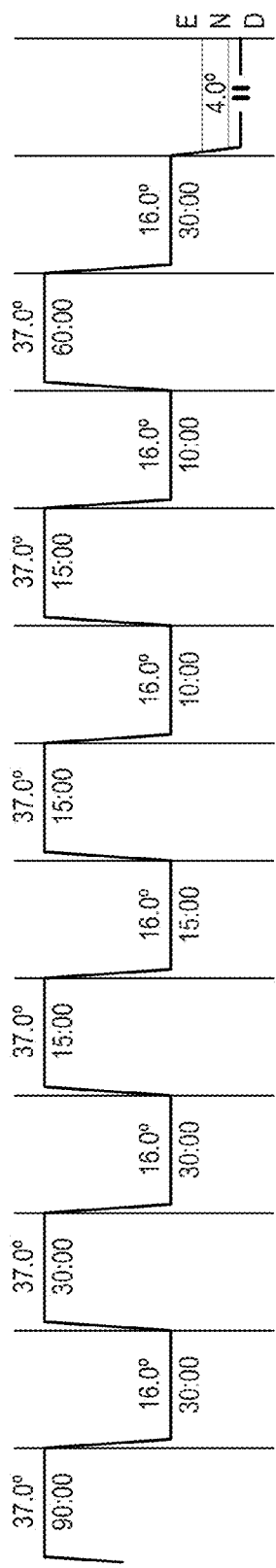
FIG. 44 shows the thermocycler conditions used for the linked ligation/digestion reactions in Example 4.

Each part Cloned vector was miniprepped from 4 mL of culture media and eluted in 50 uL EB buffer. Linked ligation-digestion reactions were setup, using a 40× dilution of T4 DNA ligase and EarI in 1×NEB buffer #2 supplemented with 1 mM ATP. Each reaction contained a 25-fold excess of the appropriate pre-annealed LOA and POA oligos. Reaction volumes were typically 90 uL. Reactions were run in a thermo cycler as shown in FIG. 44.

Figure 45:
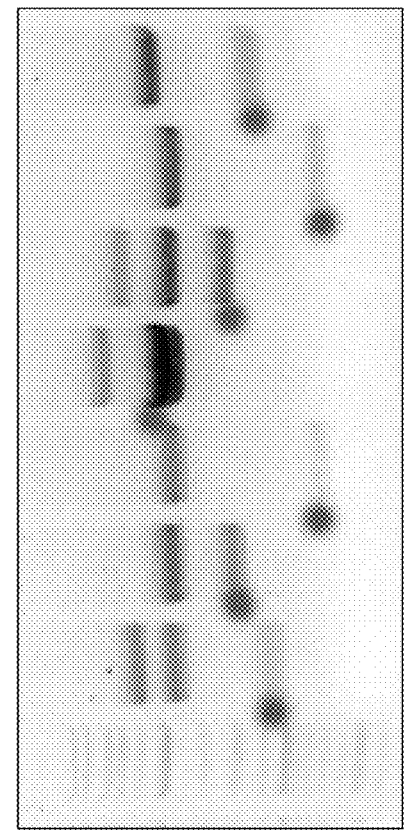
FIG. 45 shows the results of gel based purification of the pathway assembly components in Example 4.

Gel-Based Purification of Pathway Assembly Components 65 uL of each reaction was then run on a 1% agarose gel and the appropriate products were extracted from the gel using a Qiagen kit and eluted from the column using 50 uL EB. FIG. 45 shows the gel for fragments 1-7. The dots indicate the extracted band.

Pathway Assembly Off-Chip and on-Chip

Off-Chip Pathway Assembly Steps

A control assembly was conducted off-chip in order to compare to the assembly conducted on chip. The method used was as follows: DNA concentration of each part was normalized and mixed in the presence of 1×NEBuffer #2. Assembly reactions were run for 20 minutes at room temperature. 3 uL of the assembly reaction was then used to transform chemically-competent NEB 10 B cells. Transformed cells were recovered in SOC for 1 hour at 37 C before plating on LB/agar/kanamycin plates.

On-Chip Pathway Assembly Steps

The assembly was conducted on-chip using a computer numerically controlled (CNC) machined chip.

On-Chip Pathway Assembly Results

Successful assemblies were verified by display of the correct colored colony phenotype and the results are shown in Table 5 below. The off-chip and on-chip showed essentially equivalent efficiency (88% correct transformants). The total yield was slightly lower on-chip, however the total number of colonies was well above that needed for ensuring a successful assembly. The water controls demonstrated that there was negligible contamination.

TABLE 5

| Plate number | Description | Results | Yield |
|---|---|---|---|
| P1 | Water control before assembly | No contamination | — |
| P2 | 10 parts on chip | 88.1% of cells correctly transformed | Total 84 cells |
| P3 | Water control after assembly | No contamination | — |
| P4 | 10 parts off chip | 88.2% of cells correctly transformed | Total 102 cells |

The invention claimed is:

1. A method for the assembly of a polynucleic acid sequence from a plurality of nucleic acid sequences in which the polynucleic acid sequence is of a formula $N_{n+1}$, in which N represents a nucleic acid sequence and where n is 1 or greater than 1 and each N may be the same or a different nucleic acid sequence, in which the method comprises:
  (i) providing a first nucleic acid sequence N1 which has an oligonucleotide linker sequence $L1^{3'}$ attached at the 3'-end of the nucleic acid sequence;
  (ii) providing a second nucleic acid sequence N2 which optionally has an oligonucleotide linker sequence $L2^{3'}$ attached at the 3'-end of the nucleic acid sequence and which has an oligonucleotide linker sequence $L2^{5'}$ attached at the 5'-end of the nucleic acid sequence, wherein the 5'-end linker sequence $L2^{5'}$ of nucleic acid sequence N2 is complementary to the 3'-end linker sequence $L1^{3'}$ of nucleic acid sequence N1;
  (iii) optionally providing one or more additional nucleic acid sequences N, wherein nucleic acid sequence N2 has an oligonucleotide linker sequence $L2^{3'}$ attached at the 3'-end of the nucleic acid sequence, and wherein said one or more additional nucleic acid sequences N comprises a terminal additional nucleic acid sequence NZ, and wherein each additional nucleic acid sequence N has an oligonucleotide linker sequence attached at its 3'-end, wherein said terminal additional nucleic acid sequence NZ optionally lacks an oligonucleotide linker sequence at its 3'-end and wherein each additional nucleic acid sequence N has an oligonucleotide linker sequence attached at its 5'-end, wherein for the first additional nucleic acid sequence N3 the 5'-end linker sequence $L3^{5'}$ is complementary to the 3'-end linker sequence $L2^{3'}$ of nucleic acid sequence N2 and for each second and subsequent additional nucleic acid sequence N the 5'-end linker sequence is complementary to the 3'-end linker sequence of the respective preceding additional nucleic acid sequence;
  (iv) ligating said nucleic acid sequences to form said polynucleic acid sequence, wherein said nucleic acid sequences are optionally purified immediately prior to said ligating;

wherein at least step (iv) is carried out on a microfluidic device; and
  wherein the method does not require polymerase.

2. A method according to claim 1, wherein said first nucleic acid sequence N1 has an oligonucleotide linker sequence $L1^{5'}$ attached at the 5'-end of the nucleic acid sequence; or wherein said second nucleic acid sequence N2 has an oligonucleotide linker sequence $L2^{3'}$ attached at the 3'-end of the nucleic acid sequence; or wherein said terminal additional nucleic acid sequence NZ has an oligonucleotide linker sequence $LZ^{3'}$ attached at the 3'-end of the nucleic acid sequence; or wherein said first nucleic acid sequence N1 has an oligonucleotide linker sequence $L1^{5'}$ attached at the 5'-end of the nucleic acid sequence, and wherein said second nucleic acid sequence N2 has an oligonucleotide linker sequence $L2^{3'}$ attached at the 3'-end of the nucleic acid sequence, and wherein the 5'-end linker sequence $L1^{5'}$ of nucleic acid sequence N1 is complementary to the 3'-end linker sequence $L2^{3'}$ of nucleic acid sequence N2; or wherein said first nucleic acid sequence N1 has an oligonucleotide linker sequence $L1^{5'}$ attached at the 5'-end of the nucleic acid sequence, and wherein said terminal additional nucleic acid sequence NZ has an oligonucleotide linker sequence $LZ^{3'}$ attached at the 3'-end of the nucleic acid sequence, and wherein the 5'-end linker sequence $L1^{5'}$ of nucleic acid sequence N1 is complementary to the 3'-end linker sequence $LZ^{3'}$ of nucleic acid sequence NZ.

3. A method according to claim 1, wherein each of said 3'-end linker sequences and said 5'-end linker sequences is partially double stranded; or wherein each said nucleic acid sequence has an overhang at each end.

4. A method according to claim 3, wherein said overhang at each end of said nucleic acid sequence is produced by digestion with one or more restriction enzymes; or wherein said overhang is 3 or 4 nucleotides in length; or wherein the overhang at the 3'-end of the nucleic acid sequence and/or at the 5'-end of the nucleic acid sequence is the same for each nucleic acid sequence.

5. A method according to claim 1, wherein each said nucleic acid sequence is attached to its said 3'-end linker sequence and to its said 5'-end linker sequence by ligation.

6. A method according to claim 1, wherein said nucleic acid sequences are purified on the microfluidic device; or purified using DNA purification spin columns or gel extraction.

7. A method according to claim 1, wherein each said nucleic acid sequence is a protein coding sequence or a regulatory or control element.

8. A method according to claim 1, wherein step (iv) is carried out using DNA ligase.

9. A method for the preparation of a library of polynucleic acid sequences, the method comprising simultaneously producing a plurality of different polynucleic acid sequences using the method according to claim 1.

\* \* \* \* \*